(12) United States Patent
Humphrey et al.

(10) Patent No.: US 7,381,741 B2
(45) Date of Patent: Jun. 3, 2008

(54) 3-AMINO-2-PHENYLPYRROLIDINE DERIVATIVES

(75) Inventors: John Michael Humphrey, Mystic, CT (US); Thomas Allen Chappie, Old Lyme, CT (US)

(73) Assignee: Pfizer Inc, New York, NY (US)

( * ) Notice: Subject to any disclaimer, the term of this patent is extended or adjusted under 35 U.S.C. 154(b) by 445 days.

(21) Appl. No.: 11/136,913

(22) Filed: May 25, 2005

(65) Prior Publication Data

US 2005/0288358 A1    Dec. 29, 2005

Related U.S. Application Data

(60) Provisional application No. 60/574,116, filed on May 25, 2004.

(51) Int. Cl.
*A61K 31/40*    (2006.01)
*A61K 31/4025*    (2006.01)
*C07D 207/04*    (2006.01)

(52) U.S. Cl. ............... 514/426; 548/517; 548/518; 548/557; 514/408; 514/422

(58) Field of Classification Search .............. 548/517, 548/518, 557; 514/408, 422
See application file for complete search history.

(56) References Cited

U.S. PATENT DOCUMENTS

| 5,232,929 A | 8/1993 | Desai et al. |
| 6,194,436 B1 * | 2/2001 | Howard ..................... 514/326 |
| 6,376,507 B1 * | 4/2002 | Nelson et al. ............. 514/294 |
| 2003/0008892 A1 | 1/2003 | Coe et al. |

* cited by examiner

*Primary Examiner*—Golam M Shameem
(74) *Attorney, Agent, or Firm*—Steve T. Zelson; Andrea E. Dorigo; E. Victor Donahue

(57) ABSTRACT

3-amino-2-phenylpyrrolidine compounds useful as NK-1 antagonists, with pharmaceutical compositions and methods of treatment comprising same, are disclosed.

8 Claims, No Drawings

3-AMINO-2-PHENYLPYRROLIDINE DERIVATIVES

The entire disclosure of parent application 60/574,116 filed May 25, 2004 is fully incorporated herein by reference thereto.

The invention is directed to 3-amino-2-phenylpyrrolidine compounds useful as NK-1 antagonists; to pharmaceutical compositions comprising the same; and to methods of treating disorders using the same. The invention also relates to NK-1 antagonisim.

BACKGROUND OF THE INVENTION

The mammalian peptide Neurokinin B (NKB) belongs to the Tachykinin (TK) peptide family which also includes Substance P (SP) and Neurokinin A (NKA). Pharmacological and molecular biological evidence has shown the existence of three subtypes of TK receptors (NK-1, NK-2 and NK-3). Substance P (also known as NK-1) is a naturally occurring undecapeptide so named due to its prompt stimulatory action on smooth muscle tissue. More specifically, substance P is a pharmacologically active neuropeptide produced in mammals and possessing a characteristic amino acid sequence as illustrated in U.S. Pat. No. 4,680,283. Selective peptidic NK-3 receptor antagonists are also known (Drapeau, 1990 Regul. Pept., 31, 125-135).

Given the prevailing involvement of NK-1, efforts to develop antagonists thereto have been ongoing. Among these are the compounds disclosed in U.S. Pat. No. 5,232,929 having the formula:

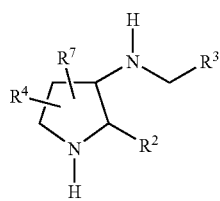

wherein inter alia $R^4$ and $R^7$ can be H; $R^2$ can be phenyl optionally substituted with halo or alkyl groups; and $R^3$ can be phenyl or naphthyl optionally substituted with halo, nitro, $(C_{1-6})$alkyl, $(C_{1-6})$alkoxy, trifluoromethyl, phenyl, amino, $(C_{1-6})$alkylamino, —(C═O)—NH—$(C_{1-6})$alkyl, $(C_{1-6})$alkyl-C(═O)—NH—$(C_{1-6})$alkyl, —NHC(═O)H and —NHC(═O)—$(C_{1-6})$alkyl; specifically cis-3-(2-methoxybenzylamino)-2-phenyl-pyrrolidine.

Additionally, U.S. patent Publication No. 2003/0008892 A1 discloses 3-(2-methoxy-5-trifluoromethoxybenzyl)amino-2-phenylpyrrolidine.

Notwithstanding, the development of NK-1 antagonists having improved activity and/or stability continues.

SUMMARY OF THE INVENTION

In one practice, the invention relates to a compound having formulae:

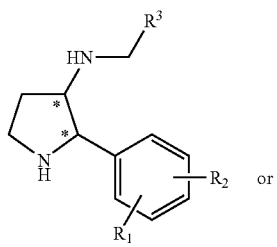

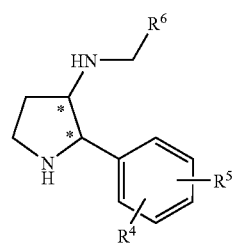

or a pharmaceutically acceptable salt or solvate thereof, wherein:

$R^1$ and $R^2$ are each independently H, $C_{1-6}$alkyl or halo;

$R^3$ is phenyl, bi-phenyl, 6-methoxy-3-methyl-1,1a,3,7b-tetrahydro-3-aza-cyclopropa[a]naphthalen-2-one, 6-methoxy-1-methyl-3,4-dihydro-1H-[1,5]naphthyridin-2-one-7-yl, dibenzofuranyl, 6-methoxy-3-methyl-1,1a,3,7b-tetrahydro-3-aza-cyclopropa[a]naphthalen-2-one-5-yl or naphthyl, all of which are substituted with 1 to 3 substituents independently selected from hydroxy, $C_{3-6}$ cycloalkoxy, benzo($C_{3-6}$)cycloalkoxy, $C_{1-6}$ alkylthio, tetrazole, or $C_{6-10}$ aryloxy, said aryloxy or tetrazole being optionally substituted with 1 to 3 substituents independently selected from halo, $C_{1-4}$ alkoxy, cyano, $C_{1-4}$ haloalkyl or $C_{1-4}$ alkyl;

or $R^3$ is phenyl, to which is fused a $C_{3-6}$ cycloalkyl, a $C_{4-5}$ lactam, thiazole, pyridone, pyran, dioxolan or benzofuran, wherein the C—N and C-phenyl bonds at the C atoms denoted * are in the cis or trans position relative to each other;

$R^4$ is H or halo;

$R^5$ is H or $C_{1-6}$ alkyl; and $R^6$ is selected from phenyl, indanyl, pyridinyl, benzothiazoyl, thiophenyl, furanyl, quinolinyl, benzothiophenyl, benzofuranyl, isochromanyl, chromanyl, or naphthyl, and $R^6$ can be optionally substituted with 1 to 3 of the substitutents independently selected from halo, $C_{1-6}$ alkyl, $C_{1-6}$ haloalkyl, $C_{1-6}$ alkoxy, $C_{1-6}$ haloalkoxy, piperidinyl or phenyl; wherein the C—N and C-phenyl bonds at the C atoms denoted * are in the cis or trans position relative to each other, with the provisos that said compound not be cis-3-(2-methoxybenzylamino)-2-phenyl-pyrrolidine, nor 3-(2-methoxy-5-trifluoromethoxybenzyl)amino-2-phenylpyrrolidine.

In another practice, the invention relates to a pharmaceutical composition for antagonizing the effects of substance P in a mammal, comprising a substance P antagonizing amount of a compound according to Formulae I or II, or a pharmaceutically acceptable salt or solvate thereof, and a pharmaceutically acceptable carrier.

In another practice, the invention relates to a pharmaceutical composition for treating in a mammal a condition associated with the effect of excess substance P at its receptor site, comprising an amount of a compound according to Formulae I or II, or a pharmaceutically acceptable salt or solvate thereof, effective in antagonizing the effect of substance P at its receptor site, and a pharmaceutically acceptable carrier.

In another practice, the invention relates to a pharmaceutical composition for treating in a mammal a condition associated with the effect of excess substance P at its receptor site, comprising an amount of a compound according to Formulae I or II, or a pharmaceutically acceptable salt or solvate thereof, effective in treating said condition and a pharmaceutically acceptable carrier.

In another practice, the invention relates to a pharmaceutical composition for treating in a mammal a condition selected from the group consisting of sleep disorders, autism, pervasive development disorder, rheumatoid arthritis, osteoarthritis, fibromyalgia, human immunodeficiency virus (HIV) infections, dissociative disorders, anorexia, bulimia, ulcerative colitis, Crohn's disease, irritable bowel syndrome, functional abdominal pain, chronic fatigue syndrome, sudden infant death syndrome (SIDS), overactive bladder, chronic cystitis, chemotherapy induced cystitis, cough, angiotensin converting enzyme (ACE) induced cough, itch, hiccups, premenstrual syndrome, premenstrual dysphoric disorder, schizophrenia, schizoaffective disorder, delusional disorder, substance-induced psychotic disorder, brief psychotic disorder, shared psychotic disorder, psychotic disorder due to a general medical condition, schizophreniform disorder, amenorrheic disorders such as desmenorrhea, obesity, epilepsy, primary movement disorders, spasticities, Scott's syndrome, Tourette's syndrome, palsys, amyolateral sclerosis (ALS), akinetic-rigid disorders, akinesias, dyskinesias, restless leg syndrome, movement disorders associated with Parkinson's disease or Huntington's disease, mastalgia syndromes, motion sickness, immune dysfunctions, generalized anxiety disorder, panic disorder, social phobia, agoraphobia, specific phobias, obsessive-compulsive disorder, post-traumatic stress disorder, emesis, depressive disorders, single episode depression, recurrent depression, child abuse induced depression, postpartum depression, cyclothymia, bipolar disorder, neurocardiac syncope, neurogenic syncope, hypersensitive Carotid sinus, neurovascular syndrome, arrythmias, addiction disorders involving addictions to behaviors, HIV-1 associated dementia, AIDS dementia complex, HIV encephalopathy, HIV related neuralgias, AIDS related neuralgias, epilepsy, attention deficit hyperactivity disorder, a somatoform disorder selected from the group consisting of somitization disorder, hypochondriasis, somatoform pain disorder and undifferentiated somatoform disorder, and somatic symptoms selected from the group consisting of loss of appetite, insomnia, interrupted sleep, early morning awakening, tired awakening, loss of libido, restlessness, fatigue, constipation, dyspepsia, heart palpitations, headache, neck pain, back pain, limb pain, joint pain, abdominal pain, dizziness, nausea, heartburn, nervousness, tremors, burning and tingling sensations, morning stiffness, abdominal pain, abdominal distention, gurgling, diarrhea, and the symptoms associated with generalized anxiety disorder, preferably emesis and depressive disorders such as major depression, dysthymic disorders or Depressive Disorders Not Otherwise Specified, comprising an amount of a compound according to Formulae I or II, or a pharmaceutically acceptable salt or solvate thereof, effective in antagonizing the effect of substance P at its receptor site, and a pharmaceutically acceptable carrier.

In another practice, the invention relates to a pharmaceutical composition for treating in a mammal a condition selected from the group consisting of sleep disorders, autism, pervasive development disorder, rheumatoid arthritis, osteoarthritis, fibromyalgia, human immunodeficiency virus (HIV) infections, dissociative disorders, anorexia, bulimia, ulcerative colitis, Crohn's disease, irritable bowel syndrome, functional abdominal pain, chronic fatigue syndrome, sudden infant death syndrome (SIDS), overactive bladder, chronic cystitis, chemotherapy induced cystitis, cough, angiotensin converting enzyme (ACE) induced cough, itch, hiccups, premenstrual syndrome, premenstrual dysphoric disorder, schizophrenia, schizoaffective disorder, delusional disorder, substance-induced psychotic disorder, brief psychotic disorder, shared psychotic disorder, psychotic disorder due to a general medical condition, schizophreniform disorder, amenorrheic disorders such as desmenorrhea, obesity, epilepsy, primary movement disorders, spasticities, Scott's syndrome, Tourette's syndrome, palsys, amyolateral sclerosis (ALS), akinetic-rigid disorders, akinesias, dyskinesias, restless leg syndrome, movement disorders associated with Parkinson's disease or Huntington's disease, mastalgia syndromes, motion sickness, immune dysfunctions, generalized anxiety disorder, panic disorder, social phobia, agoraphobia, specific phobias, obsessive-compulsive disorder, post-traumatic stress disorder, emesis, depressive disorders, single episode depression, recurrent depression, child abuse induced depression, postpartum depression, cyclothymia, bipolar disorder, neurocardiac syncope, neurogenic syncope, hypersensitive Carotid sinus, neurovascular syndrome, arrythmias, addiction disorders involving addictions to behaviors, HIV-1 associated dementia, AIDS dementia complex, HIV encephalopathy, HIV related neuralgias, AIDS related neuralgias, epilepsy, attention deficit hyperactivity disorder, a somatoform disorder selected from the group consisting of somitization disorder, hypochondriasis, somatoform pain disorder and undifferentiated somatoform disorder, and somatic symptoms selected from the group consisting of loss of appetite, insomnia, interrupted sleep, early morning awakening, tired awakening, loss of libido, restlessness, fatigue, constipation, dyspepsia, heart palpitations, headache, neck pain, back pain, limb pain, joint pain, abdominal pain, dizziness, nausea, heartburn, nervousness, tremors, burning and tingling sensations, morning stiffness, abdominal pain, abdominal distention, gurgling, diarrhea, and the symptoms associated with generalized anxiety disorder, preferably emesis and depressive disorders such as major depression, dysthymic disorders or Depressive Disorders Not Otherwise Specified, comprising an amount of a compound according to Formulae I or II, or a pharmaceutically acceptable salt or solvate thereof, effective in treating said condition, and a pharmaceutically acceptable carrier.

In another practice, the invention relates to a pharmaceutical composition for treating a condition in a mammal, the treatment or prevention of which is effected or facilitated by a decrease in substance P mediated neurotransmission, comprising an amount of a compound according to Formulae I or II, or a pharmaceutically acceptable salt or solvate thereof, effective in antagonizing the effect of substance P at its receptor site, and a pharmaceutically acceptable carrier.

In another practice, the invention relates to a pharmaceutical composition for treating a condition in a mammal, the treatment or prevention of which is effected or facilitated by a decrease in substance P mediated neurotransmission, comprising an amount of a compound according to Formulae I or II, or a pharmaceutically acceptable salt or solvate thereof, effective in treating said condition, and a pharmaceutically acceptable carrier.

In another practice, the invention relates to a method of antagonizing the effects of substance P in a mammal, comprising administering to said mammal a substance P antagonizing amount of a compound according to Formulae I or II, or a pharmaceutically acceptable salt or solvate thereof.

In another practice, the invention relates to a method of treating in a mammal a condition associated with the effect of excess substance P at its receptor site, comprising administering to said mammal an amount of a compound according to Formulae I or II, or a pharmaceutically acceptable salt or solvate thereof, effective in antagonizing the effect of substance P at its receptor site, wherein said mammal is in need of said treatment.

In another practice, the invention relates to a method of treating in a mammal a condition associated with the effect of excess substance P at its receptor site, comprising administering to said mammal an amount of a compound according to Formulae I or II, or a pharmaceutically acceptable salt or solvate thereof, effective in treating said condition, wherein said mammal is in need of said treatment.

In another practice, the invention relates to a method of treating in a mammal a condition selected from the group consisting of sleep disorders, autism, pervasive development disorder, rheumatoid arthritis, osteoarthritis, fibromyalgia, human immunodeficiency virus (HIV) infections, dissociative disorders, anorexia, bulimia, ulcerative colitis, Crohn's disease, irritable bowel syndrome, functional abdominal pain, chronic fatigue syndrome, sudden infant death syndrome (SIDS), overactive bladder, chronic cystitis, chemotherapy induced cystitis, cough, angiotensin converting enzyme (ACE) induced cough, itch, hiccups, premenstrual syndrome, premenstrual dysphoric disorder, schizophrenia, schizoaffective disorder, delusional disorder, substance-induced psychotic disorder, brief psychotic disorder, shared psychotic disorder, psychotic disorder due to a general medical condition, schizophreniform disorder, amenorrheic disorders such as desmenorrhea, obesity, epilepsy, primary movement disorders, spasticities, Scott's syndrome, Tourette's syndrome, palsys, amyolateral sclerosis (ALS), akinetic-rigid disorders, akinesias, dyskinesias, restless leg syndrome, movement disorders associated with Parkinson's disease or Huntington's disease, mastalgia syndromes, motion sickness, immune dysfunctions, generalized anxiety disorder, panic disorder, social phobia, agoraphobia, specific phobias, obsessive-compulsive disorder, post-traumatic stress disorder, emesis, depressive disorders, single episode depression, recurrent depression, child abuse induced depression, postpartum depression, dysthemia, cyclothymia, bipolar disorder, neurocardiac syncope, neurogenic syncope, hypersensitive Carotid sinus, neurovascular syndrome, arrythmias, addiction disorders involving addictions to behaviors, HIV-1 associated dementia, AIDS dementia complex, HIV encephalopathy, HIV related neuralgias, AIDS related neuralgias, epilepsy, attention deficit hyperactivity disorder, a somatoform disorder selected from the group consisting of somitization disorder, hypochondriasis, somatoform pain disorder and undifferentiated somatoform disorder, and somatic symptoms selected from the group consisting of loss of appetite, insomnia, interrupted sleep, early morning awakening, tired awakening, loss of libido, restlessness, fatigue, constipation, dyspepsia, heart palpitations, headache, neck pain, back pain, limb pain, joint pain, abdominal pain, dizziness, nausea, heartburn, nervousness, tremors, burning and tingling sensations, morning stiffness, abdominal pain, abdominal distention, gurgling, diarrhea, and the symptoms associated with generalized anxiety disorder, preferably emesis and depressive disorders such as major depression, dysthymic disorders or Depressive Disorders Not Otherwise Specified, comprising administering to said mammal an amount a compound according to Formulae I or II, or a pharmaceutically acceptable salt or solvate thereof, effective in antagonizing the effect of substance P at its receptor site, wherein said mammal is in need of said treatment.

In another practice, the invention relates to a method of treating in a mammal a condition selected from the group consisting of sleep disorders, autism, pervasive development disorder, rheumatoid arthritis, osteoarthritis, fibromyalgia, human immunodeficiency virus (HIV) infections, dissociative disorders, anorexia, bulimia, ulcerative colitis, Crohn's disease, irritable bowel syndrome, functional abdominal pain, chronic fatigue syndrome, sudden infant death syndrome (SIDS), overactive bladder, chronic cystitis, chemotherapy induced cystitis, cough, angiotensin converting enzyme (ACE) induced cough, itch, hiccups, premenstrual syndrome, premenstrual dysphoric disorder, schizophrenia, schizoaffective disorder, delusional disorder, substance-induced psychotic disorder, brief psychotic disorder, shared psychotic disorder, psychotic disorder due to a general medical condition, schizophreniform disorder, amenorrheic disorders such as desmenorrhea, obesity, epilepsy, primary movement disorders, spasticities, Scott's syndrome, Tourette's syndrome, palsys, amyolateral sclerosis (ALS), akinetic-rigid disorders, akinesias, dyskinesias, restless leg syndrome, movement disorders associated with Parkinson's disease or Huntington's disease, mastalgia syndromes, motion sickness, immune dysfunctions, generalized anxiety disorder, panic disorder, social phobia, agoraphobia, specific phobias, obsessive-compulsive disorder, post-traumatic stress disorder, major depression, single episode depression, recurrent depression, child abuse induced depression, postpartum depression, dysthemia, cyclothymia, bipolar disorder, neurocardiac syncope, neurogenic syncope, hypersensitive Carotid sinus, neurovascular syndrome, arrythmias, addiction disorders involving addictions to behaviors, HIV-1 associated dementia, AIDS dementia complex, HIV encephalopathy, HIV related neuralgias, AIDS related neuralgias, epilepsy, attention deficit hyperactivity disorder, a somatoform disorder selected from the group consisting of somitization disorder, hypochondriasis, somatoform pain disorder and undifferentiated somatoform disorder, and somatic symptoms selected from the group consisting of loss of appetite, insomnia, interrupted sleep, early morning awakening, tired awakening, loss of libido, restlessness, fatigue, constipation, dyspepsia, heart palpitations, headache, neck pain, back pain, limb pain, joint pain, abdominal pain, dizziness, nausea, heartburn, nervousness, tremors, burning and tingling sensations, morning stiffness, abdominal pain, abdominal distention, gurgling, diarrhea, and the symptoms associated with generalized anxiety disorder, comprising administering to said mammal an amount of a compound according to Formulae I or II, or a pharmaceutically acceptable salt or solvate thereof, effective in treating said condition, wherein said mammal is in need of said treatment.

In another practice, the invention relates to a method of treating a condition in a mammal, the treatment or prevention of which is effected or facilitated by a decrease in substance P mediated neurotransmission, comprising administering to said mammal an amount of a compound according to Formulae I or II, or a pharmaceutically acceptable salt or solvate thereof, effective in antagonizing the effect of substance P at its receptor site, wherein said mammal is in need, of said treatment.

In another practice, the invention relates to a method of treating a condition in a mammal, the treatment or prevention of which is effected or facilitated by a decrease in substance P mediated neurotransmission, comprising administering to said mammal an amount of a compound according to Formulae I or II, or a pharmaceutically acceptable salt or solvate thereof, effective in treating said condition, wherein said mammal is in need of said treatment.

In another aspect, the compound of the invention is used in an assay of NK-1 binding wherein said compound exhibits a Ki of about 5 nM or less, preferably 2 nM or less, more preferably about 0.1 nM or less.

DETAILED DESCRIPTION OF THE INVENTION

The present invention relates to a compound (that in various practices comprises piperidine, pyrrolidine, and diazepane derivatives) which is an antagonist of tachykinins, including substance P and is thus useful for the treatment of neurokinin-mediated conditions, among other things.

In a preferred embodiment, the compound of the invention has Formulae I or II, above, or a pharmaceutically acceptable salt or solvate thereof, e.g. acid addition salts, base addition salts, and prodrugs and solvates thereof. Without limitation, examples of pharmaceutically acceptable acid addition salts of the compounds of Formulae I or II are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malate, di-p-toluoyl tartaric acid, lactic acid, acetic acid, trifluoroacetic acid, and mandelic acid.

The compound of the invention can have optical centers and thus occur in different enantiomeric configurations. The invention includes all enantiomers, diastereomers, and other stereoisomers and optical isomers, as well as racemic and other mixtures thereof. For example, the compound of the invention includes (R) and (S) enantiomers and cis and trans isomers. The present invention further includes all radiolabelled forms of the compound of Formulae I or II. Preferred radiolabelled compounds are those wherein the radiolabels are selected from $^3$H, $^{11}$C, $^{14}$C, $^{18}$F, $^{123}$I and $^{125}$I. Such radiolabelled compounds are useful as research and diagnostic tools in metabolism pharmacokinetics studies and in binding assays in animals and man.

As appreciated by the artisan, the use of the formulae for the compound of the invention is a convenience; and the invention is understood to envision and embrace each and every species thereunder as though individually identified and set forth herein. Thus the present invention severally contemplates each species separately and any and all combinations and permutations of species falling within Formulae I or II.

In a preferred embodiment of the compound of Formula (I), $R^1$ and $R^2$ are each independently H, methyl, Cl or Br; and $R^3$ is phenyl or naphthyl, either one of which may be optionally substituted with 1 to 3 substituents independently selected from hydroxy, $C_{5-6}$ cycloalkoxy, benzo($C_{5-6}$)cycloalkoxy, $C_{1-2}$ alkylthio, tetrazole, or phenoxy, wherein said phenoxy is optionally substituted with 1 to 3 groups independently selected from Cl, Br, F, methoxy, ethoxy, cyano, methyl or ethyl.

Without limitation, representative compounds of Formula (I) contemplated by the invention include:

6-Methoxy-3-methyl-5-[(2-phenyl-pyrrolidin-3-ylamino)-methyl]-1,1a,3,7b-tetrahydro-3-aza-cyclopropa[a]naphthalen-2-one;

5-{[2-(3-Chloro-phenyl)-pyrrolidin-3-ylamino]-methyl}-6-methoxy-3-methyl-1,1a,3,7b-tetrahydro-3-aza-cyclopropa[a]naphthalen-2-one;

[2-(3-Chloro-phenyl)-pyrrolidin-3-yl]-(6-methoxy-3-trifluoromethyl-indan-5-ylmethyl)-amine;

(6-Methoxy-3-trifluoromethyl-indan-5-ylmethyl)-(2-phenyl-pyrrolidin-3-yl)-amine;

6-Methoxy-3-methyl-3-trifluoromethyl-indan-5-ylmethyl)-(2-phenyl-pyrrolidin-3-yl)-amine;

2-[(2-Phenyl-pyrrolidin-3-ylamino)-methyl]-phenol;

Dibenzofuran-2-ylmethyl-(2-phenyl-pyrrolidin-3-yl)-amine;

(6-Methoxy-2-methyl-benzothiazol-5-ylmethyl)-(2-phenyl-pyrrolidin-3-yl)-amine;

(6-Methoxy-2-phenyl-benzothiazol-7-ylmethyl)-(2-phenyl-pyrrolidin-3-yl)-amine;

[2-(3,4-Dichloro-phenoxy)-5-fluoro-benzyl]-(2-phenyl-pyrrolidin-3-yl)-amine;

[2-Methoxy-5-(5-trifluoromethyl-tetrazol-1-yl )-benzyl]-(2-phenyl-pyrrolidin-3-yl)-amine;

2-[(2-Phenyl-pyrrolidin-3-ylamino)-methyl]-4-(5-trifluoromethyl-tetrazol-1-yl)-phenol;

(4-Phenoxy-benzyl)-(2-phenyl-pyrrolidin-3-yl)-amine;

[3-(4-Methoxy-phenoxy)-benzyl]-(2-phenyl-pyrrolidin-3-yl)-amine;

(6-Methoxy-1-methyl-1-trifluoromethyl-isochroman-7-ylmethyl)-(2-phenyl-pyrrolidin-3-yl)-amine;

2-Chloro-6-{3-[(2-phenyl-pyrrolidin-3-ylamino)-methyl]-phenoxy}-benzonitrile;

cis-5-{[2-(3-Chloro-phenyl)-pyrrolidin-3-ylamino]-methyl}-6-methoxy-3-methyl-1,1a,3,7b-tetrahydro-3-aza-cyclopropa[a]naphthalen-2-one;

cis-6-Methoxy-1-methyl-7-[(2-phenyl-pyrrolidin-3-ylamino)-methyl]-3,4-dihydro-1H-[1,5]naphthyridin-2-one;

trans-5-{[2-(4-Fluoro-2-methyl-phenyl)-pyrrolidin-3-ylamino]-methyl}-6-methoxy-3-methyl-1,1a,3,7b-tetrahydro-3-aza-cyclopropa[a]naphthalen-2-one;

(2,2-Dimethyl-chroman-6-ylmethyl)-(2-phenyl-pyrrolidin-3-yl)-amine;

[3-(4-Ethyl-phenoxy)-benzyl]-(2-phenyl-pyrrolidin-3-yl)-amine;

and pharmaceutically acceptable salts or solvates thereof.

In a preferred embodiment of the compound of Formula (II): $R^1$ is H or F; $R^2$ is H or $CH_3$; $R^3$ is phenyl or naphthyl, either one of which may be optionally substituted with 1 to 3 of the following groups: Cl, F, Br, $C_{1-4}$ alkyl, $C_{1-3}$ fluoroalkyl, $C_{1-3}$ alkoxy, $C_{1-3}$ fluoroalkoxy, or phenyl. In a more preferred embodiment of the compound of Formula (II) said $C_{1-4}$ alkyl is methyl, ethyl, propyl or t-butyl; said $C_{1-3}$ fluoroalkyl is trifluoromethyl; said $C_{1-3}$ alkoxy is methoxy, ethoxy or propoxy; and said $C_{1-3}$ fluoroalkoxy is difluoromethoxy or trifluoromethoxy.

Without limitation, representative compounds of Formula (II) contemplated by the invention include:

cis-(2-Methoxy-benzyl)-(2-phenyl-pyrrolidin-3-yl)-amine;

cis-(3-Chloro-benzyl)-(2-phenyl-pyrrolidin-3-yl)-amine;

cis-(6'-Methoxy-3,4,5,6-tetrahydro-2H-[1,3]bipyridinyl-5'-ylmethyl)-(2-phenyl-pyrrolidin-3-yl)-amine dihydrochloride;

cis-(5-Chloro-2-ethoxy-pyridin-3-ylmethyl)-(2-phenyl-pyrrolidin-3-yl)-amine;

cis-(2-Phenyl-pyrrolidin-3-yl)-(4-propoxy-benzyl)-amine;

cis-(2-Bromo-benzyl)-(2-phenyl-pyrrolidin-3-yl)-amine;

cis-(5-Methyl-furan-2-ylmethyl)-(2-phenyl-pyrrolidin-3-yl)-amine;
cis-(3-Methyl-thiophen-2-ylmethyl)-(2-phenyl-pyrrolidin-3-yl)-amine;
cis-(5-Ethyl-furan-2-ylmethyl)-(2-phenyl-pyrrolidin-3-yl)-amine;
cis-(2-Chloro-quinolin-3-ylmethyl)-(2-phenyl-pyrrolidin-3-yl)-amine;
cis-(3-Methyl-benzo[b]thiophen-2-ylmethyl)-(2-phenyl-pyrrolidin-3-yl)-amine;
cis-Benzofuran-2-ylmethyl-(2-phenyl-pyrrolidin-3-yl)-amine;
trans-(2-methoxy-benzyl)-(2-phenyl-pyrrolidin-3-yl)-amine;
trans-(3-Chloro-benzyl)-(2-phenyl-pyrrolidin-3-yl)-amine;
trans-(3,5-Bis-trifluoromethyl-benzyl)-(2-phenyl-pyrrolidin-3-yl)-amine;
(3,5-Bis-trifluoromethyl-benzyl)-(2-phenyl-pyrrolidin-3-yl)-amine;
cis-Benzyl-(2-phenyl-pyrrolidin-3-yl)-amine;
tran-Benzyl-(2-phenyl-pyrrolidin-3-yl)-amine;
cis-Benzyl-[2-(3-chloro-phenyl)-pyrrolidin-3-yl]-amine;
cis-[2-(3-Chloro-phenyl)-pyrrolidin-3-yl]-(2-methoxy-benzyl)-amine;
cis-[2-(3-Chloro-phenyl)-pyrrolidin-3-yl]-(2-difluoromethoxy-benzyl)-amine;
cis-(5-tert-Butyl-2-methoxy-benzyl)-[2-(3-chloro-phenyl)-pyrrolidin-3-yl]-amine;
cis-[2-(3-Chloro-phenyl)-pyrrolidin-3-yl]-(2-methoxy-5-trifluoromethoxy-benzyl)-amine;
cis-[5-(2,2-Difluoro-propyl)-2-methoxy-benzyl]-(2-phenyl-pyrrolidin-3-yl)-amine;
cis-[2-Methoxy-5-(2,2,2-trifluoro-1,1-dimethyl-ethyl)-benzyl]-(2-phenyl-pyrrolidin-3-yl)-amine;
cis-(2-Difluoromethoxy-benzyl)-(2-phenyl-pyrrolidin-3-yl)-amine;
cis-(5-tert-Butyl-2-methoxy-benzyl)-(2-phenyl-pyrrolidin-3-yl)-amine;
cis-(5-tert-Butyl-2-methoxy-benzyl)-(2-phenyl-pyrrolidin-3-yl)-amine;
cis-(5-tert-Butyl-2-methoxy-benzyl)-(2-phenyl-pyrrolidin-3-yl)-amine;
cis-(2-isopropoxy-5-trifluoromethoxy-benzyl)-(2-phenyl-pyrrolidin-3-yl)-amine;
cis-(2,6-Dichloro-4-methoxy-benzyl)-(2-phenyl-pyrrolidin-3-yl)-amine;
cis-(2-Methoxy-5-trifluoromethoxy-benzyl)-(2-phenyl-pyrrolidin-3-yl)-amine;
cis-(2-Phenyl-pyrrolidin-3-yl)-(2,3,5-trichloro-benzyl)-amine;
cis-(5-Chloro-2-methoxy-benzyl)-(2-phenyl-pyrrolidin-3-yl)-amine;
cis-(2,3-Difluoro-benzyl)-(2-phenyl-pyrrolidin-3-yl)-amine;
cis-(2,5-Difluoro-benzyl)-(2-phenyl-pyrrolidin-3-yl)-amine;
cis-(2-Ethoxy-naphthalen-1-ylmethyl)-(2-phenyl-pyrrolidin-3-yl)-amine;
cis-(2-Phenyl-pyrrolidin-3-yl-(4-propoxy-benzyl)-amine;
cis-(4-Ethyl-benzyl)-(2-phenyl-pyrrolidin-3-yl)-amine;
cis-(3-Ethoxy-4-methoxy-benzyl)-(2-phenyl-pyrrolidin-3-yl)-amine;
cis-(2-Phenyl-pyrrolidin-3-yl)-(2,3,6-trifluoro-benzyl)-amine;
cis-(3-Fluoro-2-methyl-benzyl)-(2-phenyl-pyrrolidin-3-yl)-amine;
cis-(2-Chloro-3,4-dimethoxy-benzyl)-(2-phenyl-pyrrolidin-3-yl)-amine;
cis-(2-Phenyl-pyrrolidin-3-yl)-thiophen-2-ylmethyl-amine;
cis-5-Bromo-2-methoxy-benzyl)-(2-phenyl-pyrrolidin-3-yl)-amine;
cis-(2-Bromo-4,5-dimethoxy-benzyl)-(2-phenyl-pyrrolidin-3-yl)-amine;
cis-(2,3-Dichloro-benzyl)-(2-phenyl-pyrrolidin-3-yl)-amine;
cis-(2-Chloro-4-fluoro-benzyl)-(2-phenyl-pyrrolidin-3-yl)-amine;
cis-(2-Chloro-benzyl)-(2-phenyl-pyrrolidin-3-yl)-amine;
cis-(6-Bromo-2,3-dimethoxy-benzyl)-(2-phenyl-pyrrolidin-3-yl)-amine; and
cis-(2-Bromo-3,6-dimethoxy-benzyl)-(2-phenyl-pyrrolidin-3-yl)-amine;
and pharmaceutically acceptable salts or solvates thereof.

The present invention also relates to a method of treating one or more disorders or conditions such as sleep disorders (e.g., sleep apnea, insomnia, somnambulism, sleep deprivation, REM sleep disorders, hypersomnia, parasomnias, sleep-wake cycle disorders, narcolepsy, sleep disorders associated with shift work or irregular work schedules, and other sleep disorders); pervasive development disorder; rheumatoid arthritis; osteoarthritis; fibromyalgia; human immunodeficiency virus (HIV) infections; dissociative disorders such as body dysmorphic disorders; eating disorder such as anorexia and bulimia, ulcerative colitis; Crohn's disease; irritable bowel syndrome; functional abdominal pain; chronic fatigue syndrome; sudden infant death syndrome (SIDS); overactive bladder; chronic cystitis; chemotherapy induced cystitis; cough, angiotensin converting enzyme (ACE) induced cough; itch; hiccups; premenstrual syndrome: premenstrual dysphoric disorder; schizophrenia; schizoaffective disorder; delusional disorder; substance-induced psychotic disorder; brief psychotic disorder; shared psychotic disorder; psychotic disorder due to a general medical condition; schizophreniform disorder; amenorrheic disorders such as desmenorrhea; obesity; epilepsy: movement disorders such as primary movement disorders, spasticities, Scott's syndrome, Tourette's syndrome, palsys (e.g., Bell's palsy, cerebral palsy, birth palsy, brachial palsy, wasting palsy, ischemic palsy, progressive bulbar palsy and other palsys), amyolateral sclerosis (ALS), akinetic-rigid disorders, akinesias, dyskinesias (e.g., familial paroxysmal dyskinesia, tardive dyskinesia, tremor, chorea, myoclonus, tics and other dyskinesias) restless leg syndrome and movement disorders associated with Parkinson's disease or Huntington's disease; mastalgia syndromes; motion sickness; immune dysfunctions (e.g., stress induced immune dysfunctions such as idiopathic immune dysfunctions, post infection immune dysfunctions, post lumpectomy immune dysfunctions, porcine stress syndrome, bovine shipping fever, equine paroxysmal fibrillation, confinement dysfunction in chicken, sheering stress in sheep, and human-animal interaction stress in dogs); generalized anxiety disorder; panic disorder; phobias, including social phobia, agoraphobia, and specific phobias; obsessive-compulsive disorder; emesis; post-traumatic stress disorder; depressive disorders including major depressive disorder, single episode depression, recurrent depression, child abuse induced depression, post-partum depression and dysthymia; cyclothymia; bipolar disorder; neurocardiac disorders such as neurocardiac syncope, neurogenic syncope, hypersensitive Carotid sinus, neurovascular syndrome and arrythmias including arrythmias secondary to gastrointestinal disturbances; addiction disorders involving addictions to behaviors (e.g., addictions to gambling and other addictive behaviors); HIV-1 associated dementia; HIV encephalopathy; AIDS dementia complex (ADC); HIV related neuralgias; AIDS related neuralgias; epilepsy; and attention deficit hyperactivity disorder in a mammal, comprising administering to said mammal an amount of a compound of Formulae I or II, or a pharmaceutically acceptable salt or solvate thereof, that is effective in antagonizing the effect of substance P at its receptor site, wherein said mammal is in need of said treatment.

Other more specific methods of this invention include any of the above methods wherein the disorder or condition that is being treated is selected from movement disorders such as primary movement disorders, spasticities, Scott's syndrome, Tourette's syndrome, palsys (e.g., Bell's palsy, cerebral palsy, birth palsy, brachial palsy, wasting palsy, ischemic palsy, progressive bulbar palsy and other palsys), amyolateral sclerosis (ALS), akinetic-rigid disorders, akinesias, dyskinesias (e.g., familial paroxysmal dyskinesia, tardive dyskinesia, tremor, chorea, myoclonus, tics and other dyskinesias) restless leg syndrome and movement disorders associated with Parkinson's disease or Huntington's disease.

Other more specific methods of this invention include the above methods wherein the disorder or condition that is being treated is major depressive disorder.

Other more specific methods of this invention include the above methods wherein the disorder or condition that is being treated is major depressive disorder, and wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is somatic major depressive disorder.

Other more specific methods of this invention include the above methods wherein the disorder or condition that is being treated is somatic major depressive disorder, and wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is irritable bowel syndrome.

Other more specific methods of this invention include the above methods wherein the disorder or condition that is being treated is an HIV infection.

Other more specific methods of this invention include the above methods wherein the disorder or condition that is being treated is selected from HIV-1 associated dementia, AIDS dementia complex (ADC), HIV encephalopathy, and HIV related neuralgias.

Other more specific methods of this invention include the above methods wherein the disorder or condition that is being is immune dysfunctions (e.g., stress induced immune dysfunctions such as idiopathic immune dysfunctions, post infection immune dysfunctions, post lumpectomy immune dysfunctions, porcine stress syndrome, bovine shipping fever, equine paroxysmal fibrillation, confinement dysfunction in chicken, sheering stress in sheep, or human-animal interaction stress in dogs).

Other more specific methods of this invention include the above methods wherein the disorder or condition that is being treated is neurocardiac disorders such as neurocardiac syncope, neurogenic syncope, hypersensitive Carotid sinus, neurovascular syndrome or arrythmias including arrythmias secondary to gastrointestinal disturbances.

Other more specific methods of this invention include the above methods wherein the disorder or condition that is being treated is major depression, single episode depression, recurrent depression, child abuse induced depression, postpartum depression, dysthymia, cyclothymia or bipolar disorder.

Other more specific methods of this invention include the above methods wherein the disorder or condition that is being treated is major depression, single episode depression, recurrent depression, child abuse induced depression, postpartum depression, dysthymia, cyclothymia or bipolar disorder, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is body dysmorphic disorders and eating disorders such as anorexia and bulimia.

Other more specific methods of this invention include the above methods wherein the disorder or condition that is being treated is schizophrenia, schizoaffective disorder, delusional disorder, substance-induced psychotic disorder, brief psychotic disorder, shared psychotic disorder, psychotic disorder due to a general medical condition, or schizophreniform disorder.

Other more specific methods of this invention include the above methods wherein the disorder or condition that is being treated is premenstrual syndrome, premenstrual dysphoric disorder, and amenorrheic disorders such as desmenorrhea.

Other more specific methods of this invention include the above methods wherein the disorder or condition that is being treated is premenstrual syndrome, premenstrual dysphoric disorder, or amenorrheic disorders such as desmenorrhea, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is Crohn's disease, irritable bowel syndrome or functional abdominal pain.

Other more specific methods of this invention include the above methods wherein the disorder or condition that is being treated is selected from autism, pervasive development disorder, or attention deficit hyperactivity disorder.

Other more specific method of this invention include the above methods wherein the disorder or condition that is being treated is selected from chronic fatigue syndrome, sudden infant death syndrome (SIDS), obesity, or epilepsy.

Other more specific methods of this invention include the above methods wherein the disorder or condition that is being treated is generalized anxiety disorder, panic disorder, obsessive-compulsive disorder, post-traumatic stress disorder, or phobias, including social phobia, agoraphobia, and specific phobias.

Other more specific methods of this invention include the above methods wherein the disorder or condition that is being treated is generalized anxiety disorder, panic disorder, obsessive-compulsive disorder, post-traumatic stress disorder, and phobias, including social phobia, agoraphobia, or specific phobias, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is cough, angiotensin converting enzyme (ACE) induced cough, itch, or hiccups.

Other more specific methods of this invention include the above methods wherein the disorder or condition that is being treated is overactive bladder; chronic cystitis or chemotherapy induced cystitis.

Other more specific methods of this invention include the above methods wherein the disorder or condition that is being treated is attention deficit hyperactivity disorder.

Other more specific methods of this invention include the above methods wherein the disorder or condition that is being treated is a sleep disorder (e.g., sleep apnea, insomnia, somnambulism, sleep deprivation, REM sleep disorders, hypersomnia, parasomnias, sleep-wake cycle disorders, narcolepsy, sleep disorders associated with shift work or irregular work schedules, and other sleep disorders).

The present invention also relates to a method of treating a disorder or condition selected from the group consisting of pain resulting from soft tissue and peripheral damage, such as acute trauma; postherpetic neuralgia, trigeminal neuralgia, segmental or intercostal neuralgia and other neuralgias; pain associated with osteoarthritis and rheumatoid arthritis; musculo-skeletal pain, such as pain experienced after trauma; spinal pain, dental pain, myofascial pain syndromes, episiotomy pain, and pain resulting from burns; deep and visceral pain, such as heart pain, muscle pain, eye pain, orofacial pain, for example, odontalgia, abdominal pain, gynaecological pain, for example, dysmenorrhoea, labour pain and pain associated with endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, neuropathic lower back pain, HIV related neuropathic pain, diabetic neuropathic pain, and arachnoiditis; neuropathic and non-neuropathic pain associated with carcinoma, often referred to as cancer pain; central nervous system pain, such as pain due to spinal cord or brain stem damage; lower back pain; sciatica; phantom limb pain, headache, including migraine and other vascular headaches, acute or chronic tension headache, cluster headache, temperomandibular pain and maxillary sinus pain; pain resulting from ankylosing spondylitis and gout; pain caused by increased bladder contractions; post operative pain; scar pain; and chronic non-neuropathic pain such as pain associated with fibromyalgia, HIV, rheumatoid and osteoarthritis, anthralgia and myalgia, sprains, strains and trauma such as broken bones; and post surgical pain in a mammal, comprising administering to said mammal an amount of a compound of Formula I as defined above, or a pharmaceutically acceptable salt or solvate thereof, that is effective in treating such disorder or condition.

The present invention also relates to a method of treating a disorder or condition selected from the group consisting of pain resulting from soft tissue and peripheral damage, such as acute trauma; postherpetic neuralgia, trigeminal neuralgia, segmental or intercostal neuralgia and other neuralgias; pain associated with osteoarthritis and rheumatoid arthritis; musculo-skeletal pain, such as pain experienced after trauma; spinal pain, dental pain, myofascial pain syndromes, episiotomy pain, and pain resulting from burns; deep and visceral pain, such as heart pain, muscle pain, eye pain, orofacial pain, for example, odontalgia, abdominal pain, gynaecological pain, for example, dysmenorrhoea, labour pain and pain associated with endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, neuropathic lower back pain, HIV related neuropathic pain, diabetic neuropathic pain, and arachnoiditis; neuropathic and non-neuropathic pain associated with carcinoma, often referred to as cancer pain; central nervous system pain, such as pain due to spinal cord or brain stem damage; lower back pain; sciatica; phantom limb pain, headache, including migraine and other vascular headaches, acute or chronic tension headache, cluster headache, temperomandibular pain and maxillary sinus pain; pain resulting from ankylosing spondylitis and gout; pain caused by increased bladder contractions; post operative pain; scar pain; and chronic non-neuropathic pain such as pain associated with fibromyalgia, HIV, rheumatoid and osteoarthritis, anthralgia and myalgia, sprains, strains and trauma such as broken bones; and post surgical pain in a mammal, comprising administering to said mammal an amount of a compound of Formula I, as defined above, or a pharmaceutically acceptable salt thereof, that is effective in antagonizing the effect of substance P at its receptor site.

Other more specific methods of this invention include the above methods wherein the disorder or condition that is being treated is neuropathic pain.

Other more specific methods of this invention include the above methods wherein the disorder or condition that is being treated is HIV related neuralgia.

Other more specific methods of this invention include the above methods wherein the disorder or condition that is being treated is pain associated with fibromyalgia.

Other more specific methods of this invention include the above methods wherein the disorder or condition that is being treated is neuropathic lower back pain, HIV related neuropathic pain, diabetic neuropathic pain, arachnoiditis or neuropathic and non-neuropathic pain associated with carcinoma.

Unless otherwise indicated, the following terms and related variations of same as used herein representatively have the meanings ascribed:

"Halogen" and "halo" and the like includes fluoro, chloro, bromo and iodo.

"Alkoxy" is —O—C$_{(1-6)}$alkyl.

"Alkyl" including as appears in any terms such as "alkoxy", "haloalkyl" and "alkyoxycarbonyl," or in any substituents such as —O—(C$_1$-C$_6$)alkyl, —O—(C$_1$-C$_6$)alkyl, or —(C$_1$-C$_6$)alkyl-C(O)—R$^6$ includes saturated monovalent hydrocarbon radicals having straight or branched moieties. Examples of alkyl groups include, but are not limited to, methyl, ethyl, n-propyl, isopropyl, and t-butyl.

"Haloalkyl" includes an "alkyl" as defined hereinabove wherein at lease one hydrogen radical is substituted with a "halogen" as defined above.

"Haloalkoxy" includes an "alkoxy" as defined hereinabove wherein at lease one hydrogen radical is substituted with a "halogen" as defined above.

"Cycloalkyl" includes non-aromatic saturated cyclic alkyl moieties wherein alkyl is as defined above. The cycloalkyl can be optionally substituted with one or more "ring system substituents" which can be the same or different, and are as defined above. Examples of cycloalkyl include, but are not limited to, cyclopropyl, cyclobutyl, cyclopentyl, cyclohexyl, and cycloheptyl; and bicycloalkyl and tricycloalkyl groups that are non-aromatic saturated carbocyclic groups consisting of two or three rings respectively, wherein said rings share at least one carbon atom. For purposes of the present invention, and unless otherwise indicated, bicycloalkyl groups include spiro groups and fused ring groups. Examples of bicycloalkyl groups include, but are not limited to, bicyclo-[3.1.0]-hexyl, bicyclo-2.2.1]-hept-1-yl, norbornyl, spiro[4.5]decyl, spiro[4.4]nonyl, spiro[4.3]octyl, and spiro[4.2]heptyl. An example of a tricycloalkyl group is adamantanyl. Cycloalkyl groups also include groups that are substituted with one or more oxo moieties. Examples of such groups with oxo moieties are oxocyclopentyl and oxocyclohexyl.

"Aryl" refers to monocyclic and multicyclic groups which includes an organic radical derived from an aromatic hydrocarbon by removal of one hydrogen, such as phenyl, naphthyl, tetrahydonaphthyhl, indenyl, indanyl, and fluorenyl; and fused ring groups wherein at least one ring is aromatic. The aryl groups can be optionally substituted with one or more "ring system substituents" which can be the same or different, and are as defined above. The aryl groups of this invention can also include ring systems substituted with one or more oxo moieties.

"Aryloxy" refers to —O-aryl groups wherein "aryl" is as defined above.

The foregoing groups, as derived from the compounds listed above, can be C-attached or N-attached where such is possible. For instance, a group derived from pyrrole can be pyrrol-1-yl (N-attached) or pyrrol-3-yl (C-attached). The terms referring to the groups also encompass all possible tautomers.

"Solvates" of the compounds of the invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$.

"Treatment" and "treating" refers to reversing, alleviating, inhibiting the progress of, or preventing the disorder or condition to which such term applies, or one or more symptoms of such condition or disorder. As used herein, the term also encompasses, depending on the condition of the patient, preventing the disorder, including preventing onset of the disorder or of any symptoms associated therewith, as well as reducing the severity of the disorder or any of its symptoms prior to onset. "Treating" as used herein refers also to preventing a recurrence of a disorder. The term "treatment", as used herein, refers to the act of treating, as "treating" is defined immediately above.

"Mammal" refers to any member of the class "Mammalia", including, but not limited to, humans, dogs, and cats.

NK-mediated Conditions

The present invention also relates to a method of treating one or more disorders or conditions such as sleep disorders (e.g., sleep apnea, insomnia, somnambulism, sleep deprivation, REM sleep disorders, hypersomnia, parasomnias, sleep-wake cycle disorders, narcolepsy, sleep disorders associated with shift work or irregular work schedules, and other sleep disorders); pervasive development disorder; rheumatoid arthritis; osteoarthritis; fibromyalgia; human immunodeficiency virus (HIV) infections; dissociative disorders such as body dysmorphic disorders; eating disorder such as anorexia and bulimia, ulcerative colitis; Crohn's disease; irritable bowel syndrome; functional abdominal pain; chronic fatigue syndrome; sudden infant death syndrome (SIDS); overactive bladder; chronic cystitis; chemotherapy induced cystitis; cough, angiotensin converting enzyme (ACE) induced cough; itch; hiccups; premenstrual syndrome: premenstrual dysphoric disorder; schizophrenia; schizoaffective disorder; delusional disorder; substance-induced psychotic disorder; brief psychotic disorder; shared psychotic disorder; psychotic disorder due to a general medical condition; schizophreniform disorder; amenorrheic disorders such as desmenorrhea; obesity; epilepsy: movement disorders such as primary movement disorders, spasticities, Scott's syndrome, Tourette's syndrome, palsys (e.g., Bell's palsy, cerebral palsy, birth palsy, brachial palsy, wasting palsy, ischemic palsy, progressive bulbar palsy and other palsys), amyolateral sclerosis (ALS), akinetic-rigid disorders, akinesias, dyskinesias (e.g., familial paroxysmal dyskinesia, tardive dyskinesia, tremor, chorea, myoclonus, tics and other dyskinesias) restless leg syndrome and movement disorders associated with Parkinson's disease or Huntington's disease; mastalgia syndromes; motion sickness; immune dysfunctions (e.g., stress induced immune dysfunctions such as idiopathic immune dysfunctions, post infection immune dysfunctions, post lumpectomy immune dysfunctions, porcine stress syndrome, bovine shipping fever, equine paroxysmal fibrillation, confinement dysfunction in chicken, sheering stress in sheep, and human-animal interaction stress in dogs; generalized anxiety disorder; panic disorder; phobias, including social phobia, agoraphobia, and specific phobias; obsessive-compulsive disorder; post-traumatic stress disorder; depression including major depressive disorder, single episode depression, recurrent depression, child abuse induced depression, postpartum depression and dysthymia; cyclothymia; bipolar disorder; neurocardiac disorders such as neurocardiac syncope, neurogenic syncope, hypersensitive Carotid sinus, neurovascular syndrome and arrythmias including arrythmias secondary to gastrointestinal disturbances; addiction disorders involving addictions to behaviors (e.g., addictions to gambling and other addictive behaviors); HIV-1 associated dementia; HIV encephalopathy; AIDS dementia complex (ADC); HIV related neuralgias; AIDS related neuralgias; epilepsy; and attention deficit hyperactivity disorder in a mammal, comprising administering to said mammal an amount of a compound of Formulae I or II, as defined above, or a pharmaceutically acceptable salt thereof, that is effective in antagonizing the effect of substance P at its receptor site.

Other more specific methods of this invention include any of the above methods wherein the disorder or condition that is being treated is selected from movement disorders such as primary movement disorders, spasticities, Scott's syndrome, Tourette's syndrome, palsys (e.g., Bell's palsy, cerebral palsy, birth palsy, brachial palsy, wasting palsy, ischemic palsy, progressive bulbar palsy and other palsys), amyolateral sclerosis (ALS), akinetic-rigid disorders, akinesias, dyskinesias (e.g., familial paroxysmal dyskinesia, tardive dyskinesia, tremor, chorea, myoclonus, tics and other dyskinesias) restless leg syndrome and movement disorders associated with Parkinson's disease or Huntington's disease.

Other more specific methods of this invention include the above methods wherein the disorder or condition that is being treated is major depressive disorder.

Other more specific methods of this invention include the above methods wherein the disorder or condition that is being treated is major depressive disorder, and wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is somatic major depressive disorder.

Other more specific methods of this invention include the above methods wherein the disorder or condition that is being treated is somatic major depressive disorder, and wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is irritable bowel syndrome.

Other more specific methods of this invention include the above methods wherein the disorder or condition that is being treated is an HIV infection.

Other more specific methods of this invention include the above methods wherein the disorder or condition that is being treated is selected from HIV-1 associated dementia, AIDS dementia complex (ADC), HIV encephalopathy, and HIV related neuralgias.

Other more specific methods of this invention include the above methods wherein the disorder or condition that is being is immune dysfunctions (e.g., stress induced immune dysfunctions such as idiopathic immune dysfunctions, post infection immune dysfunctions, post lumpectomy immune dysfunctions, porcine stress syndrome, bovine shipping fever, equine paroxysmal fibrillation, confinement dysfunction in chicken, sheering stress in sheep, or human-animal interaction stress in dogs).

Other more specific methods of this invention include the above methods wherein the disorder or condition that is being treated is neurocardiac disorders such as neurocardiac syncope, neurogenic syncope, hypersensitive Carotid sinus, neurovascular syndrome or arrythmias including arrythmias secondary to gastrointestinal disturbances.

Other more specific methods of this invention include the above methods wherein the disorder or condition that is being treated is major depression, single episode depression, recurrent depression, child abuse induced depression, postpartum depression, dysthymia, cyclothymia or bipolar disorder.

Other more specific methods of this invention include the above methods wherein the disorder or condition that is being treated is major depression, single episode depression, recurrent depression, child abuse induced depression, postpartum depression, dysthymia, cyclothymia or bipolar disorder, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is body dysmorphic disorders and eating disorders such as anorexia and bulimia.

Other more specific methods of this invention include the above methods wherein the disorder or condition that is being treated is schizophrenia, schizoaffective disorder, delusional disorder, substance-induced psychotic disorder, brief psychotic disorder, shared psychotic disorder, psychotic disorder due to a general medical condition, or schizophreniform disorder.

Other more specific methods of this invention include the above methods wherein the disorder or condition that is being treated is premenstrual syndrome, premenstrual dysphoric disorder, and amenorrheic disorders such as desmenorrhea.

Other more specific methods of this invention include the above methods wherein the disorder or condition that is being treated is premenstrual syndrome, premenstrual dysphoric disorder, or amenorrheic disorders such as desmenorrhea, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is Crohn's disease, irritable bowel syndrome or functional abdominal pain.

Other more specific methods of this invention include the above methods wherein the disorder or condition that is being treated is selected from autism, pervasive development disorder, or attention deficit hyperactivity disorder.

Other more specific method of this invention include the above methods wherein the disorder or condition that is being treated is selected from chronic fatigue syndrome, sudden infant death syndrome (SIDS), obesity, or epilepsy.

Other more specific methods of this invention include the above methods wherein the disorder or condition that is being treated is generalized anxiety disorder, panic disorder, obsessive-compulsive disorder, post-traumatic stress disorder, or phobias, including social phobia, agoraphobia, and specific phobias.

Other more specific methods of this invention include the above methods wherein the disorder or condition that is being treated is generalized anxiety disorder, panic disorder, obsessive-compulsive disorder, post-traumatic stress disorder, and phobias, including social phobia, agoraphobia, or specific phobias, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is cough, angiotensin converting enzyme (ACE) induced cough, itch, or hiccups.

Other more specific methods of this invention include the above methods wherein the disorder or condition that is being treated is overactive bladder; chronic cystitis or chemotherapy induced cystitis.

Other more specific methods of this invention include the above methods wherein the disorder or condition that is being treated is attention deficit hyperactivity disorder.

Other more specific methods of this invention include the above methods wherein the disorder or condition that is being treated is a sleep disorder (e.g., sleep apnea, insomnia, somnambulism, sleep deprivation, REM sleep disorders, hypersomnia, parasomnias, sleep-wake cycle disorders, narcolepsy, sleep disorders associated with shift work or irregular work schedules, and other sleep disorders).

Other more specific methods of this invention include the above methods wherein the disorder or condition that is being treated is neuropathic pain.

Other more specific methods of this invention include the above methods wherein the disorder or condition that is being treated is HIV related neuralgia.

Other more specific methods of this invention include the above methods wherein the disorder or condition that is being treated is pain associated with fibromyalgia.

Other more specific methods of this invention include the above methods wherein the disorder or condition that is being treated is neuropathic lower back pain, HIV related neuropathic pain, diabetic neuropathic pain, arachnoiditis or neuropathic and non-neuropathic pain associated with carcinoma.

Specific preferred methods of this invention include the above methods wherein the compound of Formula I or II that is employed in such method is one or more of the following NK1 antagonists:

cis-(2-Methoxy-benzyl)-(2-phenyl-pyrrolidin-3-yl)-amine dihydrochloride cis-(3,5-Bis-trifluoromethyl-benzyl)-(2-phenyl-pyrrolidin-3-yl)-amine dihydrochloride cis-Benzyl-(2-phenyl-pyrrolidin-3-yl)-amine dihydrobromide cis-(3-Chloro-benzyl)-(2-phenyl-pyrrolidin-3-yl)-amine dihydrobromide cis-6-Methoxy-3-methyl-5-[(2-phenyl-pyrrolidin-3-ylamino)-methyl]-1,1a,3,7b-tetrahydro-3-aza-cyclopropa[a]naphthalen-2-one dihydrochloride cis-Benzyl-[2-(3-chloro-phenyl)-pyrrolidin-3-yl]-amine dihydrobromide cis-[2-(3-Chloro-phenyl)-pyrrolidin-3-yl]-(2-methoxy-benzyl)-amine dihydrobromide cis-[2-(3-Chloro-phenyl)-pyrrolidin-3-yl]-(2-difluoromethoxy-benzyl)-amine dihydrochloride cis-5-{[2-(3-Chloro-phenyl)-pyrrolidin-3-ylamino]-methyl}-6-methoxy-3-methyl-1,1a,3,7b-tetrahydro-3-aza-cyclopropa[a]naphthalen-2-one dihydrobromide cis-(5-tert-butyl-2-methoxy-benzyl)-[2-(3-chloro-phenyl)-pyrrolidin-3-yl]-amine dihydrochloride cis-[2-(3-Chloro-phenyl)-pyrrolidin-3-yl]-(2-methoxy-5-trifluoromethoxy-benzyl)-amine dihydrochloride cis-[2-(3-Chloro-phenyl)-pyrrolidin-3-yl]-(6-methoxy-3-trifluoromethyl-indan-5-ylmethyl)-amine dihydrochloride cis-(6-Methoxy-3-trifluoromethyl-indan-5-ylmethyl)-(2-phenyl-pyrrolidin-3-yl)-amine dihydrochloride cis-[5-(2,2-Difluoro-propyl)-2-methoxy-benzyl]-(2-phenyl-pyrrolidin-3-yl)-amine dihydrochloride cis-[2-Methoxy-5-(2,2,2-trifluoro-1,1-dimethyl-ethyl)-benzyl]-(2-phenyl-pyrrolidin-3-yl)-amine dihydrochloride cis-(2-Difluoromethoxy-benzyl)-(2-phenyl-pyrrolidin-3-yl)-amine dihydrochloride cis-(5-tert-Butyl-2-methoxy-benzyl)-(2-phenyl-pyrrolidin-3-yl)-amine dihydrochloride cis-(6-Methoxy-3-methyl-3-trifluoromethyl-indan-5-ylmethyl)-(2-phenyl-pyrrolidin-3-yl)-amine dihydrochloride cis-(5-tert-Butyl-2-methoxy-benzyl)-([2R, 3R]-2-phenyl-pyrrolidin-3-yl)-amine dihydrochloride cis-(5-tert-Butyl-2-methoxy-benzyl)-([2S, 3S]-2-phenyl-pyrrolidin-3-yl)-amine dihydrochloride cis-2-[(2-Phenyl-pyrrolidin-3-ylamino)-methyl]-phenol dihydrochloride cis-3-Amino-2-phenyl-pyrrolidine-1-carboxylic acid benzyl ester p-toluenesulfonate cis-(2-Isopropoxy-5-trifluoromethoxy-benzyl)-(2-phenyl-pyrrolidin-3-yl)-amine dihydrochloride cis-6-Methoxy-1-methyl-7-[(2-phenyl-pyrrolidin-3-ylamino)-methyl]-3,4-dihydro-1H-[1,5]naphthyridin-2-one dihydrochloride cis-(6'-Methoxy-3,4,5,6-tetrahydro-2H-[1,3]bipyridinyl-5'-ylmethyl)-(2-phenyl-pyrrolidin-3-yl)-amine dihydrochloride cis-(5-Chloro-2-ethoxy-pyridin-3-ylmethyl)-(2-phenyl-pyrrolidin-3-yl)-amine cis-Dibenzofuran-2-ylmethyl-(2-phenyl-pyrrolidin-3-yl)-amine cis-(2,6-Dichloro4-methoxy-benzyl)-(2-phenyl-pyrrolidin-3-yl)-amine cis-(2-Methoxy-5-trifluoromethoxy-benzyl)-(2-phenyl-pyrrolidin-3-yl)-amine cis-(6-Methoxy-2-methyl-benzothiazol-5-ylmethyl)-(2-phenyl-pyrrolidin-3-yl)-amine cis-(6-Methoxy-2-phenyl-benzothiazol-7-ylmethyl)-(2-phenyl-pyrrolidin-3-yl)-amine cis-(2-Phenyl-pyrrolidin-3-yl)-(2,3,5-trichloro-benzyl)-amine cis-[2-(3,4-Dichloro-phenoxy)-5-fluoro-benzyl]-(2-phenyl-pyrrolidin-3-yl)-amine cis-[2-Methoxy-5-(5-trifluoromethyl-tetrazol-1-yl)-benzyl]-(2-phenyl-pyrrolidin-3-yl)-amine cis-2-[(2-Phenyl-pyrrolidin-3-ylamino)-methyl]-4-(5-trifluoromethyl-tetrazol-1-yl)-phenol cis-(5-Chloro-2-methoxy-benzyl)-(2-phenyl-pyrrolidin-3-yl)-amine cis-(2,3-Difluoro-benzyl)-(2-phenyl-pyrrolidin-3-yl)-amine cis-(2,5-Difluoro-benzyl)-(2-phenyl-pyrrolidin-3-yl)-amine cis-(2-Ethoxy-naphthalen-1-ylmethyl)-(2-phenyl-pyrrolidin-3-yl)-amine cis-(2-Phenyl-pyrrolidin-3-yl)-(4-propoxy-benzyl)-amine cis-(4-Ethyl-benzyl)-(2-phenyl-pyrrolidin-3-yl)-amine cis-(3-Ethoxy-4-methoxy-benzyl)-(2-phenyl-pyrrolidin-3-yl)-amine cis-(2-Phenyl-pyrrolidin-3-yl)-(2,3,6-trifluoro-benzyl)-amine cis-(3-Fluoro-2-methyl-benzyl)-(2-phenyl-pyrrolidin-3-yl)-amine cis-(2-Chloro-3,4-dimethoxy-benzyl)-(2-phenyl-pyrrolidin-3-yl)-amine cis-(2-Phenyl-pyrrolidin-3-yl)-thiophen-2-ylmethyl-amine cis-(2-Bromo-benzyl)-(2-phenyl-pyrrolidin-3-yl)-amine cis-(5-Bromo-2-methoxy-benzyl)-(2-phenyl-pyrrolidin-3-yl)-amine cis-(5-Methyl-furan-2-ylmethyl)-(2-phenyl-pyrrolidin-3-yl)-amine cis-(3-Methyl-thiophen-2-ylmethyl)-(2-phenyl-pyrrolidin-3-yl)-amine cis-(4-Phenoxy-benzyl)-(2-phenyl-pyrrolidin-3-yl)-amine cis-(2-Bromo-4,5-dimethoxy-benzyl)-(2-phenyl-pyrrolidin-3-yl)-amine cis-(2,3-Dichloro-benzyl)-(2-phenyl-pyrrolidin-3-yl)-amine cis-[3-(4-Methoxy-phenoxy)-benzyl]-(2-phenyl-pyrrolidin-3-yl)-amine cis-(2-Chloro-4-fluoro-benzyl)-(2-phenyl-pyrrolidin-3-yl)-amine.

cis-(5-Ethyl-furan-2-ylmethyl)-(2-phenyl-pyrrolidin-3-yl)-amine cis-(2-Chloro-quinolin-3-ylmethyl)-(2-phenyl-pyrrolidin-3-yl)-amine cis-(3-Methyl-benzo[b]thiophen-2-ylmethyl)-(2-phenyl-pyrrolidin-3-yl)-amine cis-Benzofuran-2-ylmethyl-(2-phenyl-pyrrolidin-3-yl)-amine cis-(2-Chloro-benzyl)-(2-phenyl-pyrrolidin-3-yl)-amine cis-(6-Methoxy-1-methyl-1-trifluoromethyl-isochroman-7-ylmethyl)-(2-phenyl-pyrrolidin-3-yl)-amine cis-2-Chloro-6-{3-[(2-phenyl-pyrrolidin-3-ylamino)-methyl]-phenoxy}-benzonitrile cis-(6-Bromo-2,3-dimethoxy-benzyl)-(2-phenyl-pyrrolidin-3-yl)-amine cis-(2-Bromo-3,6-dimethoxy-benzyl)-(2-phenyl-pyrrolidin-3-yl)-amine cis-(2,2-Dimethyl-chroman-6-ylmethyl)-(2-phenyl-pyrrolidin-3-yl)-amine cis-[3-(4-Ethyl-phenoxy)-benzyl]-(2-phenyl-pyrrolidin-3-yl)-amine trans-(2-Methoxy-benzyl)-(2-phenyl-pyrrolidin-3-yl)-amine trans-Benzyl-(2-phenyl-pyrrolidin-3-yl)-amine trans-(3-Chloro-benzyl)-(2-phenyl-pyrrolidin-3-yl)-amine trans-(3,5-Bis-trifluoromethyl-benzyl)-(2-phenyl-pyrrolidin-3-yl)-amine trans-5-{[2-(3-Chloro-phenyl)-pyrrolidin-3-ylamino]-methyl}-6-methoxy-3-methyl-1,1a,3,7b-tetrahydro-3-aza-cyclopropa[a]naphthalen-2-one trans-5-{[2-(4-Fluoro-2-methyl-phenyl)-pyrrolidin-3-ylamino]-methyl}-6-methoxy-3-methyl-1,1a,3,7b-tetrahydro-3-aza-cyclopropa[a]naphthalen-2-one or a pharmaceutically acceptable salt or solvate thereof.

Other more specific methods of this invention include the above methods wherein the compound of Formulae I or II is administered to a human for the treatment of major depressive disorder and concomitant generalized anxiety disorder.

Other more specific methods of this invention include the above methods wherein the compound of Formulae I or II is administered to a human for the treatment of major depressive disorder and concomitant irritable bowel syndrome.

Other more specific methods of this invention include the above methods wherein the compound of Formulae I or II is administered to a human for the treatment of major depressive disorder and concomitant functional abdominal pain.

Other more specific methods of this invention include the above methods wherein the compound of Formulae I or II is administered to a human for the treatment of major depressive disorder and concomitant neuropathic pain.

Other more specific methods of this invention include the above methods wherein the compound of Formulae I or II is administered to a human for the treatment of major depressive disorder and concomitant premenstrual dysphoric disorder.

Other more specific methods of this invention include the above methods wherein the compound of Formulae I or II is administered to a human for the treatment of major depressive disorder and concomitant dysthymia.

Other more specific methods of this invention include the above methods wherein the compound of Formulae I or II is administered to a human for the treatment of major depressive disorder and concomitant fibromyalgia.

Other more specific methods of this invention include the above methods wherein the compound of Formulae I or II is administered to a human for the treatment of major depressive disorder and a concomitant somatoform disorder such as somatization disorder, conversion disorder, body dysmorphic disorder, hypochondriasis, somatoform pain disorder or undifferentiated somatoform disorder.

Other more specific methods of this invention include the above methods wherein the compound of Formulae I or II is administered to a human for the treatment of generalized anxiety disorder and concomitant irritable bowel syndrome.

Other more specific methods of this invention include the above methods wherein the compound of Formulae I or II is administered to a human for the treatment of generalized anxiety disorder and concomitant functional abdominal pain.

Other more specific methods of this invention include the above methods wherein the compound of Formulae I or II is administered to a human for the treatment of generalized anxiety disorder and concomitant neuropathic pain.

Other more specific methods of this invention include the above methods wherein the compound of Formulae I or II is administered to a human for the treatment of generalized anxiety disorder and concomitant premenstrual dysphoric disorder.

Other more specific methods of this invention include the above methods wherein the compound of Formulae I or II is administered to a human for the treatment of generalized anxiety disorder and concomitant dysthymia.

Other more specific methods of this invention include the above methods wherein the compound of Formulae I or II is administered to a human for the treatment of generalized anxiety disorder and concomitant fibromyalgia.

Other more specific methods of this invention include the above methods wherein the compound of Formulae I or II is administered to a human for the treatment of generalized anxiety disorder and a concomitant somatoform disorder selected from the group consisting of somitization disorder, conversion disorder, hypochondriasis, somatoform pain disorder (or simply "pain disorder"), body dysmorphic disorder, undifferentiated somatoform disorder, and somatoform disorder not otherwise specified. See Diagnostic and Statistical manual of Mental Disorders, Fourth Edition (DSM-IV), American Psychiatric Association, Washington, D.C., Can 1194, pp. 435-436.

Other more specific methods of this invention include the above methods wherein the compound of Formulae I or II is administered to a human for the treatment of major depressive disorder accompanied by one or more somatic symptoms such as loss of appetite, sleep disturbances (e.g., insomnia, interrupted sleep, early morning awakening, tired awakening), loss of libido, restlessness, fatigue, constipation, dyspepsia, heart palpitations, aches and pains (e.g., headache, neck pain, back pain, limb pain, joint pain, abdominal pain), dizziness, nausea, heartburn, nervousness, tremors, burning and tingling sensations, morning stiffness, abdominal symptoms (e.g., abdominal pain, abdominal distention, gurgling, diarrhea), or the symptoms associated with generalized anxiety disorder (e.g., excessive anxiety and worry (apprehensive expectation), occurring more days than not for at least six months, about a number of events and activities, difficulty controlling the worry, etc.) See Diagnostic and Statistical manual of Mental Disorders, Fourth Edition (DSM-IV), American Psychiatric Association, Washington, D.C., Can 1194, pp. 435-436 and 445-469. This document is incorporated herein by reference in its entirety.

Other more specific methods of this invention include the above methods wherein the compound of Formulae I or II is administered to a human for the treatment of major depressive disorder accompanied by one or more somatic symptoms such fatigue, headache, neck pain, back pain, limb pain, joint pain, abdominal pain, abdominal distention, gurgling, diarrhea nervousness, or the symptoms associated with generalized anxiety disorder (e.g., excessive anxiety and worry (apprehensive expectation), occurring more days than not for at least six months, about a number of events and activities, difficulty controlling the worry, etc. See Diagnostic and Statistical manual of Mental Disorders, Fourth Edition (DSM-IV), American Psychiatric Association, Washington, D.C., Can 1194, pp. 435-436 and 445-469.

Other more specific methods of this invention include the above methods wherein the compound of Formulae I or II is administered to a human for the treatment of generalized anxiety disorder accompanied by one or more somatic symptoms such as loss of appetite, sleep disturbances (e.g., insomnia, interrupted sleep, early morning awakening, tired awakening), loss of libido, restlessness, fatigue, constipation, dyspepsia, heart palpitations, aches and pains (e.g., headache, neck pain, back pain, limb pain, joint pain, abdominal pain), dizziness, nausea, heartburn, nervousness, tremors, burning and tingling sensations, morning stiffness, abdominal symptoms (e.g., abdominal pain, abdominal distention, gurgling, diarrhea), or the symptoms associated with major depressive disorder (e.g., sadness, tearfulness, loss of interest, fearfulness, helplessness, hopelessness, fatigue, low self esteem, obsessive ruminations, suicidal thoughts, impaired memory and concentration, loss of motivation, paralysis of will, reduced appetite, increased appetite).

Other more specific methods of this invention include the above methods wherein the compound of Formulae I or II is administered to a human for the treatment of generalized anxiety disorder accompanied by one or more somatic symptoms such as fatigue, headache, neck pain, back pain, limb pain, joint pain, abdominal pain, abdominal distention, gurgling, diarrhea nervousness, or the symptoms associated with major depressive disorder (e.g., sadness, tearfulness, loss of interest, fearfulness, helplessness, hopelessness, low self esteem, obsessive ruminations, suicidal thoughts, fatigue, impaired memory and concentration, loss of motivation, paralysis of will, reduced apetite, increased appetite).

The present invention also includes isotopically labelled compounds, which are identical to those recited in Formulae I or II compounds, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, can be preferred in some circumstances. Isotopically labelled compounds of Formulae I or II of this invention and prodrugs thereof can generally be prepared by carrying out the procedures disclosed in the Schemes and/or in the Examples and Preparations below, by substituting a readily available isotopically labelled reagent for a non-isotopically labelled reagent.

In another practice, the compound of Formulae I or II can be used in conjunction with one or more other therapeutic agents, e.g. different antidepressant agents such as tricyclic antidepressants (e.g. amitriptyline, dothiepin, doxepin, trimipramine, butripyline, clomipramine, desipramine, imipramine, iprindole, lofepramine, nortriptyline or protriptyline), monoamine oxidase inhibitors (e.g. isocarboxazid, pheneizine or tranylcyclopramine) or 5-HT re-uptake inhibitors (e.g. fluvoxamine, sertraline, fluoxetine or paroxetine), and/or with antiparkinsonian agents such as dopaminergic antiparkinsonian agents (e.g. levodopa, preferably in combination with a peripheral decarboxylase inhibitor e.g. benserazide or carbidopa, or with a dopamine agonist e.g., bromocriptine, lysuride or pergolide).

In a preferred practice, the compound of Formulae I or II is used in combination with a 5-HT re-uptake inhibitor (e.g. fluvoxamine, sertraline, fluoxetine or paroxetine), preferably sertraline (or a pharmaceutically acceptable salt or polymorph thereof as would be understood by the artisan) as psychotherapeutics and can be used in the treatment or prevention of disorders the treatment or prevention of which is facilitated by modulating serotonergic neurotransmission such as hypertension, depression (e.g. depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g. agoraphobia, social phobia and simple phobias), posttraumatic stress syndrome, avoidant personality disorder, premature ejaculation, eating disorders (e.g. anorexia nervosa and bulimia nervosa), obesity, chemical dependencies (e.g. addictions to alcohol, cocaine, heroin, phenobarbital, nicotine and benzodiazepines), cluster headache, migraine, pain, Alzheimer's disease, obsessive-compulsive disorder, panic disorder, memory disorders (e.g. dementia, amnestic disorders, and age-related cognitive decline (ARCD)), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g. small cell lung carcinoma), chronic paroxysmal hemicrania and headache (associated with vascular disorders).

Sertraline, (1S-cis)-4-(3,4-dichlorophenyl)-1,2,3,4-tetrahydro-N-methyl-1-naphthalenamine, has the chemical formula $C_{17}H_{17}NC_{12}$; its synthesis is described in U.S. Pat. No. 4,536,518 incorporated herein by reference. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation Administration The compound of the invention can be administered either alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed thereby can be readily administered in a variety of dosage forms such as tablets, powders, lozenges, liquid preparations, syrups, injectable solutions and the like. These pharmaceutical compositions can optionally contain additional ingredients such as flavorings, binders, excipients and the like.

Thus the compound of the invention can be formulated for oral, buccal, intranasal, parenteral (e.g. intravenous, intramuscular or subcutaneous), transdermal (e.g. patch) or rectal administration or in a form suitable for administration by inhalation or insufflation. E.g. for oral administration, the pharmaceutical compositions can take the form of tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets can be coated by methods known in the art. Liquid preparations for oral administration can take the form of e.g. solutions, syrups or suspensions, or they can be presented as a dry product for constitution with water or other suitable vehicle before use. Such liquid preparations can be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid). For buccal administration, the composition can take the form of tablets or lozenges formulated in conventional manner.

The compound of the invention can be formulated for parenteral administration by injection, including using conventional catheterization techniques or infusion. Formulations for injection can be presented in unit dosage form, e.g. in ampules or in multi-dose containers, with an added preservative. They can take such forms as suspensions, solutions or emulsions in oily or aqueous vehicles, and can contain formulating agents such as suspending, stabilizing and/or dispersing agents. Alternatively, the active ingredient can be in powder form for reconstitution with a suitable vehicle, e.g. sterile pyrogen-free water, before use.

The compound of the invention can also be formulated in rectal compositions such as suppositories or retention enemas, e.g. containing conventional suppository bases such as cocoa butter or other glycerides.

For intranasal administration or administration by inhalation, the compound of the invention is conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. The pressurized container or nebulizer can contain a solution or suspension of the active compound. Capsules and cartridges (made e.g. from gelatin) for use in an inhaler or insufflator can be formulated containing a powder mix of a compound of the invention and a suitable powder base such as lactose or starch.

A proposed dose of the active compounds of the invention for oral, parenteral or buccal administration to the average adult human for the treatment of the conditions referred to above is about 0.1 to about 200 mg of the active ingredient per unit dose which could be administered, for example, 1 to 4 times per day.

Aerosol formulations for treatment of the conditions referred to above in the average adult human are preferably arranged so that each metered dose or "puff" of aerosol contains about 20 mg to about 1000 mg of the compound of the invention. The overall daily dose with an aerosol will be within the range of about 100 mg to about 10 mg. Administration can be once or several times daily, e.g. 2, 3, 4 or 8 times, giving for example, 1, 2 or 3 doses each time.

In connection with the use of the compound of the invention with a 5-HT re-uptake inhibitor, preferably sertraline, for the treatment of subjects possessing any of the above conditions, it is to be noted that these can be administered either alone or in combination with pharmaceutically acceptable carriers by either of the routes previously indicated, and that such administration can be carried out in both single and multiple dosages. More particularly, the active combination can be administered in a wide variety of different dosage forms, i.e. they can be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of Formulae I or II are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e. in amounts which are sufficient to provide the desired unit dosage.

A proposed daily dose of the compound of the invention in the combination formulation (a formulation containing the compound of the invention and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of the compound of Formulae I or II per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20000; preferably from about 0.25 to about 2000.

Aerosol combination formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration can be once or several times daily, e.g. 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a 5-HT re-uptake inhibitor, preferably sertraline, preferably from about 1 mg to about 200 mg of sertraline. Administration can be once or several times daily, for example 2, 3, 4 or 8 times, giving for example, 1, 2 or 3 doses each time.

As previously indicated, a 5-HT re-uptake inhibitor, preferably sertraline, in combination with compounds of Formulae I or II are readily adapted to therapeutic use as antidepressant agents. In general, these antidepressant compositions containing a 5-HT re-uptake inhibitor, preferably sertraline, and a compound of Formulae I or II are normally administered in dosages ranging from about 0.01 mg to about 100 mg per kg of body weight per day of a 5-HT re-uptake inhibitor, preferably sertraline, preferably from about 0.1 mg to about 10 mg per kg of body weight per day of sertraline; with from about 0.001 mg. to about 100 mg per kg of body weight per day of a compound of Formulae I or II, preferably from about 0.01 mg to about 10 mg per kg of body weight per day of a compound of Formulae I or II, although variations will necessarily occur depending upon the conditions of the subject being treated and the particular route of administration chosen.

Additionally, it is also possible to administer the compounds of Formulae I or II or their pharmaceutically acceptable salts or solvates topically and this can preferably be done by way of creams, jellies, gels, pastes, ointments and the like, in accordance with standard pharmaceutical practice.

NK1 Assays:

The activity of the compounds of Formulae I or II or their pharmaceutically acceptable salts or solvates as substance P antagonists (NK1) can be determined by their ability to inhibit the binding of substance P at its receptor sites in bovine caudate tissue, employing radioactive ligands to visualize the tachykinin receptors by means of autoradiography. The substance P antagonizing activity of the herein described compounds can be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 μg/ml of leupeptin, 2 μg of chymostatin and 200 g/ml of bovine serum albumin. This step completes the production of the tissue preparation.

The radioligand binding procedure is then carried out in the following manner, viz., by initiating the reaction via the addition of 100 μl of the test compound made up to a concentration of 1 μM, followed by the addition of 100 μl of radioactive ligand made up to a final concentration 0.5 mM and then finally by the addition of 800 μl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The compounds of Formulae I or II that are basic in nature are capable of forming a wide variety of different salts with various inorganic and organic acids. Although such salts must be pharmaceutically acceptable for administration to animals, it is often desirable in practice to initially isolate a compound of Formulae I or II or from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of Formulae I or II that are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of Formulae I or II. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

In the schemes and examples below, the following terms are intended to have the following, general meaning:

° C.: degrees Celsius
d; doublet (spectral)
g: grams
mg: milligrams
h: hours
HRMS: High Resolution Spectrometry
Hz: hertz
J: coupling constant (in NMR)
KHMDS: potassium hexamethyldisilazane
L: liter(s)
LAH: lithium aluminum hydride
LiHMDS: lithium hexamethyldisilazane
M/Z mass to charge ratio (in mass spectrometry)
NaHMDS: sodium hexamethyldisilazane
NMR: nuclear magnetic resonance
rt or RT: room temperature
s: singlet (NMR),
t: triplet (NMR)

General Synthetic Schemes

The following schemes are representative of methods useful in synthesizing the compound of the present invention they are not to constrain the scope of same in any way.

The compound of the invention having Formulae (I) or (II) includes pharmaceutically acceptable salts thereof e.g. acid addition salts, base addition salts, and pro-drugs and solvates thereof. The compound of the invention having Formulae (I) or (II) may also have optical centers hence occurring in different enantiomeric configurations. The invention includes all enantiomers, diastereomers and other stereoisomers and optical isomers as well as racemic mixtures thereof. E.g. the compound of the invention having Formulae (I) or (II) includes (R) and (S) enantiomers and cis and trans isomers including without limitation those delineated at the atoms bearing the "*" insignia. The compound of the invention having Formulae (I) or (II) also includes all radio-labeled forms of said formulae.

As appreciated by the artisan, the use of Formulae (I) and (II) is a convenience and the invention is understood to include each and every species falling thereunder as though individually set forth herein. Thus the invention severally contemplates each species separately and any and all combinations of such species.

Without restriction, the compound of the invention can be prepared by the following schemes:

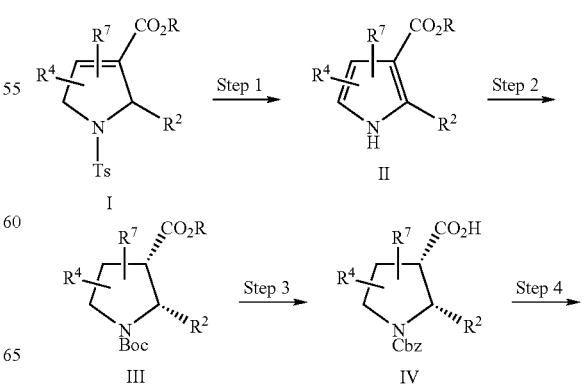

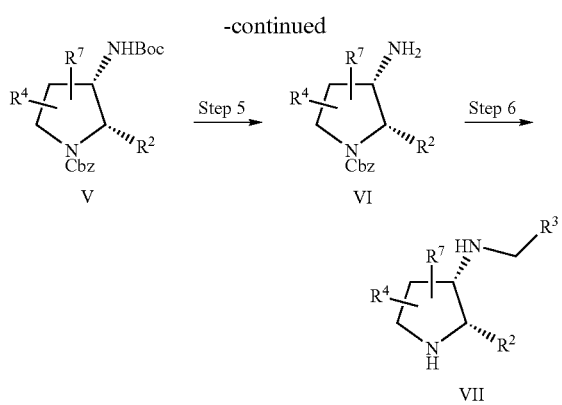

Wherein R represents alkyl and R², R³, R⁴, and R⁷ have the same meanings as defined hereinabove.

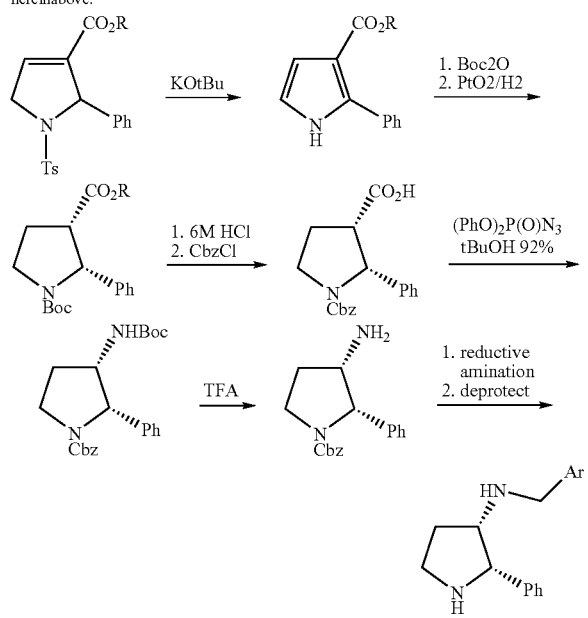

Scheme 1 depicts a method for the synthesis of cis-2-phenyl-3-aminopyrrolidine compounds.

Step 1. The N-tosyl-dihydropyrrole derivative (I) can be treated with a base such as TBAF in THF to cleave the toluenesulfonyl group and generate the pyrrole(II). [1] Other non-limiting examples of bases which can be used include potassium tert-butoxide or hindered strong bases such as KHMDS, NaHMDS, or LiHMDS. A preferred method involves the use of potassium tert-butoxide in dimethylformamide.

Step 2 The resultant pyrrole (II) from step 1 is protected at the nitrogen atom with a Boc group, and reduced to 2,3-cis-pyrrolidine by treatment with a palladium catalyst, such as PtO₂, and hydrogen gas in a Par apparatus to yield compound (III).

Step 3 The alkyl ester of compound (III) is cleaved via acid hydrolysis with aqueous hydrochloric or sulfuric acid, which also serves to cleave the Boc group. The Cbz group is then added using standard conditions to yield compound (IV). This involves treatment of a THF/water mixture of the amine with Cbz-chloride and a carbonate or hydroxide base such as sodium bicarbonate, sodium carbonate, or sodium hydroxide. The reaction is not limited to employment of THF, since a variety of other solvents can be used. These solvents include but are not limited to, inert solvents such as ether, dioxane, methylene chloride, and DMF.

Step 4 The carboxylic acid functionality of compound (IV) is converted into a Boc-protected amine group via the Curtius rearrangement [2, 3] to yield compound (V). This reaction involves treatment of the carboxylic acid with diphenylphosphoryl azide in tert-butanol to give an acyl azide. Heating causes a rearrangement of the azide to give an isocyanate, which is trapped by the solvent tert-butanol to provide the Boc-amine.

Step 5 The Boc group of compound (V) can be cleaved selectively over the Cbz group using known methods [4, 5] to yield compound (VI). Other strong acids and different solvents can be used for this transformation. Examples of alternative acids include HCl, H₂SO₄, and p-toluenesulfonic acid. Examples of alternative solvents include but are not limited to ether, chloroform, dioxane, glyme, and alcohols such as methanol or ethanol.

A preferred method involves treatment with trifluoroacetic acid with or without a solvent.

Step 6 The free amine group of compound (VI) is alkylated via reductive alkylation reaction in a suitable solvent to yield compound (VII). In this reaction, the amine is treated with an aldehyde or a ketone and a reducing agent in a suitable solvent. Two common reducing agents are sodium cyanoborohydride and sodium triacetoxyborohydride. Alternatively, catalytic hydrogenation can also be used. Non-limiting examples of suitable solvents include various alcohols, as well as inert solvents such as methylene chloride, THF, ether, toluene, benzene, glyme, or chloroform. Preferably, alcoholic solvents are used with sodium cyanoborohydride and catalytic hydrogenation, while the inert solvents are often used with sodium triacetoxyborohydride. Subsequent to reductive amination, the Cbz group is cleaved by known methods such as hydrolytic cleavage catalyzed by HBr in acetic acid, or catalytic hydrogenolysis which can be mediated by a large variety of conditions. A preferred set of conditions is transfer hydrogenation induced by heating an alcoholic solution of the substrate with palladium on carbon in the presence of ammonium formate. Another preferred set of conditions is hydrogenation under hydrogen gas in an ethanolic solution catalyzed by a palladium catalyst such as 5% palladium on carbon. Many of these methods are described in the literature.[4, 5]

Scheme 2

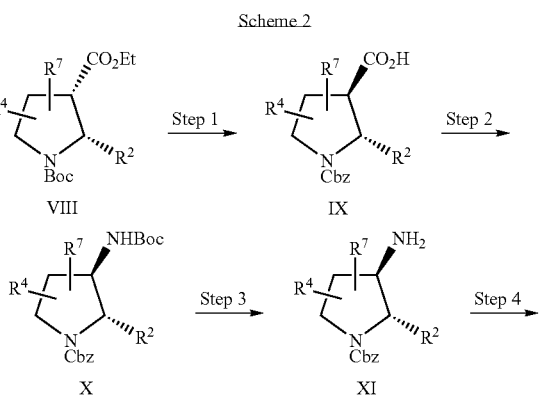

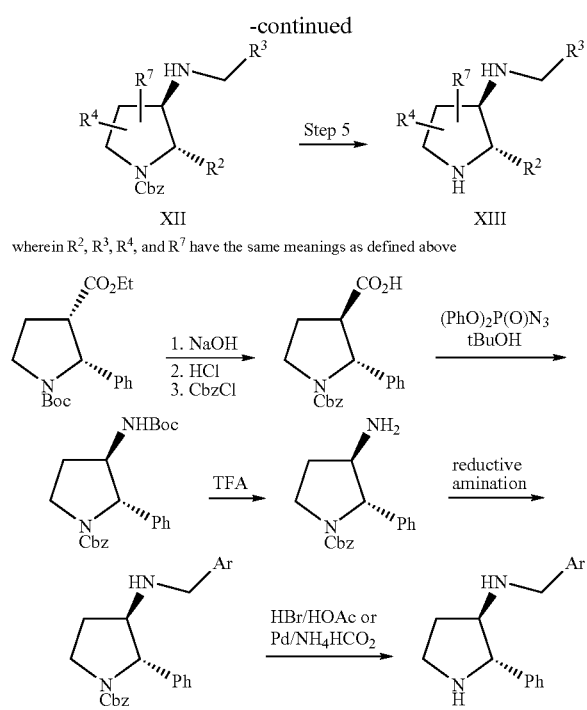

wherein $R^2$, $R^3$, $R^4$, and $R^7$ have the same meanings as defined above

Scheme 2 depicts a method for the synthesis of trans-2-phenyl-3-aminopyrrolidine compounds from an N-protected, cis-2-phenylpyrrolidine-3-carboxy-compound.

Step 1 A 2,3-cis-pyrolidine compound (VIII) is epimerized by treatment with a base, such aqueous sodium-, lithium- or potassium hydroxide, to generate a 2,3-trans-pyrrolidine. Replacement of the Boc group with the Cbz group is accomplished using standard conditions to yield compound (IX). Examples of alternative solvents include but are not limited to ether, chloroform, dioxane, glyme, and alcohols such as methanol or ethanol. The Cbz group is then added via treatment of a THF/water mixture of the amine with Cbz-chloride and a carbonate or hydroxide base such as sodium bicarbonate, sodium carbonate, or sodium hydroxide. The reaction is not limited to employment of THF, since a variety of other solvents can be used. These solvents include but are not limited to, inert solvents such as ether, dioxane, methylene chloride, and DMF.

Step 2 Compound (IX) is subjected to a curtius rearrangement induced by treatment with phosphorazidic acid diphenyl ester in t-butanol. The product of this reaction (X) is a pyrrolidine possessing a Boc-amino substituent in the 3-position.

Step 3 The Boc group of compound (X) is cleaved selectively over the Cbz group using known methods [4, 5] to yield compound (XI). Examples of alternative acids include HCl, $H_2SO_4$, and p-toluenesulfonic acid. Examples of alternative solvents include but are not limited to ether, chloroform, dioxane, glyme, and alcohols such as methanol or ethanol. A preferred method involves treatment with trifluoroacetic acid with or without a solvent.

Step 4 The free amine group of compound (XI) is alkylated via reductive alkylation reaction in a suitable solvent to yield compound (XII). In this reaction, the amine is treated with an aldehyde or a ketone and a reducing agent in a suitable solvent. Two common reducing agents are sodium cyanoborohydride and sodium triacetoxyborohydride. Alternatively, catalytic hydrogenation can also be used. Non-limiting examples of suitable solvents include various alcohols, as well as inert solvents such as methylene chloride, THF, ether, toluene, benzene, glyme, or chloroform. Preferrably, alcoholic solvents are used with sodium cyanoborohydride and catalytic hydrogenation, while the inert solvents are often used with sodium triacetoxyborohydride.

Step 5 The Cbz group is then cleaved by known methods such as hydrolytic cleavage catalyzed by HBr in acetic acid, or catalytic hydrogenolysis which can be mediated by a large variety of conditions. A preferred set of conditions is transfer hydrogenation induced by heating an alcoholic solution of the substrate with palladium on carbon in the presence of ammonium formate. Another preferred set of conditions is hydrogenation under hydrogen gas in an ethanolic solution catalyzed by a palladium catalyst such as 5% palladium on carbon. Many of these methods are described in the literature.[4, 5]

Experimental Section

The requisite aldehydes for the following procedures were obtained commercially or were prepared according to published procedures including those described in WO2001 077100.

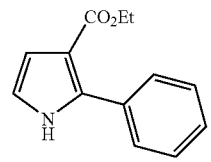

PREPARATORY EXAMPLE 1

2-Phenyl-1H-pyrrole-3-carboxylic acid ethyl ester

2-Phenyl-1-(toluene-4-sulfonyl)-2,5-dihydro-1H-pyrrole-3-carboxylic acid ethyl ester (0.42 g, 1.13 mmol) (prepared according to the method disclosed in reference 1) and 1.0 M potassium tert-butoxide in THF (1.42 mL, 1.42 mmol) were stirred in THF at 0° C. for 30 min, then warmed to rt for 30 min. The reaction was diluted with diethyl ether, washed 1× with satd. $NH_4Cl$, dried over $MgSO_4$, filtered, and concentrated. Silica gel chromatography using hexanes/ethyl acetate (9:1) gave 0.195 g of title compound. (80% yield). $^1$H NMR ($CDCl_3$) δ 9.14 (bs, 1H), 7.50-7.46 (m, 2H), 7.32-7.27 (m, 3H), 6.68-6.66 (t, J=2.90 Hz, 1H), 6.56-6.55 (t, J=2.90 Hz, 1H), 4.12-4.06 (q, J=7.25 Hz, 2H), 1.20-1.16 (t, J=7.25 Hz, 3H). $^{13}$C NMR ($CDCl_3$) δ 165.8, 137.4, 132.4, 129.3, 128.8, 128.3, 128.2, 118.3, 112.1, 60.0, 14.4; MS APCI: $[M+H]^+$=216.1.

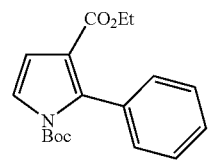

PREPARATORY EXAMPLE 2

2-Phenyl-pyrrole-1,3-dicarboxylic acid 1-tert-butyl ester 3-ethyl ester

A mixture of 2-phenyl-1H-pyrrole-3-carboxylic acid ethyl ester (0.391 g, 1.82 mmol), triethylamine (0.279 mL, 2.00 mmol) obtained from preparatory example 1,4-N,N-dimethylaminopyridine (catalytic; ~0.05 mol %), and di-tert-butyldicarbonate (0.437 g, 2.00 mmol) was stirred in acetonitrile at rt for 3 days. The mixture was concentrated, dissolved in ether, washed 1× with satd. NH₄Cl, dried over MgSO₄, filtered, and concentrated. The residue was suspended in hexanes and filtered to remove solids. The filtrate was concentrated to give 0.49 g (86%) of the title compound. ¹H NMR (CDCl₃) δ 7.35-7.23 (m, 6H), 6.65-6.64 (d, J=3.73 Hz, 1H), 4.06-4.01 (q, J=7.05 Hz, 2H), 1.20 (s, 9H), 1.05-1.02 (t, J=7.05 Hz, 3H). ¹³C NMR (CDCl₃) δ 164.2, 149.0, 138.3, 133.6, 130.2, 128.1, 127.5, 121.4, 118.6, 111.6, 84.6, 60.0, 27.5, 14.1; MS APCI: [M+H]⁺=316.1

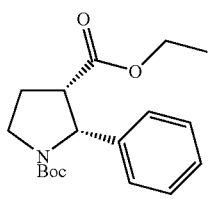

PREPARATORY EXAMPLE 3 cis-2-Phenyl-pyrrolidine-1,3-dicarboxylic acid 1-tert-butyl ester 3-ethyl ester

2-Phenyl-pyrrole-1,3-dicarboxylic acid 1-tert-butyl ester 3-ethyl ester (24.75 g, 78.6 mmol), obtained from preparatory example 2, and platinum (IV) oxide (5 g) were shaken in 350 mL of ethanol at rt under 45 psi of hydrogen for 16 h. The mixture was carefully filtered through Celite, and the filtrate was concentrated. The concentrate was passed through a small silica gel plug eluting with a hexanes/ethyl acetate gradient (100:0 to 85:15) to give 21.9 g (87%) of the title compound. HRMS : calculated; 320.1870, found; 320.1862.

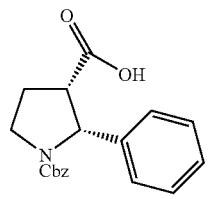

PREPARATORY EXAMPLE 4 cis-2-Phenyl-pyrrolidine-1,3-dicarboxylic acid 1-benzyl ester

Cis-2-Phenyl-pyrrolidine-1,3-dicarboxylic acid 1-tert-butyl ester 3-ethyl ester (23.2 g, 72.7 mmol), obtained from preparatory example 3, was stirred in 1,4-dioxane (250 mL) and 6M HCl (250 mL) at 70° C. for 20 h. The mixture was cooled to 0° C. and carefully saturated with solid sodium bicarbonate. Benzyl chloroformate (104 mL, 72.7 mmol) was added and the resultant mixture was stirred for 1 h at 0° C. and at rt for 20 h. The mixture was then cooled to 0° C. and 6 M HCl was carefully added to pH ~1. The mixture was extracted 3× with ethyl acetate and the combined extracts were dried over MgSO₄, filtered, and concentrated to give 17.5 g of a brown oil. The oil was crystallized from hexanes/ethyl acetate (10:1, 150 mL) to give 10.0 g (42%) of the title compound. ¹H NMR (CD₃OD) δ 7.32-7.08 (m, 9H), 6.80-6.78 (d, J=7.05 Hz, 1H), 5.21-5.17 (m, 1H), 5.09-4.83 (m, 2H), 3.91-3.83 (m, 1H), 3.63-3.40 (m, 2H), 2.41-2.30 (m, 1H), 2.08-2.03 (m, 1H). MS APCI: [M+H]⁺=326.2.

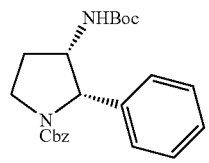

PREPARATORY EXAMPLE 5 cis-3-tert-Butoxycarbonylamino-2-phenyl-pyrrolidine-1-carboxylic acid benzyl ester cis-2-Phenyl-pyrrolidine-1,3-dicarboxylic acid 1-benzyl ester (9.40 g, 28.9 mmol), obtained from preparatory example 4, triethylamine (9.1 mL, 65.1 mmol), and diphenylphosphoryl azide (6.41 mL, 31.8 mmol) were stirred in tert-butyl alcohol (250 mL) at reflux for 3 h. The mixture was concentrated, dissolved in CH₂Cl₂, washed 1× with 1M NaOH, 1× with 0.5 M HCl, dried over MgSO₄, filtered, and concentrated to give 10.5 g of title compound, 92% yield. MS APCI: [M+H]⁺=397.2.

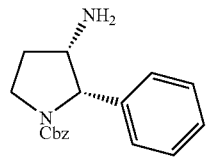

PREPARATORY EXAMPLE 6 cis-3-Amino-2-phenyl-pyrrolidine-1-carboxylic acid benzyl ester p-toluenesulfonate cis-3-tert-Butoxycarbonylamino-2-phenyl-pyrrolidine-1-carboxylic acid benzyl ester (10.5 g, 26.5 mmol) obtained from preparatory example 5, was stirred in 100 mL of methylene chloride and 75 mL of trifluoroacetic acid at rt for 1.5 h. The mixture was then basified with 3 M NaOH and the organics were separated, dried over MgSO₄, filtered, and concentrated to give 8.5 g of free base. The free base was dissolved in hot ethyl acetate, and 1.0 eq of p-toluenesulfonic acid monohydrate was added as a solution in hot ethyl acetate and the resultant mixture was stirred at rt for 16 h. The suspension was then filtered and dried under vacuum to give 6.9 g (56%) of the title compound. ¹H NMR (CD₃OD) δ 7.68-7.66 (d, J=7.88 Hz, 2H), 7.42-7.10 (m, 11H), 6.81-6.79 (bs, 1H), 5.16-5.15 (d, J=7.47 Hz, 1H), 5.10-4.95 (m, 2H), 4.05-4.00 (m, 1H), 3.95-3.82 (m, 1H), 3.70-3.60 (m, 1H), 2.33 (s, 4H), 2.15-2.05 (m, 1H). MS APCI: [M+H]⁺=297.2.

PREPARATORY EXAMPLE 7 cis-3-Amino-2-(3-chloro-phenyl)-pyrrolidine-1-carboxylic acid benzyl ester p-toluenesulfonate Prepared as in preparatory examples 1-6 wherein 2-(3-chloro-phenyl)-1-(toluene-4-sulfonyl)-2,5-dihydro-1H-pyrrole-3-carboxylic acid ethyl ester is substituted for 2-phenyl-1-(toluene-4-sulfonyl)-2,5-dihydro-1H-pyrrole-3-carboxylic acid ethyl ester in preparatory example 1.

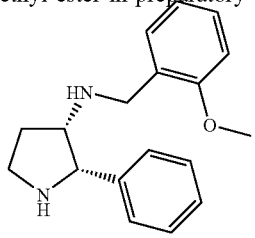

EXAMPLE 1 cis-(2-Methoxy-benzyl)-(2-Phenyl-pyrrolidin-3-yl)-amine dihydrochloride cis-3-Amino-2-phenyl-pyrrolidine-1-carboxylic acid benzyl ester p-toluenesulfonate (0.289 g, 0.62 mmol), obtained from preparatory example 6, o-anisaldehyde (0.084 g, 0.62 mmol), and sodium triacetoxyborohydride (0.167 g, 0.77 mmol) were stirred in 6 mL of methylene chloride at rt for 4 h. The organic solution was washed 1× with 1M NaOH, dried through cotton, and concentrated to give an oil. The oil was dissolved in methanol (6 mL). Ammonium formate (0.379 g, 6 mmol) and 10% palladium on carbon (ca. 20 wt %) were carefully added. The reaction was warmed to reflux for 1 hr, and then cooled to rt, filtered carefully through Celite, and concentrated. The residue was dissolved in 1 M HCl, washed 2× with $CH_2Cl_2$, and basified with excess 3 M NaOH. The aqueous solution was extracted 5× with $CH_2Cl_2$ and the combined extracts were dried through cotton and concentrated to give 0.144 g (85%) of the title compound. The dihydrochloride salt was prepared via the addition of concentrated HCl to a solution of the free base in isopropanol and concentration. The residue was crystallized from isopropanol/methanol (ca.2:1). $^1H$ NMR (2HCl, $CD_3OD$) δ 7.70-7.67 (m, 2H), 7.63-7.59 (m, 3H), 7.44-7.40 (m, 1H), 7.28-7.26 (d, J=7.46 Hz, 1H), 7.04-7.01 (d, J=8.29 Hz, 1H), 6.99-6.95 (t, J=7.46 Hz, 1H), 5.21-5.20 (d, J=7.05 Hz, 1H), 4.36-4.30 (q, J=7.46 Hz, 1H), 4.23-4.20 (d, J=12.85 Hz, 1H), 4.05-4.02 (d, J=12.85 Hz, 1H), 3.92-3.86 (ddd, J=12.04, 9.33, 3.52 Hz, 1H), 3.76 (s, 3H), 3.56-3.52 (m, 1H), 2.80-2.75 (m, 1H), 2.69-2.63 (m, 1H). $^{13}C$ NMR (free base, $CDCl_3$) δ 157.9, 139.8, 130.0, 128.5, 128.3, 128.2, 127.6, 127.1, 120.4, 110.1, 67.0, 60.142 55.1, 47.5, 45.3, 32.1; MS APCI: $[M+H]^+$=283.1.

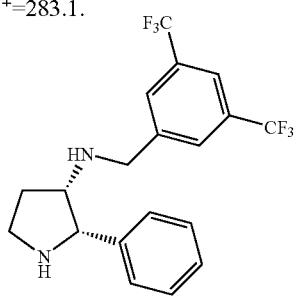

EXAMPLE 2 cis-(3,5-Bis-trifluoromethyl-benzyl)-(2-phenyl-pyrrolidin-3-yl)-amine dihydrochloride cis-3-Amino-2-phenyl-pyrrolidine-1-carboxylic acid benzyl ester p-toluenesulfonate (0.289 g, 0.62 mmol), obtained from preparatory example 6, 3,5-bis-trifluoromethyl-benzaldehyde (0.62 mmol), and sodium triacetoxyborohydride (0.167 g, 0.77 mmol) were stirred in 6 mL of methylene chloride at rt for 4 h. The organic solution was washed 1× with 1M NaOH, dried through cotton, and concentrated to give an oil. The oil was dissolved in methanol (6 mL). Ammonium formate (0.379 g, 6 mmol) and 10% palladium on carbon (ca. 20 wt %) were carefully added. The reaction was warmed to reflux for 1 hr, and then cooled to rt, filtered carefully through Celite, and concentrated. The residue was dissolved in 1M HCl, washed 2× with $CH_2Cl_2$, and basified with excess 3 M NaOH. The aqueous solution was extracted 5× with $CH_2Cl_2$ and the combined extracts were dried through cotton and concentrated to give 0.144 g (85%) of the title compound. The dihydrochloride salt was triturated with hot isopropanol and collected via filtration to provide the title compound in 32% yield. $^1H$ NMR (2HCl, $CD_3OD$) δ 8.01-8.00 (m, 3H), 7.69-67 (m, 2H), 7.58-7.55 (m, 3H), 5.17-5.15 (d, J=6.63 Hz, 1H), 4.42-4.38 (d, J=13.3 Hz, 1H), 4.35-4.28 (m, 1H), 4.03-4.00 (d, J=13.3 Hz, 1H), 3.93-3.87 (m, 1H), 3.59-3.51 (m, 1H), 2.90-2.79 (m, 1H), 2.73-2.65 (m, 1H). MS APCI: $[M+H]^+$=389.1.

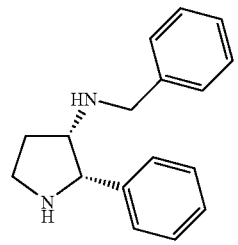

EXAMPLE 3 cis-Benzyl-(2-phenyl-pyrrolidin-3-yl)-amine dihydrobromide

A mixture of cis-3-amino-2-phenyl-pyrrolidine-1-carboxylic acid benzyl ester p-toluenesulfonate (0.15 g, 0.32 mmol), obtained from preparatory example 6, benzaldehyde (0.034 g, 0.34 mmol), and sodium triacetoxyborohydride (0.082 g, 0.38 mmol) was stirred in 3 mL of methylene chloride at rt for 16 h. The reaction was washed 1× with 1M NaOH, dried through cotton, and concentrated to give an oil. The oil was dissolved in acetic acid (1 mL) and a solution of 30% hydrogen bromide in acetic acid (0.302 g, 1.12 mmol) was added. The solution was stirred for 16 h and the resultant solids were collected, washed with ether, and concentrated under vacuum to give 0.117 g (88%) of the title compound. $^1H$ NMR (2HBr, $CD_3OD$) δ 7.69-7.67 (m, 2H), 7.62-7.60 (m, 3H), 7.43-7.38 (m, 3H), 7.37-7.32 (m, 2H), 5.29-5.27 (d, J=7.46 Hz, 1H), 4.41-4.35 (dd, J=8.30, 7.88 Hz, 1H), 4.28-4.24 (d, J=13.0 Hz, 1H), 4.04-4.01 (d, J=13.0, 1H), 3.96-3.90 (ddd, J=12.23, 9.33, 2.9 Hz, 1H), 3.61-3.58

(m, 1H), 2.87-2.80 (m, 1H), 2.64-2.55 (m, 1H). MS APCI: [M+H]⁺=253.2.

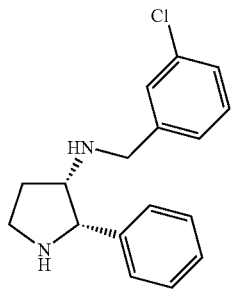

EXAMPLE 4 cis-(3-Chloro-benzyl)-(2-Phenyl-pyrrolidin-3-yl)-amine dihydrobromide

A mixture of cis-3-amino-2-phenyl-pyrrolidine-1-carboxylic acid benzyl ester p-toluenesulfonate (0.15 g, 0.32 mmol), obtained from preparatory example 6,3-chlorobenzaldehyde (0.34 mmol), and sodium triacetoxyborohydride (0.082 g, 0.38 mmol) was stirred in 3 mL of methylene chloride at rt for 16 h. The reaction was washed 1× with 1M NaOH, dried through cotton, and concentrated to give an oil. The oil was dissolved in acetic acid (1 mL) and a solution of 30% hydrogen bromide in acetic acid (0.302 g, 1.12 mmol) was added. The solution was stirred for 16 h and the resultant solids were collected, washed with ether, and concentrated under vacuum to give 0.114 g (79%) of the title compound. ¹H NMR (2HBr, CD₃OD) δ 7.72-7.68 (m, 2H), 7.64-7.57 (m, 3H), 7.45-7.31 (m, 4H), 5.31-5.29 (d, J=7.46 Hz, 1H), 4.45-4.41 (q, J=7.88 Hz, 1H), 4.31-4.28 (d, J=12.85 Hz, 1H), 4.04-4.01 (d, J=12.85 Hz, 1H), 3.97-3.91 (ddd, J=12.13, 9.33, 2.90 Hz, 1H), 3.62-3.54 (m, 1H), 2.89-2.81 (m, 1H), 2.66-2.56 (m, 1H). MS APCI: [M+H]⁺=287.2.

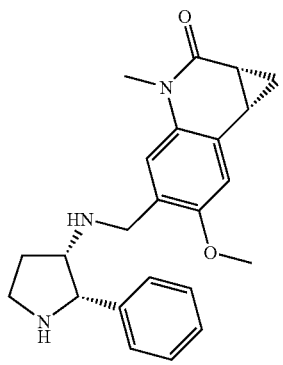

EXAMPLE 5 cis-6-Methoxy-3-methyl-5-[(2-phenyl-pyrrolidin-3-ylamino)-methyl]-1,1a,3,7b-tetrahydro-3-aza-cyclopropa[a]naphthalen-2-one dihydrochloride A mixture of cis-3-amino-2-phenyl-pyrrolidine-1-carboxylic acid benzyl ester p-toluenesulfonate (0.15 g, 0.32 mmol), obtained from preparatory example 6,6-methoxy-3-methyl-2-oxo-1a,2,3,7b-tetrahydro-1H-3-aza-cyclopropa[a]naphthalene-5-carbaldehyde (0.078 g, 0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated to give 0.131 g of the title compound. The dihydrochloride salt was prepared by addition of conc. HCl to free base in isopropanol and concentration under vacuum. Crystallize from ethyl acetate/isopropanol yielded 0.08 g of title compound. ¹H NMR (2HCl, CD₃OD) δ 7.71-7.69 (m, 2H), 7.63-7.58 (m, 3H), 7.14 (s, 1H), 7.09-7.08, (d, J=3.73 Hz, 1H), 5.21-5.20 (d, J=7.05 Hz, 1H), 4.38-4.32 (q, J=7.05, 1H), 4.25-4.22 (d, J=12.85 Hz, 1H), 4.06-4.03 (d, J=12.85 Hz, 1H), 3.93-3.87 (m, 1H), 3.80 (s, 3H), 3.57-3.49 (m, 1H), 3.29 (s, 3H), 2.85-2.76 (m, 1H), 2.72-2.61 (m, 1H), 2.27-2.21 (m,1H), 1.69-1.64 (m, 1H), 0.53-0.49 (m, 1H). MS APCI: [M+H]⁺=378.2

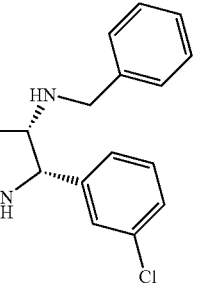

EXAMPLE 6 cis-Benzyl-[2-(3-chloro-phenyl)-pyrrolidin-3-yl]-amine dihydrobromide

A mixture of cis-3-amino-2-(3-chloro-phenyl)-pyrrolidine-1-carboxylic acid benzyl ester p-toluenesulfonate (0.32 mmol), obtained from preparatory example 7, benzaldehyde (0.034 g, 0.34 mmol), and sodium triacetoxyborohydride (0.082 g, 0.38 mmol) was stirred in 3 mL of methylene chloride at rt for 16 h. The reaction was washed 1× with 1M NaOH, dried through cotton, and concentrated to give an oil. The oil was dissolved in acetic acid (1 mL) and a solution of 30% hydrogen bromide in acetic acid (0.302 g, 1.12 mmol) was added. The solution was stirred for 16 h and the resultant solids were collected, washed with ether, and concentrated under vacuum to give 0.08 2 g (50%) of the title compound. ¹H NMR (2HBr, CD₃OD) δ 7.72 (s, 1H), 7.63-7.54 (m, 3H), 7.41 (s, 5H), 5.27-5.25 (d, J=7.47 Hz, 1H), 4.39-4.34 (q, J=7.89 Hz, 1H), 4.32-4.29 (d, J=12.86 Hz, 1H), 4.11-4.07 (d, J=12.86 Hz, 1H), 3.97-3.90 (ddd, J=12.0, 9.55, 3.32 Hz, 1H), 3.60-3.53 (m, 1H), 2.83-2.77 (m, 1H), 2.62-2.54 (m, 1H). MS APCI [M+H]⁺=287.3.

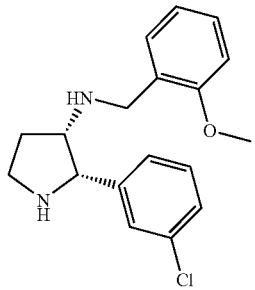

EXAMPLE 7 cis-[2-(3-Chloro-phenyl)-pyrrolidin-3-yl]-(2-methoxy-benzyl)-amine dihydrobromide A mixture of cis-3-amino-2-(3-chloro-phenyl)-pyrrolidine-1-carboxylic acid benzyl ester p-toluenesulfonate (0.32 mmol), obtained from preparatory example 7,2-methoxybenzaldehyde (0.034 g, 0.34 mmol), and sodium triacetoxyborohydride (0.082 g, 0.38 mmol) was stirred in 3 mL of methylene chloride at rt for 16 h. The reaction was washed 1× with 1M NaOH, dried through cotton, and concentrated to give an oil. The oil was dissolved in acetic acid (1 mL) and a solution of 30% hydrogen bromide in acetic acid (0.302 g, 1.12 mmol) was added. The solution was stirred for 16 h and the resultant solids were collected, washed with ether, and concentrated under vacuum. Trituration with hot isopropanol provided 0.082 g (50%) of title compound. ¹H NMR (2HBr, CD₃OD) δ 7.72 (s, 1H), 7.63-7.59 (m, 3H), 7.44-7.40 (t, J=7.89 Hz, 1H), 7.31-7.29 (d, J=7.48 Hz, 1H), 7.04-7.02 (d, J=8.31 Hz, 1H), 6.99-6.96 (t, J=7.48 Hz, 1H), 5.25-5.23 (d, J=7.47 Hz, 1H), 4.39-4.33 (q, J=7.47 Hz, 1H), 4.26-4.23 (d, J=12.86 Hz, 1H), 4.13-4.10 (d, J=12.86 Hz, 1H), 3.93-3.87 (ddd, J=12.0, 9.55, 3.74 Hz, 1H), 3.81 (s, 3H), 3.59-3.51 (m, 1H), 2.81-2.74 (m,1H), 2.66-2.58 (m, 1H). MS APCI: [M+H]⁺=317.3

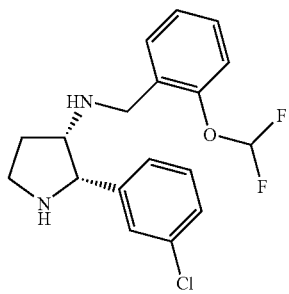

EXAMPLE 8 cis-[2-(3-Chloro-phenyl)-pyrrolidin-3-yl]-(2-difluoromethoxy-benzyl)-amine dihydrochloride A mixture of cis-3-amino-2-(3-chloro-phenyl)-pyrrolidine-1-carboxylic acid benzyl ester p-toluenesulfonate (0.32 mmol), obtained from preparatory example 7,2-difluoromethoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated to give 0.131 g of the title compound as a yellow oil. The dihydrochloride salt was prepared by addition of conc. HCl to free base in isopropanol and concentration under vacuum. Crystallize from ethyl acetate/isopropanol yielded Silica gel chromatography using CH₂Cl₂/methanol (9:1) gave 0.066 g (51%) of the title compound as a yellow oil. The dihydrochloride salt was generated via addition of concentrated HCl to free base in isopropanol to give 0.078 g of a white powder. ¹H NMR (2HCl, CD₃OD) δ 7.73 (s, 1H), 7.64-7.47 (m, 5H), 7.28-7.23 (m, 2H), 7.14-6.78 (t, J=73.0 Hz, 1H), 5.17-5.15 (d, J=7.05 Hz, 1H), 4.32-4.29 (m, 3H), 4.12-4.08 (d, J ×13.7 Hz, 1H), 3.93-3.88 (m, 1H), 3.58-3.50 (m, 1H), 2.90-2.81 (m, 1H), 2.70-2.62 (m, 1H). MS APCI: [M+H]⁺=353.1

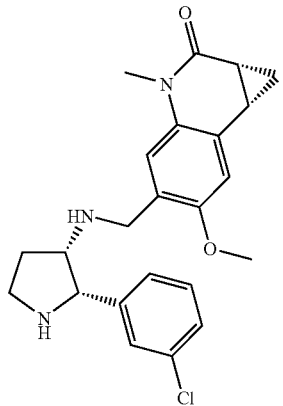

EXAMPLE 9 cis-5-{[2-(3-Chloro-phenyl)-pyrrolidin-3-ylamino]-methyl}-6-methoxy-3-methyl-1,1a,3,7b-tetrahydro-3-aza-cycloproparalnaphthalen-2-one dihydrobromide A mixture of cis-3-amino-2-(3-chloro-phenyl)-pyrrolidine-1-carboxylic acid benzyl ester p-toluenesulfonate (0.15 g, 0.32 mmol), obtained from preparatory example 7,6-methoxy-3-methyl-2-oxo-1a,2,3,7b-tetrahydro-1H-3-aza-cyclopropa[a]naphthalene-5-carbaldehyde (0.078 g, 0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated to give the title compound. Trituration with hot isopropanol to give 0.253 g of a white solid (73%). ¹H NMR (2HCl, CD₃OD) δ 7.75-7.74 (d, J=2.07 Hz, 1H), 7.66-7.57 (m, 3H), 7.16-7.15 (m, 2H), 5.28-5.26 (d, J=7.46 Hz, 1H), 4.46-4.39 (m, 1H), 4.32-4.29 (d, J=12.85 Hz, 1H), 4.18-4.14 (d, J=12.85 Hz, 1H), 3.95-3.89 (m, 1H), 3.85 (s, 3H), 3.60-3.53 (m, 1H), 3.30 (s, 3H), 2.85-2.82 (m, 1H), 2.70-2.60 (m, 1H), 2.27-2.22 (m,1H), 1.70-1.64 (m, 1H), 0.55-0.50 (m, 1H). MS APCI: [M+H]⁺=412.1

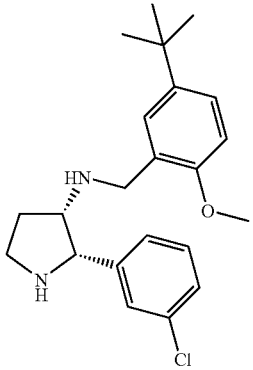

EXAMPLE 10 cis-(5-tert-butyl-2-methoxy-benzyl)-[2-(3-chloro-phenyl)-Pyrrolidin-3-yl]-amine dihydrochloride A mixture of cis-3-amino-2-(3-chloro-phenyl)-pyrrolidine-1-carboxylic acid benzyl ester p-toluenesulfonate (0.15 g, 0.32 mmol), obtained from preparatory example 7,5-tert-butyl-2-methoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated to give the title compound. The dihydrochloride salt was prepared via the addition of conc. HCl to free base in isopropanol to give 0.142 g of a white powder. ¹H NMR (2HCl, CD₃OD) δ 7.80 (s, 1H), 7.67 (s, 1H), 7.58 (s, 2H), 7.44-7.42, (d, J=8.31 Hz, 1H), 7.36 (s, 1H), 1H), 6.95-6.93 (d, J=8.72 Hz, 1H), 5.22-5.21 (d, J=7.05 Hz, 1H), 4.39-4.33 (m, 1H), 4.25-4.22 (d, J=13.0 Hz, 1H), 4.05-4.02 (d, J=13.0 Hz, 1H), 3.90-3.85 (m, 1H), 3.78 (s, 3H), 3.55-3.47 (m, 1H), 2.81-2.62 (m, 2H), 1.27 (s, 9H). MS APCI: [M+H]⁺=373.4

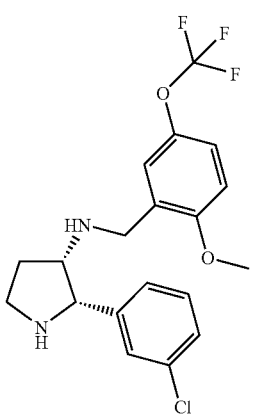

EXAMPLE 11 cis-[2-(3-Chloro-phenyl)-pyrrolidin-3-yl]-(2-methoxy-5-trifluoromethoxy-benzyl)-amine dihydrochloride A mixture of cis-3-amino-2-(3-chloro-phenyl)-pyrrolidine-1-carboxylic acid benzyl ester p-toluenesulfonate (0.15 g, 0.32 mmol), obtained from preparatory example 7,2-methoxy-5-trifluoromethoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated to give the title compound. The dihydrochloride salt was prepared via the addition of concd. HCl to free base in isopropanol to give 0.099 g of a white powder. ¹H NMR (2HCl, CD₃OD) δ 7.78 (s, 1H), 7.66-7.56 (m, 3H), 7.37-7.29 (m, 2H), 7.13-7.11 (d, J=9.40 Hz, 1H), 5.19-5.17 (d, J=6.64 Hz, 1H), 4.36-4.33 (m, 1H), 4.27-4.23 (d, J=13.27 Hz, 1H), 4.06-4.03 (d, J=13.27 Hz, 1H), 3.93-3.88 (m, 1H), 3.86 (s, 3H), 3.56-3.48 (m, 1H), 2.83-2.74 (m, 1H), 2.70-2.61 (m, 1H). MS APCI: [M+H]⁺=401.1

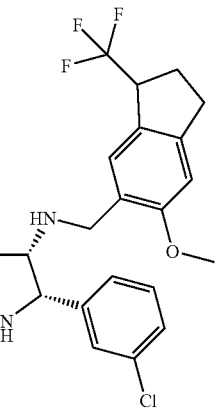

EXAMPLE 12 cis-[2-(3-Chloro-phenyl)-pyrrolidin-3-yl]-(6-methoxy-3-trifluoromethyl-indan-5-ylmethyl)-amine dihydrochloride A mixture of cis-3-amino-2-(3-chloro-pheny)l-pyrrolidine-1-carboxylic acid benzyl ester p-toluenesulfonate (0.15 g, 0.32 mmol), obtained from preparatory example 7,6-methoxy-3-trifluoromethyl-indan-5-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated to give the title compound. The dihydrochloride salt was prepared via the addition of concd. HCl to free base in isopropanol to give 0.092 g of a white powder. ¹H NMR (2HCl, CD₃OD) δ 7.77 (d, J=11.6 Hz, 1H), 7.63 (s, 1H), 7.58 (s, 2H), 7.30-7.26 (d, J=14.5 Hz, 1H), 6.98 (s, 1H), 5.19-5.16 (m, 1H), 4.35-4.31 (m, 1H), 4.23-4.20 (d, J=12.87 Hz, 1H), 4.09-3.98 (m, 1H), 3.90-3.82 (m, 2H), 3.81 (s, 3H), 3.54-3.46 (dd, J=11.2, 9.55 Hz, 1H), 3.07-3.01 (m, 1H), 2.98-2.90 (m, 1H), 2.77-2.71 (m, 1H), 2.68-2.62 (m, 1H), 2.41-2.36 (m, 1H), 2.26-2.19 (m, 1H). MS APCI: [M+H]⁺=425.3

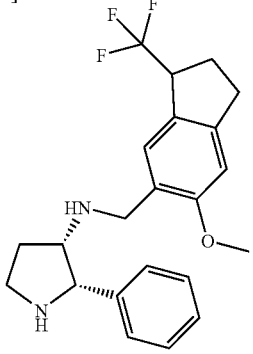

EXAMPLE 13 cis-(6-Methoxy-3-trifluoromethyl-indan-5-ylmethyl)-(2-phenyl-pyrrolidin-3-yl)-amine dihydrochloride A mixture of cis-3-amino-2-phenyl-pyrrolidine-1-carboxylic acid benzyl ester p-toluenesulfonate (0.15 g, 0.32 mmol), obtained from preparatory example 6,6-methoxy-3-trifluoromethyl-indan-5-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated to give the title compound. The dihydrochloride salt was prepared via the addition of concd. HCl to free base in isopropanol. Crystallization from ethyl acetate/methanol gave 0.040 g of a white powder. ¹H NMR (2HCl, CD₃OD) δ 7.68-7.56 (m, 5H), 7.27-7.24 (d, J=13.27 Hz, 1H), 6.98 (s, 1H), 5.20-5.18 (d, J=7.05 Hz, 1H), 4.3-4.31 (m, 1H), 4.22-4.16 (dd, J=12.85, 9.70 Hz, 1H), 4.04-3.97 (dd, J=16.1, 12.85, 1H), 3.91-3.86 (m, 2H), 3.77 (s, 3H), 3.56-3.49 (dd, J=19.2, 9.55 Hz, 1H), 3.10-3.02 (m, 1H), 2.98-2.91 (m, 1H), 2.78-2.70 (m, 1H), 2.68-2.61 (m, 1H), 2.44-2.34 (m, 1H), 2.27-2.19 (m, 1H). MS APCI: [M+H]⁺=391.2

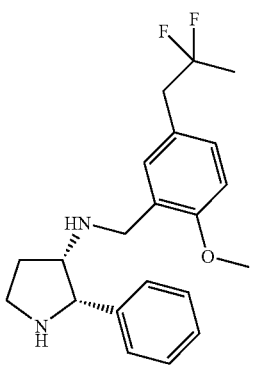

EXAMPLE 14 cis-[5-(2,2-Difluoro-propyl)-2-methoxy-benzyl]-(2-phenyl-pyrrolidin-3-yl)-amine dihydrochloride A mixture of cis-3-amino-2-phenyl-pyrrolidine-1-carboxylic acid benzyl ester p-toluenesulfonate (0.15 g, 0.32 mmol), obtained from preparatory example 6,5-(2,2-difluoro-propyl)-2-methoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated to give the title compound. The dihydrochloride salt was prepared via the addition of concd. HCl to free base in isopropanol, and crystallization from ethyl acetate/methanol gave 0.040 g of a white powder. ¹H NMR (2HCl, CD₃OD) δ 7.70-7.68 (m, 2H), 7.64-7.56 (m, 3H), 7.35-7.32 (d, J=8.29 Hz, 1H), 7.20 (s, 1H), 7.00-6.98 (d, J=8.71 Hz, 1H), 5.22-5.20 (d, J=7.05 Hz, 1H), 4.36-4.31 (q, J=13.89, 7.26 Hz, 1H), 4.22-4.19 (d, J=13.27 Hz, 1H), 4.03-4.00 (d, J=13.27 Hz, 1H), 3.92-3.86 (ddd, J=12.23, 9.12, 3.32 Hz, 1H), 3.76 (s, 3H), 3.56-3.49 (m, 1H), 3.14-3.06 (t, J=15.97 Hz, 2H), 2.81-2.74 (m, 1H), 2.71-2.63 (m, 1H), 1.56-1.46 (t, J=18.25 Hz, 3H). MS APCI: [M+H]⁺=361.2

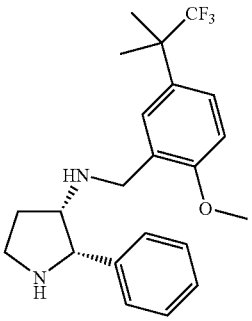

EXAMPLE 15 cis-[2-Methoxy-5-(2,2,2-trifluoro-1,1-dimethyl-ethyl)-benzyl]-(2-phenyl-pyrrolidin-3-yl)-amine dihydrochloride A mixture of cis-3-amino-2-phenyl-pyrrolidine-1-carboxylic acid benzyl ester p-toluenesulfonate (0.15 g, 0.32 mmol), obtained from preparatory example 6,2-methoxy-5-(2,2,2-trifluoro-1,1-dimethyl-ethyl)-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated to give the title compound. The dihydrochloride salt was prepared via the addition of concd. HCl to free base in isopropanol to give 0.15 g of title compound as a pink powder. ¹H NMR (2HCl, CD₃OD) δ 7.71-7.68 (m, 2H), 7.64-7.58 (m, 4H), 7.46 (s, 1H), 7.04-7.02 (d, J=8.71 Hz, 1H), 5.22-5.20 (d, J=7.05 Hz, 1H). 4.37-4.31 (dd, J=13.89, 7.20 Hz, 1H), 4.25-4.22 (d, J=12.87 Hz, 1H), 4.06-4.03 (d, J=12.87 Hz, 1H), 3.92-3.82 (m, 1H), 3.78 (s, 3H), 3.56-3.49 (m, 1H), 2.82-2.73 (m, 1H), 2.71-2.64 (m, 1H), 1.55 (s, 6H). MS APCI: [M+H]⁺=393.2

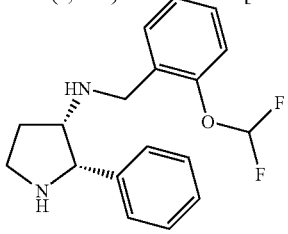

EXAMPLE 16 cis-(2-Difluoromethoxy-benzyl)-(2-phenyl-pyrrolidin-3-yl)-amine dihydrochloride

A mixture of cis-3-amino-2-phenyl-pyrrolidine-1-carboxylic acid benzyl ester p-toluenesulfonate (0.15 g, 0.32 mmol), obtained from preparatory example 6,2-difluoromethoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated. The dihydrochloride salt was prepared via the addition of concd. HCl to free base in isopropanol. Trituration with isopropanol gave 0.041 g of the title compound. ¹H NMR (2HCl, CD₃OD) δ 7.69-7.67 (m, 1H), 7.61-7.54 (m, 2H), 7.50-7.45 (m, 1H), 7.27-23 (m, 1H) 7.13-6.76, (t, J=73.2 Hz, 1H), 5.20-5.19 (d, J=6.64 Hz, 1H), 4.37-4.33 (m, 1H), 4.29-4.26 (d, J=13.45 Hz, 1H), 4.07-4.04 (d, J=13.45 Hz, 1H), 3.93-3.87 (m, 1H), 3.58-3.50 (m, 1H), 2.83-2.81 (m, 1H), 2.70-2.60 (m, 1H). MS APCI: [M+H]⁺=319.2

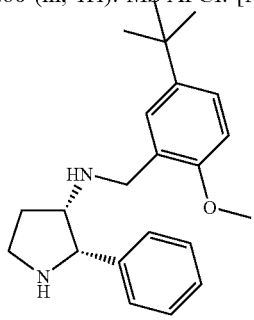

EXAMPLE 17 cis-(5-tert-Butyl-2-methoxy-benzyl)-(2-phenyl-pyrrolidin-3-yl)-amine dihydrochloride A mixture of cis-3-amino-2-phenyl-pyrrolidine-1-carboxylic acid benzyl ester p-toluenesulfonate (0.15 g, 0.32 mmol), obtained from preparatory example 6, 5-tert-butyl-2-methoxy-benzylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated. The dihydrochloride salt was prepared via the addition of concd. HCl to free base in isopropanol. Trituration with diethyl ether/isopropanol gave 0.049 g of title compound as a white powder. ¹H NMR (2HCl, CD₃OD) δ 7.68-7.56 (m, 5H), 7.46-7.43 (m, 1H), 7.30 (s, 1H), 6.95-6.93 (d, J=8.71 Hz, 1H), 5.20-5.18 (d, J=7.46 Hz, 1H), 4.33-4.28 (m, 1H), 4.23-4.19 (d, J=13.27 Hz, 1H), 4.05-4.02 (d, J=13.27 Hz, 1H), 3.92-3.86 (ddd, J=12.13, 9.08, 3.42 Hz, 1H), 1H), 3.73 (s, 3H), 3.56-3.46 (m, 1H), 2.83-2.72 (m, 1H), 2.69-2.59 (m, 1H), 1.28 (s, 9H). MS APCI: [M+H]⁺=339.3

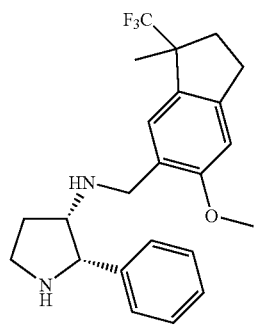

EXAMPLE 18 cis-(6-Methoxy-3-methyl-3-trifluoromethyl-indan-5-ylmethyl)-(2-phenyl-pyrrolidin-3-yl)-amine dihydrochloride A mixture of cis-3-amino-2-phenyl-pyrrolidine-1-carboxylic acid benzyl ester p-toluenesulfonate (0.15 g, 0.32 mmol), obtained from preparatory example 6,6-Methoxy-3-methyl-3-trifluoromethyl-indan-5-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH₂Cl₂. The combined extracts were dried through cotton and concentrated. The dihydrochloride salt was prepared via the addition of concd. HCl to free base in isopropanol. Crystallization from ethyl acetate/methanol to give 0.079 g of the title compound. ¹H NMR (2HCl, CD₃OD) δ 7.66-7.58 (m, 5H), 7.22-7.18 (d, J=12.44 Hz, 1H), 6.95 (s, 1H), 5.20-5.18 (d, J=5.39 Hz, 1H), 4.33-4.30 (m, 1H), 4.22-4.16 (t, J=12.23 Hz, 1H), 4.04-3.97 (t, J=13.06 Hz, 1H), 3.91-3.86 (m, 1H), 3.76 (s, 3H), 3.56-3.49 (m, 1H), 3.03-2.95 (m, 2H), 2.75-2.71 (m, 1H), 2.67-2.61 (m, 1H), 2.53-2.46 (m, 1H), 2.04-1.96 (m, 1H), 1.45 (s, 3H).

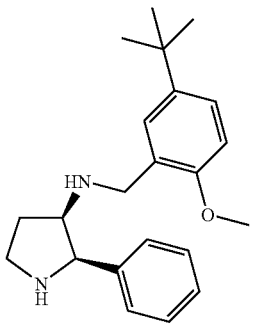

EXAMPLE 19 cis-(5-tert-Butyl-2-methoxy-benzyl)-([2R, 3R]-2-phenyl-pyrrolidin-3-yl)-amine dihydrochloride A mixture of cis-3-amino-2-phenyl-pyrrolidine-1-carboxylic acid benzyl ester p-toluenesulfonate (0.15 g, 0.32 mmol), obtained from preparatory example 6,5-tert-butyl-2-methoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated. The dihydrochloride salt was prepared via the addition of concd. HCl to free base in isopropanol to give 0.045 g of the title compound. $^1$H NMR (2HCl, $CD_3OD$) δ 7.67-7.64 (m, 2H), 7.60-7.55 (m, 3H), 7.42-7.40 (dd, J=8.71, 2.49 Hz, 1H), 7.28 (s, 1H), 6.92-6.90 (d, J=8.71 Hz, 1H), 5.18-5.16 (d, J=7.05 Hz, 1H), 4.32-4.27 (q, J=7.05 Hz, 1H), 4.20-4.17 (d, J=13.06 Hz, 1H), 4.01-3.98 (d, J=13.06 Hz, 1H), 3.89-3.83 (ddd, J=12.13, 9.02, 3.32 Hz, 1H), 3.70 (s, 3H), 3.53-3.46 (m, 1H), 2.78-2.70 (m, 1H), 2.67-2.58 (m, 1H), 1.25 (s, 9H). MS APCI: $[M+H]^{30}$=339.2

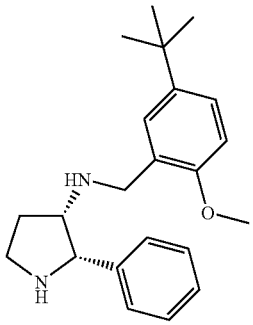

EXAMPLE 20 cis-(5-tert-Butyl-2-methoxy-benzyl)-([2S, 3S]2-phenyl-pyrrolidin-3-yl)-amine dihydrochloride A mixture of cis-3-amino-2-phenyl-pyrrolidine-1-carboxylic acid benzyl ester p-toluenesulfonate (0.15 g, 0.32 mmol), obtained from preparatory example 6,5-tert-butyl-2-methoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated. The dihydrochloride salt was prepared via the addition of concd. HCl to free base in isopropanol to give 0.062 g of the title compound. $^1$H NMR (2HCl, $CD_3OD$) δ 7.67-7.64 (m, 2H), 7.61-7.54 (m, 3H), 7.42-7.40 (dd, J=8.71, 2.49 Hz, 1H), 7.28 (s, 1H), 6.92-6.90 (d, J=8.71 Hz, 1H), 5.18-5.16 (d, J=7.46 Hz, 1H), 4.31-4.26 (q, J=7.05 Hz, 1H), 4.20-4.16 (d, J=12.86 Hz, 1H), 4.00-3.97 (d, J=12.86 Hz, 1H), 3.90-3.83 (ddd, J=12.13, 9.02, 3.32 Hz, 1H), 3.70 (s, 3H), 3.53-3.46 (m, 1H), 2.78-2.72 (m, 1H), 2.69-2.59 (m, 1H), 1.25 (s, 9H). MS APCI: $[M+H]^+$=339.3

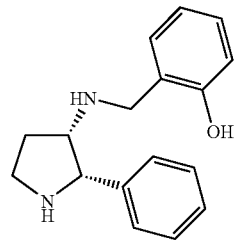

EXAMPLE 21 cis-2-[(2-Phenyl-pyrrolidin-3-ylamino)-methyl]-phenol dihydrochloride

A mixture of cis-3-amino-2-phenyl-pyrrolidine-1-carboxylic acid benzyl ester p-toluenesulfonate (0.15 g, 0.32 mmol), obtained from preparatory example 6,2-hydroxybenzaldeyde (0.34 mmol), and sodium triacetoxyborohydride (0.082 g, 0.38 mmol) was stirred in 3 mL of methylene chloride at rt for 16 h. The mixture was washed 1× with 1 M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated. The dihydrochloride salt was prepared via the addition of concd. HCl to free base in isopropanol. Crystallization from ethyl acetate/methanol to gave 0.042 g of the title compound. $^1$H NMR (2HCl, $CD_3OD$) δ 7.60-7.53 (m, 5H), 7.25-7.21 (m, 3H), 7.18-7.16 (dd, J=7.88, 1.66 Hz, 1H), 6.85-6.79 (m, 1H), 5.20-5.18 (d, J=7.46 Hz, 1H), 4.31-4.26 (q, J=7.46 Hz, 1H), 4.22-4.19 (d, J=13.27 Hz, 1H), 4.09-4.06 (d, J=13.27 Hz, 1H), 3.89-3.83 (ddd, J=12.13, 9.02, 3.32 Hz, 1H), 3.54-3.47

(m, 1H), 3.31 (s, 1H), 2.80-2.72 (m, 1H), 2.65-2.55 (m, 1H). MS APCI: [M+H]$^+$=269.2

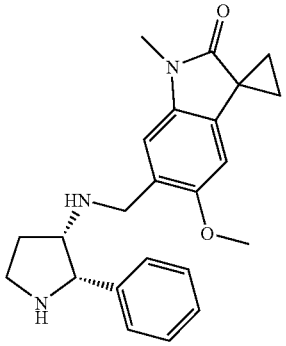

EXAMPLE 22 cis-3-Amino-2-phenyl-pyrrolidine-1-carboxylic acid benzyl ester p-toluenesulfonate A mixture of cis-3-amino-2-phenyl-pyrrolidine-1-carboxylic acid benzyl ester p-toluenesulfonate (0.15 g, 0.32 mmol), obtained from preparatory example 6,5-methoxy-1-methyl-3,3-spirocyclopropyl-2-oxo-2,3-dihydro-1 H-indole-6-carbaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH$_2$Cl$_2$. The combined extracts were dried through cotton and concentrated. The dihydrochloride salt was prepared via the addition of concd. HCl to free base in isopropanol. Crystallization from ethyl acetate/methanol gave 0.047 g of the title compound. $^1$H NMR (2HCl, CD$_3$OD) δ 7.66-7.53 (m, 5H), 6.96 (s, 1H), 6.75 (s, 1H), 5.18-5.16 (d, J=7.46 Hz, 1H), 4.34-4.29 (m, 1H), 4.26-4.22 (d, J=13.06 Hz, 1H), 4.07-4.04 (d, J=13.06 Hz, 1H), 3.90-3.84 (m, 1H), 3.71 (s, 3H), 3.54-3.46 (m, 1H), 3.23 (s, 3H), 2.77-2.72 (m, 1H), 2.69-2.60 (m, 1H), 1.64 (s, 4H). MS APCI: [M+H]$^+$=3.78.3

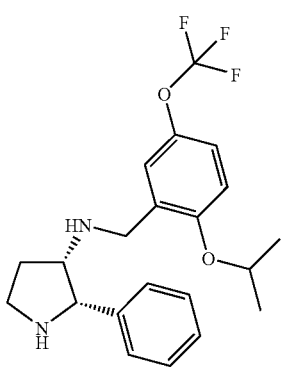

EXAMPLE 23 cis-(2-Isopropoxy-5-trifluoromethoxy-benzyl)-(2-phenyl-pyrrolidin-3-yl)-amine dihydrochloride A mixture of cis-3-amino-2-phenyl-pyrrolidine-1-carboxylic acid benzyl ester p-toluenesulfonate (0.15 g, 0.32 mmol), obtained from preparatory example 6,2-isopropoxy-5-trifluoromethoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH$_2$Cl$_2$. The combined extracts were dried through cotton and concentrated. The dihydrochloride salt was prepared via the addition of concd. HCl to free base in isopropanol. Crystallization from ethyl acetate/methanol gave 0.030 g of the title compound. $^1$H NMR (2HCl, CD$_3$OD) δ 7.67-7.65 (m, 2H), 7.58-7.53 (m, 3H), 7.30-7.28 (m, 2H), 7.11-7.08 (d, J=8.71 Hz, 1H), 5.17-5.15 (d, J=7.05 Hz, 1H), 4.67-4.64 (m, 1H), 4.34-4.30 (m, 1H), 4.24-4.21 (d, J=13.27 Hz, 1H), 4.05-4.02 (d, J=13.27 Hz, 1H), 3.89-3.85 (ddd, J=12.13, 9.02, 3.32 Hz, 1H), 3.53-3.46 (m, 1H), 2.85-2.75 (m, 1H), 2.70-2.60 (m, 1H), 1.30-1.27 (t, J=6.0 Hz, 6H). MS APCI: [M+H]$^+$=395.3

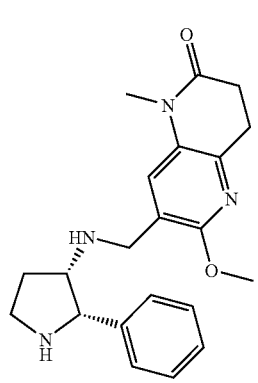

EXAMPLE 24 cis-6-Methoxy-1-methyl-7-[(2-phenyl-pyrrolidin-3-ylamino)-methyl]-3,4-dihydro-1H-[1,5]naphthyridin-2-one dihydrochloride A mixture of cis-3-amino-2-phenyl-pyrrolidine-1-carboxylic acid benzyl ester p-toluenesulfonate (0.15 g, 0.32 mmol), obtained from preparatory example 6,2-methoxy-5-methyl-6-oxo-5,6,7,8-tetrahydro-[1,5]naphthyridine-3-carbaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH$_2$Cl$_2$. The combined extracts were dried through cotton and concentrated. The dihydrochloride salt was prepared via the addition of concd.

HCl to the free base in isopropanol. Crystallization from ethyl acetate/methanol gave 0.051 g of the title compound. $^1$H NMR (2HCl, CD$_3$OD) δ 7.70-7.68 (m, 2H), 7.61-7.54 (m, 3H), 7.50 (s, 1H), 5.19-5.17 (d, J=7.05 Hz, 1H), 4.36-4.32 (m, 1H), 4.22-4.18 (d, J=13.27 Hz, 1H), 4.01-3.97 (d, J=13.27 Hz, 1H), 3.91-3.86 (m, 1H), 3.84 (s, 3H), 3.55-3.48 (m, 1H), 3.27 (s, 3H), 2.99-2.96 (t, J=7.68 Hz, 2H), 2.81-2.77 (m, 1H), 2.71-2.64 (m, 3H). MS APCI: [M+H]$^+$=367.3

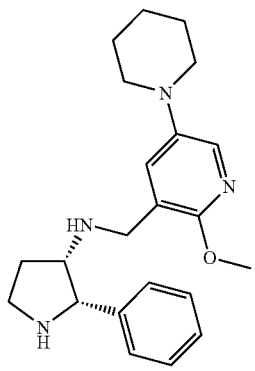

EXAMPLE 25 cis-(6'-Methoxy-3,4,5,6-tetrahydro-2H-[1,3']bipyridinyl-5'-ylmethyl)-(2-phenyl-pyrrolidin-3-yl)-amine dihydrochloride A mixture of cis-3-amino-2-phenyl-pyrrolidine-1-carboxylic acid benzyl ester p-toluenesulfonate (0.15 g, 0.32 mmol), obtained from preparatory example 6,6'-methoxy-3,4,5,6-tetrahydro-2H-[1,3]bipyridinyl-5'-ylmethylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH$_2$Cl$_2$. The combined extracts were dried through cotton and concentrated. The dihydrochloride salt was prepared via the addition of concd. HCl to free base in isopropanol. Crystallization from ethyl acetate/methanol gave 0.022 g of the title compound. MS APCI: [M+H]$^+$=367.2

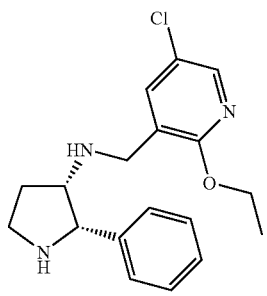

EXAMPLE 26 cis-(5-Chloro-2-ethoxy-pyridin-3-ylmethyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6,5-chloro-2-ethoxy-pyridin-3-ylmethylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH$_2$Cl$_2$. The combined extracts were dried through cotton and concentrated to yield the title compound. M/Z: 331.145

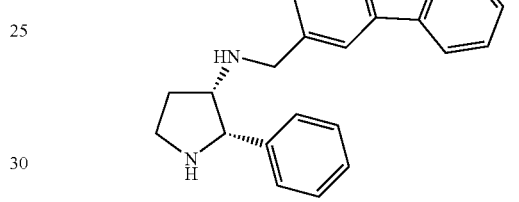

EXAMPLE 27 cis-Dibenzofuran-2-ylmethyl-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, dibenzofuran-2-ylmethylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH$_2$Cl$_2$. The combined extracts were dried through cotton and concentrated to yield the title compound. M/Z: 342.173

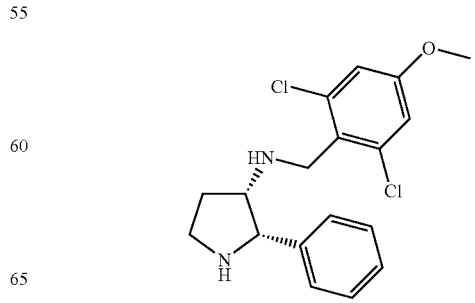

EXAMPLE 28 cis-(2,6-Dichloro-4-methoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2,6-Dichloro-4-methoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 350.095

EXAMPLE 30 cis-(6-Methoxy-2-methyl-benzothiazol-5-ylmethyl)-(2-phenyl-pyrrolidin-3-yl)-amine A mixture of cis-3-amino-2-phenyl-pyrrolidine-1-carboxylic acid benzyl ester p-toluenesulfonate (0.15 g, 0.32 mmol), obtained from preparatory example 6,6-methoxy-2-methyl-benzothiazol-5-ylmethylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 353.156

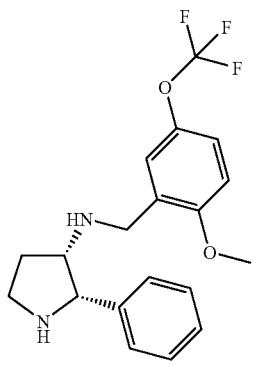

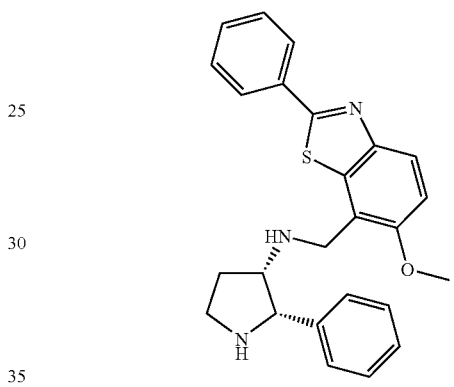

EXAMPLE 29 cis-(2-Methoxy-5-trifluoromethoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6,2-methoxy-5-trifluoromethoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 366.155

EXAMPLE 31 cis-(6-Methoxy-2-phenyl-benzothiazol-7-ylmethyl)-(2-phenyl-pyrrolidin-3-yl)-amine A mixture of cis-3-amino-2-phenyl-pyrrolidine-1-carboxylic acid benzyl ester p-toluenesulfonate (0.15 g, 0.32 mmol), obtained from preparatory example 6,6-methoxy-2-phenyl-benzothiazol-7-ylmethylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 415.171

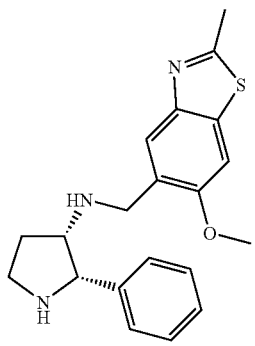

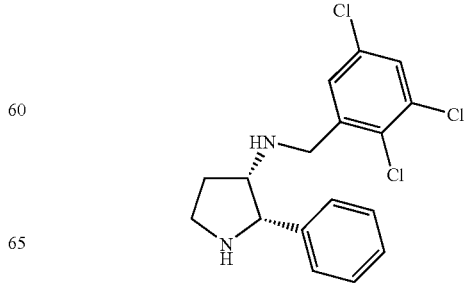

EXAMPLE 32 cis-(2-Phenyl-pyrrolidin-3-yl)-(2,3,5-trichloro-benzyl)-amine

A mixture of cis-3-amino-2-phenyl-pyrrolidine-1-carboxylic acid benzyl ester p-toluenesulfonate (0.15 g, 0.32 mmol), obtained from preparatory example 6, 2,3,5-trichloro-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 354.045

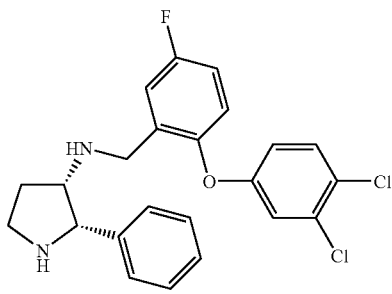

EXAMPLE 33 cis-[2-(3,4-Dichloro-phenoxy)-5-fluoro-benzyl]-(2-phenyl-pyrrolidin-3-yl)-amine A mixture of cis-3-amino-2-phenyl-pyrrolidine-1-carboxylic acid benzyl ester p-toluenesulfonate (0.15 g, 0.32 mmol), obtained from preparatory example 6, 2-(3,4-dichloro-phenoxy)-5-fluoro-benzaldehyde (0.34 mmol), and sodium triacetoxyborohydride (0.082 g, 0.38 mmol) was stirred in 3 mL of methylene chloride at rt for 16 h. The mixture was washed 1× with 1 M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 430.101

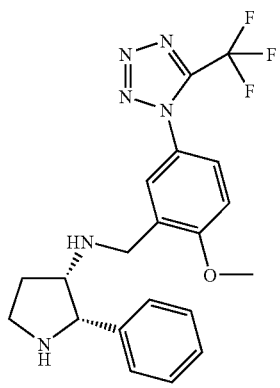

EXAMPLE 34 cis-[2-Methoxy-5-(5-trifluoromethyl-tetrazol-1-yl)-benzyl]-(2-phenyl-pyrrolidin-3-yl)-amine A mixture of cis-3-amino-2-phenyl-pyrrolidine-1-carboxylic acid benzyl ester p-toluenesulfonate (0.15 g, 0.32 mmol), obtained from preparatory example 6,2-methoxy-5-(5-trifluoromethyl-tetrazol-1-yl)-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 418.172.

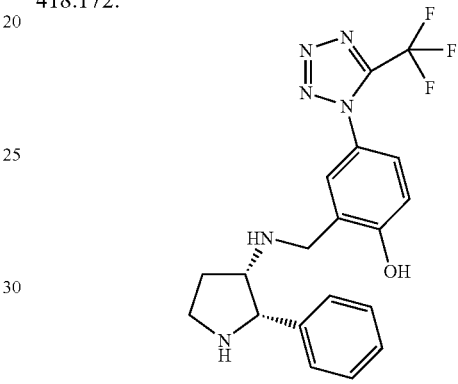

EXAMPLE 35 cis-2-[(2-Phenyl-pyrrolidin-3-ylamino)-methyl]-4-(5-trifluoromethyl-tetrazol-1-yl)-phenol A mixture of cis-3-amino-2-phenyl-pyrrolidine-1-carboxylic acid benzyl ester p-toluenesulfonate (0.15 g, 0.32 mmol), obtained from preparatory example 6, (2-phenyl-pyrrolidin-3-ylamino)-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 418.172

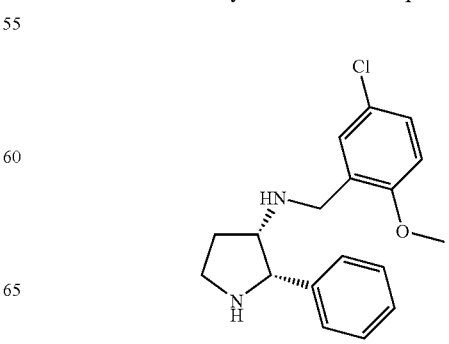

EXAMPLE 36 cis-(5-Chloro-2-methoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 5-chloro-2-methoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 316.134

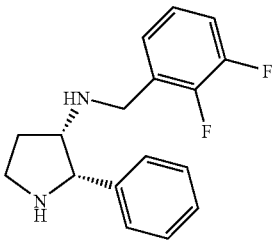

EXAMPLE 37 cis-(2,3-Difluoro-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2,3-difluoro-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 288.143

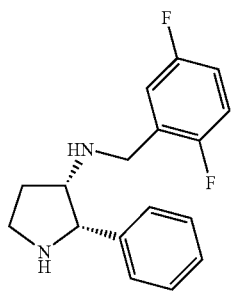

EXAMPLE 38 cis-(2,5-Difluoro-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2,5-difluoro-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 288.143

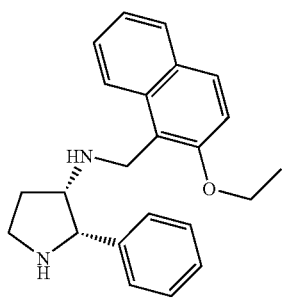

EXAMPLE 39 cis-(2-Ethoxy-naphthalen-1-ylmethyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2-ethoxy-naphthalen-1-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 346.204.

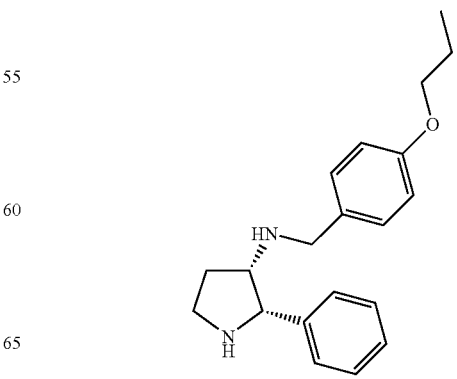

EXAMPLE 40 cis-(2-Phenyl-pyrrolidin-3-yl)-(4-propoxy-benzyl)-amine

A mixture of cis-3-amino-2-phenyl-pyrrolidine-1-carboxylic acid benzyl ester p-toluenesulfonate (0.15 g, 0.32 mmol), obtained from preparatory example 6, 4-propoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 310.204

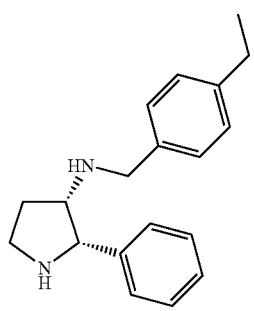

EXAMPLE 41 cis-(4-Ethyl-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 4-ethyl-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1 M HCl, washed 2× with diethyl ether, basified with 6 M NaOH, and extracted 3× with $CH_2Cl_2$. The combined extracts were dried through cotton and concentrated to yield the title compound. M/Z: 280.193

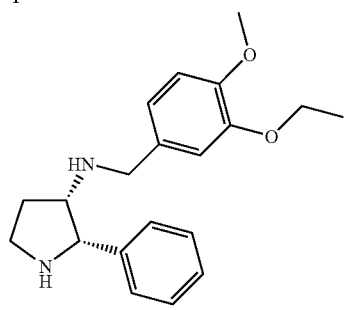

EXAMPLE 42 cis-(3-Ethoxy-4-methoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 3-ethoxy-4-methoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 326.199

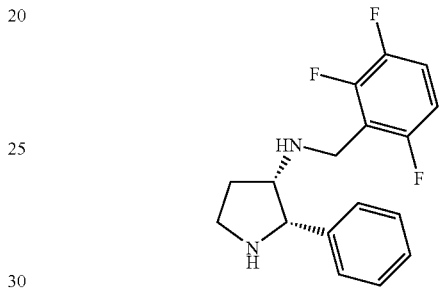

EXAMPLE 43 cis-(2-Phenyl-pyrrolidin-3-yl)-(2,3,6-trifluoro-benzyl)-amine

A mixture of cis-3-amino-2-phenyl-pyrrolidine-1-carboxylic acid benzyl ester p-toluenesulfonate (0.15 g, 0.32 mmol), obtained from preparatory example 6, 2,3,6-trifluoro-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 306.134.

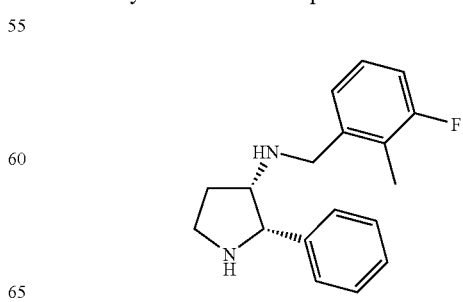

EXAMPLE 44 cis-(3-Fluoro-2-methyl-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 3-fluoro-2-methyl-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 284.168

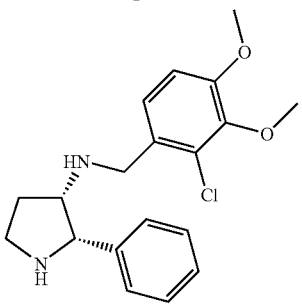

EXAMPLE 45 cis-(2-Chloro-3,4-dimethoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2-chloro-3,4-dimethoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 346.144

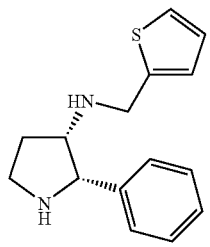

EXAMPLE 46 cis-(2-Phenyl-pyrrolidin-3-yl)-thiophen-2-ylmethyl-amine

A mixture of cis-3-amino-2-phenyl-pyrrolidine-1-carboxylic acid benzyl ester p-toluenesulfonate (0.15 g, 0.32 mmol), obtained from preparatory example 6, thiophene-2-carbaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 258.119

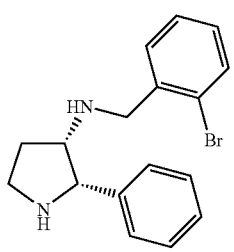

EXAMPLE 47 cis-(2-Bromo-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2-bromo-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 330.073

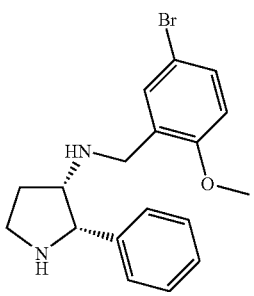

EXAMPLE 48 cis-(5-Bromo-2-methoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 5-bromo-2-methoxy-benzylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 360.083

EXAMPLE 49 cis-(5-Methyl-furan-2-ylmethyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 5-methyl-furan-2-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 256.157

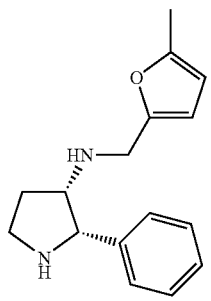

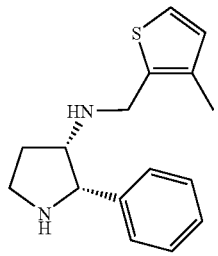

EXAMPLE 50 cis-(3-Methyl-thiophen-2-ylmethyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 3-methyl-thiophen-2-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 272.134

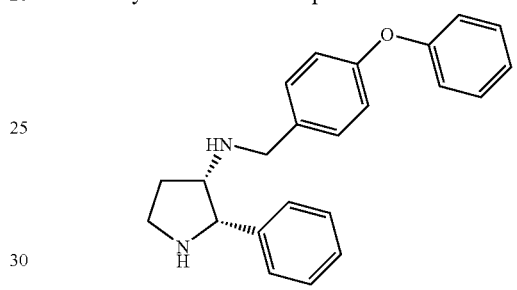

EXAMPLE 51 cis-(4-Phenoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 4-phenoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1 M HCl, washed 2× with diethyl ether, basified with 6 M NaOH, and extracted 3× with $CH_2Cl_2$. The combined extracts were dried through cotton and concentrated to yield the title compound. M/Z: 344.188

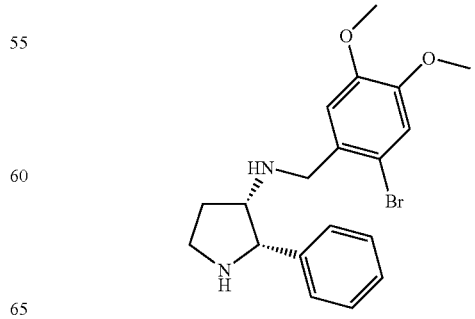

EXAMPLE 52 cis-(2-Bromo-4,5-dimethoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2-bromo-4,5-dimethoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 392.101

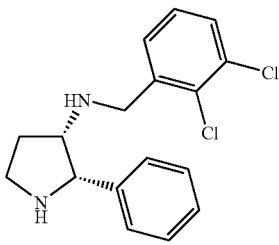

EXAMPLE 53 cis-(2,3-Dichloro-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2,3-dichloro-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 320.084

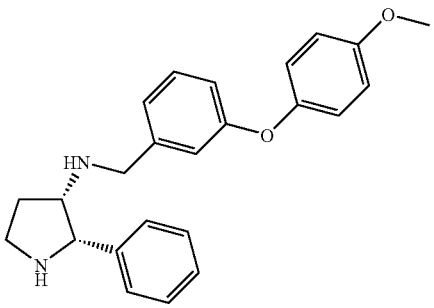

EXAMPLE 54 cis-[3-(4-Methoxy-phenoxy)-benzyl]-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 3-(4-methoxy-phenoxy)-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 374.199

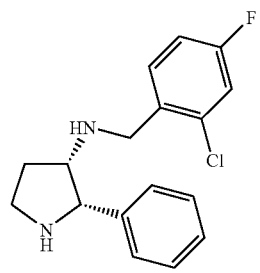

EXAMPLE 55 cis-(2-Chloro-4-fluoro-benzyl )-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2-chloro-4-fluoro-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 304.114

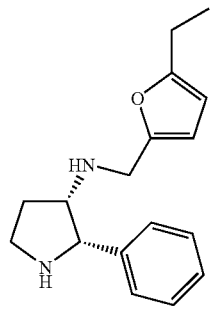

EXAMPLE 56 cis-(5-Ethyl-furan-2-ylmethyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 5-ethyl-furan-2-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH$_2$Cl$_2$. The combined extracts were dried through cotton and concentrated to yield the title compound. M/Z: 270.173

EXAMPLE 57 cis-(2-Chloro-quinolin-3-ylmethyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2-chloro-quinolin-3-methyaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with CH$_2$Cl$_2$. The combined extracts were dried through cotton and concentrated to yield the title compound. M/Z: 337.134

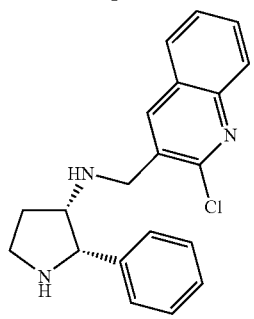

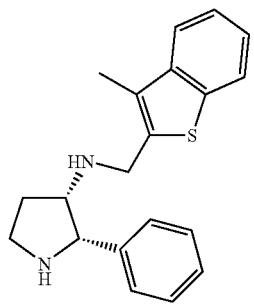

EXAMPLE 58 cis-(3-Methyl-benzo[b]thiophen-2-ylmethyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 3-methyl-benzo[b]thiophen-2-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1 M HCl, washed 2× with diethyl ether, basified with 6 M NaOH, and extracted 3× with CH$_2$Cl$_2$. The combined extracts were dried through cotton and concentrated to yield the title compound. M/Z: 322.150

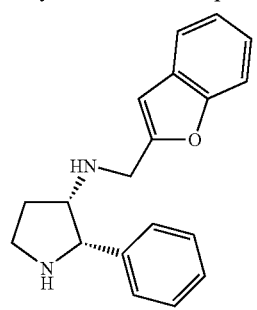

EXAMPLE 59 cis-Benzofuran-2-ylmethyl-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, benzofuran-2-methyl aldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1 M HCl, washed 2× with diethyl ether, basified with 6 M NaOH, and extracted 3× with CH$_2$Cl$_2$. The combined extracts were dried through cotton and concentrated to yield the title compound. M/Z: 292.157

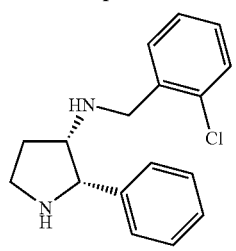

EXAMPLE 60 cis-(2-Chloro-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2-chlorobenzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 286.123

EXAMPLE 61 cis-(6-Methoxy-1-methyl-1-trifluoromethyl-isochroman-7-ylmethyl)-(2-phenyl-pyrrolidin-3-yl)-amine A mixture of cis-3-amino-2-phenyl-pyrrolidine-1-carboxylic acid benzyl ester p-toluenesulfonate (0.15 g, 0.32 mmol), obtained from preparatory example 6, 6-methoxy-1-methyl-1-trifluoromethyl-isochroman-7-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 420.202

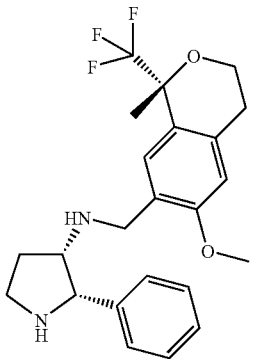

EXAMPLE 62 cis-2-Chloro-6-{3-[(2-phenyl-pyrrolidin-3-ylamino)-methyl]-phenoxy}-benzonitrile A mixture of cis-3-amino-2-phenyl-pyrrolidine-1-carboxylic acid benzyl ester p-toluenesulfonate (0.15 g, 0.32 mmol), obtained from preparatory example 6, 2-chloro-6-(3-formyl-phenoxy)-benzonitrile (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 403.145

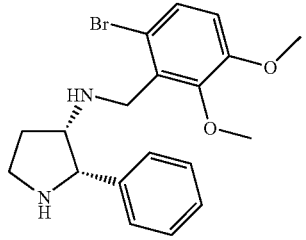

EXAMPLE 63 cis-(6-Bromo-2,3-dimethoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 6-bromo-2,3-dimethoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1 M HCl, washed 2× with diethyl ether, basified with 6 M NaOH, and extracted 3× with $CH_2Cl_2$. The combined extracts were dried through cotton and concentrated to yield the title compound. M/Z: 392.101

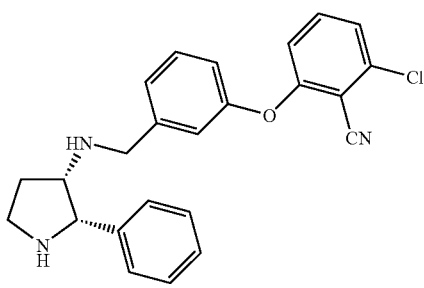

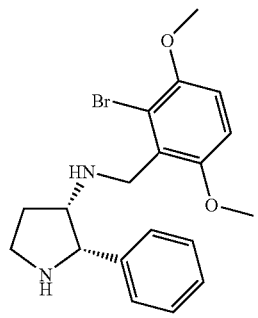

EXAMPLE 64 cis-(2-Bromo-3,6-dimethoxy-benzyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2-bromo-3,6-dimethoxy-benzaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 392.101

EXAMPLE 65 cis-(2,2-Dimethyl-chroman-6-ylmethyl)-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 2,2-Dimethyl-chroman-6-methylaldehyde (0.34 mmol), and sodium triacetoxyborohydride (0.082 g, 0.38 mmol) was stirred in 3 mL of methylene chloride at rt for 16 h. The mixture was washed 1× with 1M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 336.220

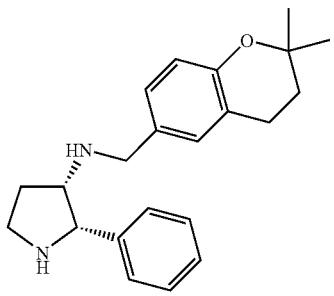

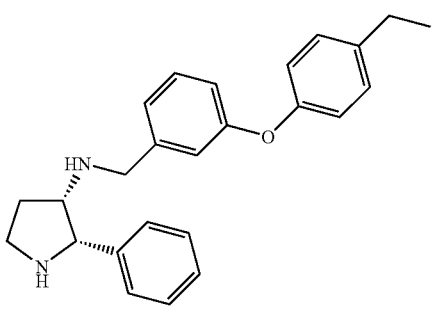

EXAMPLE 66 cis-[3-(4-Ethyl-phenoxy)-benzyl]-(2-phenyl-pyrrolidin-3-yl)-amine

A mixture of cis-3-amino-2-phenyl-pyrrolidine-1-carboxylic acid benzyl ester p-toluenesulfonate (0.15 g, 0.32 mmol), obtained from preparatory example 6, 3-(4-ethyl-phenoxy)-benzaldehyde (0.34 mmol), and sodium triacetoxyborohydride (0.082 g, 0.38 mmol) was stirred in 3 mL of methylene chloride at rt for 16 h. The mixture was washed 1× with 1 M NaOH and the organic solution was dried through cotton and concentrated to give an off-white foam. The foam was dissolved in acetic acid (1 mL) and a solution of 30% hydrogen bromide in acetic acid (0.302 g, 1.12 mmol) was added. After stirring for 16 h, the mixture was diluted with 1M HCl, washed 2× with diethyl ether, basified with 6 M NaOH, and extracted 3× with $CH_2Cl_2$. The combined extracts were dried through cotton and concentrated to yield the title compound. M/Z: 372.220

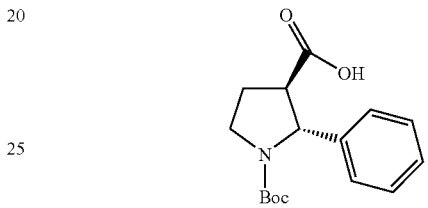

PREPARATORY EXAMPLE 8 trans-2-Phenyl-pyrrolidine-1,3-dicarboxylic acid 1-tert-butyl ester trans-2-Phenyl-pyrrolidine-1,3-dicarboxylic acid 1-tert-butyl ester 3-ethyl ester (obtained from preparatory example 3) (0.68 g, 2.13 mmol) was stirred in a solution of 10.5 mL of 1M NaOH and 10.5 mL of methanol at rt for 2 days. The mixture was concentrated, acidified with 6 M HCl (aq) to pH ~2, and extracted 3× with $CH_2Cl_2$. The combined extracts were dried through cotton, and concentrated. Silica gel chromatography eluting with hexanes/ethyl acetate (1:1) gave 0.58 g of a colorless oil. Crystallization from pet. ether/ether (ca. 10:1; 25 mL) gave 0.427 g (69%) of the title compound. MS APCI: $[M+H]^+$=292.1

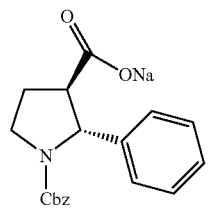

PREPARATORY EXAMPLE 9 trans-2-Phenyl-pyrrolidine-1,3-dicarboxylic acid 1-benzyl ester sodium salt trans-2-Phenyl-pyrrolidine-1,3-dicarboxylic acid 1-tert-butyl ester obtained from preparatory example 8 (10.1 g, 34.8 mmol) was stirred in 1,4-dioxane (145 mL) at 0° C. 6 M HCl (29 mL, 174 mmol) was added and the mixture was slowly warmed to rt and stirred for 16 h. The mixture was then cooled to 0° C. and solid $NaHCO_3$ was carefully added until the aqueous layer was saturated. Benzyl chloroformate was added and the mixture was stirred vigorously at 0° C.

for 1 hr, and at rt for 20 h. The suspension was then filtered and the solids were dried under vacuum to give 6.54 g (55%) of the title compound. MS APCI: [M+H]$^+$=326.1

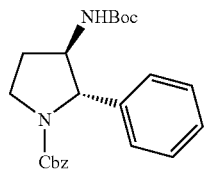

PREPARATORY EXAMPLE 10

Trans-3-tert-Butoxycarbonylamino-2-phenyl-pyrrolidine-1-carboxylic acid benzyl ester A mixture of trans-2-phenyl-pyrrolidine-1,3-dicarboxylic acid 1-benzyl ester sodium salt obtained from preparatory example 9 (6.28 g, 18.1 mmol) and diphenylphosphoryl azide (4.29 mL, 19.9 mmol) was stirred in 55 mL of tert-butyl alcohol at reflux for 2 days. The mixture was then concentrated and the residue partitioned between CH$_2$Cl$_2$ 1M NaOH. The organic portion was dried over MgSO$_4$, and concentrated. Silica gel chromatography eluting with hexanes/ethyl acetate (3:1) gave 2.1 g (29%) of the title compound.

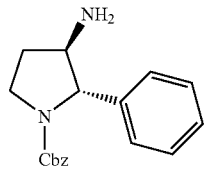

PREPARATORY EXAMPLE 11 trans-3-Amino-2-phenyl-pyrrolidine-1-carboxylic acid benzyl ester D-toluenesulphonic acid trans-3-tert-Butoxycarbonylamino-2-phenyl-pyrrolidine-1-carboxylic acid benzyl ester obtained from preparatory example 10 (1.9 g, 4.8 mmol) was stirred in 45 mL of methylene chloride and 5 mL of trifluoroacetic acid at rt for 3 days. The solution was washed with 3M NaOH, dried through cotton, and concentrated to give 1.42 g of the title compound as a colorless oil. The oil was dissolved in hot ethyl acetate and 1.0 eq. of p-toluenesulphonic acid was added. After stirring at rt for 2 days the resultant solids were collected and dried under vacuum to provide 2.07 g (92%) of the title compound.

PREPARATORY EXAMPLE 12 trans-3-amino-2-(3-chloro-phenyl)-pyrrolidine-1-carboxylic acid benzyl ester p-toluenesulphonate Prepared as in preparatory examples 8-11, wherein trans-2-(3-chloro-phenyl)-pyrrolidine-1,3-dicarboxylic acid 1-tert-butyl ester 3-ethyl ester is substituted for trans-2-phenyl-pyrrolidine-1,3-dicarboxylic acid 1-tert-butyl ester 3-ethyl ester in preparatory example 8.

PREPARATORY EXAMPLE 13 trans-3-amino-2-(4-fluoro-2-methyl-phenyl)-pyrrolidine-1-carboxylic acid benzyl ester p-toluenesulphonate Prepared as in preparatory examples 8-11, wherein trans-2-(2-methyl-4-fluoro-phenyl)-pyrrolidine-1,3-dicarboxylic acid 1-tert-butyl ester 3-ethyl ester is substituted for trans-2-phenyl-pyrrolidine-1,3-dicarboxylic acid 1-tert-butyl ester 3-ethyl ester in preparatory example 8.

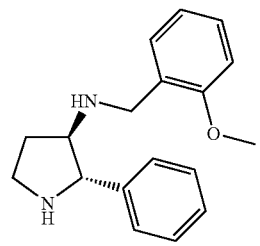

EXAMPLE 67 trans-(2-Methoxy-benzyl)-(2-phenyl-pyrrolidin-3-yl)-amine trans-3-Amino-2-phenyl-pyrrolidine-1-carboxylic acid benzyl ester p-toluenesulfonate (0.253 g, 0.54 mmol) obtained from preparatory example 11, o-anisaldehyde (0.074 g, 0.54 mmol), and sodium triacetoxyborohydride (0.143 g, 0.68 mmol) were stirred in 6 mL of methylene chloride at rt for 2 h. The organic solution was washed 1× with 1M NaOH, dried through cotton, and concentrated to give an oil. The oil was dissolved in methanol (10 mL). Ammonium formate (0.143 g, 2.27 mmol) and 10% palladium on carbon (ca. 20 wt %) were carefully added. The reaction was heated to reflux for 1 hr, and then cooled to rt, filtered carefully through Celite, and concentrated. The residue was dissolved in 1M HCl, washed 2× with CH$_2$Cl$_2$, and basified with excess 3 M NaOH. The aqueous solution was extracted 5× with CH$_2$Cl$_2$ and the combined extracts were dried through cotton and concentrated to give 0.089 g (70%) of the title compound. The dihydrochloride salt was prepared via the addition of concentrated HCl to a solution of the free base in isopropanol and evaporation under vacuum. The residue was crystallized from isopropanol/methanol (ca.1:1). MS APCI: [M+H]$^+$=283.1.

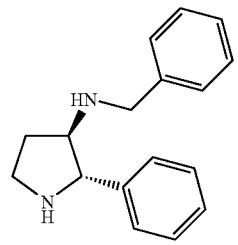

EXAMPLE 68 trans-Benzyl-(2-phenyl-pyrrolidin-3-yl)-amine

A mixture of trans-3-amino-2-phenyl-pyrrolidine-1-carboxylic acid benzyl ester p-toluenesulfonate (0.15 g, 0.32 mmol) obtained from preparatory example 11, benzaldehyde (0.036 g, 0.34 mmol), and sodium triacetoxyborohydride (0.082 g, 0.38 mmol) was stirred in 3 mL of methylene chloride at rt for 16 h. The solution was washed 1× with 1M NaOH, dried through cotton, and concentrated to give an oil. The oil was then dissolved in acetic acid (1 mL) and a solution of 30% hydrogen bromide in acetic acid (0.346 g, 1.28 mmol) was added dropwise. The solution was stirred for 16 h and the resultant solids were collected, washed with ether, triturated with isopropanol, and concentrated under vacuum to give 0.067 g (50%) of the title compound as a white powder. MS APCI: [M+H]$^+$=253.2.

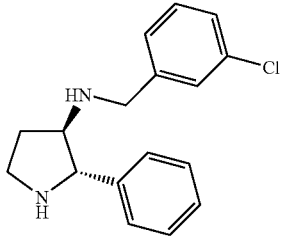

EXAMPLE 69 trans-(3-Chloro-benzyl)-(2-phenyl-pyrrolidin-3-yl)-amine

A mixture of trans-3-amino-2-phenyl-pyrrolidine-1-carboxylic acid benzyl ester p-toluenesulfonate (0.15 g, 0.32 mmol) obtained from preparatory example 11, 3-chlorobenzaldehyde (0.047 g, 0.34 mmol), and sodium triacetoxyborohydride (0.082 g, 0.38 mmol) was stirred in 3 mL of methylene chloride at rt for 16 h. The solution was washed 1× with 1M NaOH, dried through cotton, and concentrated to give an oil. The oil was dissolved in acetic acid (1 mL) and a solution of 30% hydrogen bromide in acetic acid (0.341 g, 1.27 mmol) was added. The solution was stirred for 16 h and the resultant solids were collected, washed with ether, triturated with isopropanol, and concentrated under vacuum to give 0.065 g (46%) of the title compound as a white powder. MS APCI: [M+H]$^+$=287.1.

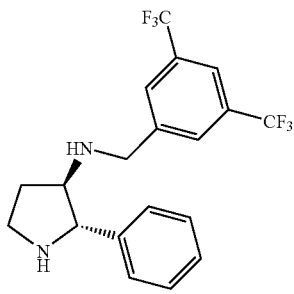

EXAMPLE 70 trans-(3,5-Bis-trifluoromethyl-benzyl)-(2-phenyl-pyrrolidin-3-yl)-amine

A mixture of trans-3-amino-2-phenyl-pyrrolidine-1-carboxylic acid benzyl ester p-toluenesulfonate (0.15 g, 0.32 mmol) obtained from preparatory example 11, 3,5-bistrifluoromethylbenzaldehyde (0.081 g, 0.34 mmol), and sodium triacetoxyborohydride (0.082 g, 0.38 mmol) was stirred in 3 mL of methylene chloride at rt for 16 h. The solution was washed 1× with 1M NaOH, dried through cotton, and concentrated to give an oil. The oil was dissolved in acetic acid (1 mL) and a solution of 30% hydrogen bromide in acetic acid (0.341 g, 1.27 mmol) was added. The solution was stirred for 16 h and the resultant solids were collected, washed with ether, triturated with isopropanol, and concentrated under vacuum to give 0.087 g (50%) of the title compound MS APCI: [M+H]$^+$=388.1

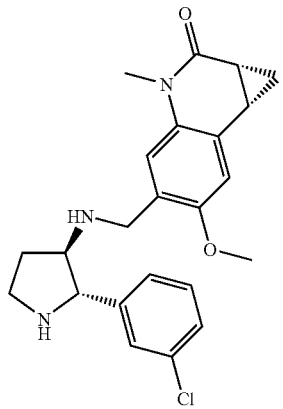

EXAMPLE 71 trans-5-{[2-(3-Chloro-phenyl)-pyrrolidin-3-ylamino]-methyl}-6-methoxy-3-methyl-1,1a,3,7b-tetrahydro-3-aza-cyclopropa[a]naphthalen-2-one A mixture of trans-3-amino-2-(3-chloro-phenyl)-pyrrolidine-1-carboxylic acid benzyl ester p-toluenesulphonate (0.281 g, 0.559 mmol) obtained from preparatory example 12, 6-methoxy-3-methyl-2-oxo-1a,2,3,7b-tetrahydro-1H-3-aza-cyclopropa[a]naphthalene-5-carbaldehyde (0.132 g, 0.57 mmol), and sodium triacetoxyborohydride (0.142 g, 0.67 mmol) were stirred in 11 mL of methylene chloride at rt for 16 h. The solution was washed 1× with 1M NaOH, dried through cotton, and concentrated to give an oil. The oil was dissolved in acetic acid (1.5 mL) and a solution of 30% hydrogen bromide in acetic acid (0.603 g, 2.24 mmol) was added. After stirring for 6 h, the solution was diluted with 1M HCl and washed 3× with CH$_2$Cl$_2$. The aqueous portion was then basified with 6 M NaOH and extracted 3× with CH$_2$Cl$_2$. The combined extracts were dried through cotton, and concentrated. Silica gel chromatography eluting with CH$_2$Cl$_2$/MeOH (9:1) gave 0.156 g of the title compound as an oil. The dissolved in isopropanol and 2.0 eq. of concentrated HCl was added. The solution was concentrated 2× from isopropanol to provide 0.10 g of the dihydrochloride salt. MS APCI: [M+H]$^+$=412.2.

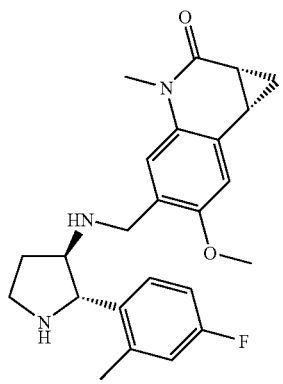

EXAMPLE 72 trans-5-{[2-(4-Fluoro-2-methyl-phenyl)-pyrrolidin-3-ylamino]-methyl}-6-methoxy-3-methyl-1,1a,3,7b-tetrahydro-3-aza-cyclopropa[a]naphthalen-2-one A mixture of trans-3-amino-2-(4-fluoro-2-methyl-phenyl)-pyrrolidine-1-carboxylic acid benzyl ester p-toluenesulphonate (0.105 g, 0.21 mmol) obtained from preparatory example 13, 6-methoxy-3-methyl-2-oxo-1a,2,3,7b-tetrahydro-1 H-3-aza-cyclopropa[a]naphthalene-5-carbaldehyde (0.0485 g, 0.21 mmol), and sodium triacetoxyborohydride (0.0.67 g, 0.315 mmol) was stirred in 4 mL of methylene chloride at rt for 16 h. The solution was washed 1× with 1M NaOH, dried through cotton, and concentrated to give an oil. The oil was dissolved in acetic acid (1 mL) and a solution of 30% hydrogen bromide in acetic acid (0.603 g, 2.24 mmol) was added. After stirring for 6 h the solution was diluted with 1M HCl, washed 3× with ether, basified with 6M NaOH, and extracted 3× with $CH_2Cl_2$. The combined extracts were dried through cotton, and concentrated. The resultant oil was dissolved in isopropanol and 2.0 eq. of concentrated HCl was added. The mixture was concentrated 2× from isopropanol and the residue recrystallized from ethyl acetate/methanol to give 0.014 g of the dihydrochloride salt, as a white powder. MS APCI: $[M+H]^+=410.1$.

REFERENCES

1. Xu, Z. and X. Lu, A Novel [3+2] *Cycloaddition Approach to Nitrogen Heterocycles via Phosphine-Catalyzed Reactions of 2,3-Butadienoates or 2-Butynoates and Dimethyl Acetylenedicarboxylate with Imines: A Convenient Synthesis of Pentabromopseudilin*. J. Org. Chem., 1998. 63: p. 5031-5041.
2. Larock, R. C., *Comprehensive Organic Transformations*. 2nd ed. 1999, New York: John Wiley & Sons.
3. Smith, M. B. and J. March, *March's Advanced Organic Chemistry*. 5th ed. 2001, New York: John Wiley & Sons.
4. Greene, T. W. and P. G. M. Wuts, *Protective Groups in Organic Synthesis*. 1999, New York: John Wiley & Sons.
5. Kocienski, P. J., *Protecting Groups*. 1994, New York: Georg Thieme Verlag Stuttgart.

What is claimed is:

1. A compound having the Formulae:

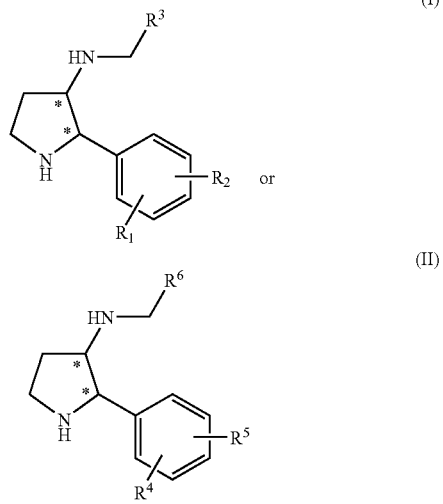

or a pharmaceutically acceptable salt or solvate thereof, wherein:
$R^1$ and $R^2$ are each independently H, $C_{1-6}$ alkyl or halo;
$R^3$ is phenyl, bi-phenyl, 6-methoxy-3-methyl-1,1a,3,7b-tetrahydro-3-aza-cyclopropa[a]naphthalen-2-one, 6-methoxy-1-methyl-3,4-dihydro-1H-[1,5]naphthyridin-2-one-7-yl, dibenzofuranyl, 6-methoxy-3-methyl-1,1a,3,7b-tetrahydro-3-aza-cyclopropa[a]naphthalen-2-one-5-yl or naphthyl, all of which are substituted with 1 to 3 substituents independently selected from hydroxy, $C_{3-6}$ cycloalkoxy, benzo($C_{3-6}$)cycloalkoxy, $C_{1-6}$ alkylthio, tetrazole, or $C_{6-10}$ aryloxy, said aryloxy or tetrazole being optionally substituted with 1 to 3 substituents independently selected from halo, $C_{1-4}$ alkoxy, cyano, $C_{1-4}$ haloalkyl or $C_{1-4}$ alkyl;

or $R^3$ is phenyl, to which is fused a $C_{3-6}$ cycloalkyl, a $C_{4-5}$ lactam, thiazole, pyridone, pyran, dioxolan or benzofuran, wherein the C—N and C-phenyl bonds at the C atoms denoted * are in the cis or trans position relative to each other;

$R^4$ is H or halo;
$R^5$ is H or $C_{1-6}$ alkyl; and
$R^6$ is selected from phenyl, indanyl, pyridinyl, benzothiazoyl, thiophenyl, furanyl, quinolinyl, benzothiophenyl, benzofuranyl, isochromanyl, chromanyl, or naphthyl, and $R^6$ can be optionally substituted with 1 to 3 of the substitutents independently selected from halo, $C_{1-6}$ alkyl, $C_{1-6}$ haloalkyl, $C_{1-6}$ alkoxy, $C_{1-6}$ haloalkoxy, piperidinyl or phenyl; wherein the C—N and C-phenyl bonds at the C atoms denoted * are in the cis or trans position relative to each other, with the provisos that said compound not be cis-3-(2-methoxybenzylamino)-2-phenyl-pyrrolidine, nor 3-(2-methoxy-5-trifluoromethoxybenzyl)amino-2-phenylpyrrolidine.

2. The compound of claim 1, wherein $R^1$ and $R^2$ are each independently H, methyl, Cl or Br; and $R^3$ is (i) phenyl or naphthyl, either one of which may be optionally substituted with 1 to 3 substituents independently selected from $C_{5-6}$ cycloalkoxy, benzo($C_{5-6}$)cycloalkoxy, $C_{1-2}$ alkylthio, tetrazole, phenoxy, said phenoxy being optionally substituted with 1 to 3 substituents independently selected from Cl, Br, F, methoxy, ethoxy, cyano, methyl or ethyl.

3. The compound according to claim 1, wherein
$R^4$ is H or F;
$R^5$ is H or $CH_3$;
$R^6$ is phenyl or naphthyl, either one of which may be optionally substituted with 1 to 3 of the following groups: Cl, F, Br, $C_{1-4}$ alkyl, $C_{1-3}$ fluoroalkyl, $C_{1-3}$ alkoxy, $C_{1-3}$ fluoroalkoxy, phenyl.

4. The compound according to claim 3 wherein said $C_{1-4}$ alkyl is methyl, ethyl, propyl or t-butyl; said $C_{1-3}$ fluoroalkyl is trifluoromethyl; said $C_{1-3}$ alkoxy is methoxy, ethoxy or propoxy; and said $C_{1-3}$ fluoroalkoxy is difluoromethyoxy or trifluoromethoxy.

5. The compound according to claim 1 selected from the group consisting of:
cis-(2-Methoxy-benzyl)-(2-phenyl-pyrrolidin-3-yl)-amine;
cis-(3,5-Bis-trifluoromethyl-benzyl)-(2-phenyl-pyrrolidin-3-yl)-amine;
cis-Benzyl-(2-phenyl-pyrrolidin-3-yl)-amine;
cis-(3-Chloro-benzyl)-(2-phenyl-pyrrolidin-3-yl)-amine;
cis-6-Methoxy-3-methyl-5-[(2-phenyl-pyrrolidin-3-ylamino)-methyl]-1,1a,3,7b-tetrahydro-3-aza-cyclopropa[a]naphthalen-2-one;
cis-Benzyl-[2-(3-chloro-phenyl)-pyrrolidin-3-yl]-amine;
cis-[2-(3-Chloro-phenyl)-pyrrolidin-3-yl]-(2-methoxy-benzyl)-amine;
cis-[2-(3-Chloro-phenyl)-pyrrolidin-3-yl]-(2-difluoromethoxy-benzyl)-amine;

cis-5-{[2-(3-Chloro-phenyl)-pyrrolidin-3-ylamino]-methyl}-6-methoxy-3-methyl-1,1a,3,7b-tetrahydro-3-azacyclopropa[a]naphthalen-2-one;
cis-(5-tert-butyl-2-methoxy-benzyl)-[2-(3-chloro-phenyl)-pyrrolidin-3-yl]-amine;
cis-[2-(3-Chloro-phenyl)-pyrrolidin-3-yl]-(2-methoxy-5-trifluoromethoxy-benzyl)-amine;
cis-[2-(3-Chloro-phenyl)-pyrrolidin-3-yl]-(6-methoxy-3-trifluoromethyl-indan-5-ylmethyl)-amine;
cis-(6-Methoxy-3-trifluoromethyl-indan-5-ylmethyl)-(2-phenyl-pyrrolidin-3-yl)-amine;
cis-[5-(2,2-Difluoro-propyl)-2-methoxy-benzyl]-(2-phenyl-pyrrolidin-3-yl)-amine;
cis-[2-Methoxy-5-(2,2,2-trifluoro-1,1-dimethyl-ethyl)-benzyl]-(2-phenyl-pyrrolidin-3-yl)-amine;
cis-(2-Difluoromethoxy-benzyl)-(2-phenyl-pyrrolidin-3-yl)-amine;
cis-(5-tert-Butyl-2-methoxy-benzyl)-(2-phenyl-pyrrolidin-3-yl)-amine;
cis-(6-Methoxy-3-methyl-3-trifluoromethyl-indan-5-ylmethyl)-(2-phenyl-pyrrolidin-3-yl)-amine;
cis-(5-tert-Butyl-2-methoxy-benzyl)-([2R, 3R]-2-phenyl-pyrrolidin-3-yl)-amine;
cis-(5-tert-Butyl-2-methoxy-benzyl)-([2S, 3S]-2-phenyl-pyrrolidin-3-yl)-amine;
cis-2-[(2-Phenyl-pyrrolidin-3-ylamino)-methyl]-phenol;
cis-3-Amino-2-phenyl-pyrrolidine-1-carboxylic acid benzyl ester p-toluenesulfonate
cis-(2-Isopropoxy-5-trifluoromethoxy-benzyl)-(2-phenyl-pyrrolidin-3-yl)-amine;
cis-6-Methoxy-1-methyl-7-[(2-phenyl-pyrrolidin-3-ylamino)-methyl]-3,4-dihydro-1H-[1,5]naphthyridin-2-one;
cis-(6'-Methoxy-3,4,5,6-tetrahydro-2H-[1,3']bipyridinyl-5'-ylmethyl)-(2-phenyl-pyrrolidin-3-yl)-amine;
cis-(5-Chloro-2-ethoxy-pyridin-3-ylmethyl)-(2-phenyl-pyrrolidin-3-yl)-amine;
cis-Dibenzofuran-2-ylmethyl-(2-phenyl-pyrrolidin-3-yl)-amine;
cis-(2,6-Dichloro-4-methoxy-benzyl)-(2-phenyl-pyrrolidin-3-yl)-amine;
cis-(2-Methoxy-5-trifluoromethoxy-benzyl)-(2-phenyl-pyrrolidin-3-yl)-amine;
cis-(6-Methoxy-2-methyl-benzothiazol-5-ylmethyl)-(2-phenyl-pyrrolidin-3-yl)-amine;
cis-(6-Methoxy-2-phenyl-benzothiazol-7-ylmethyl)-(2-phenyl-pyrrolidin-3-yl)-amine;
cis-(2-Phenyl-pyrrolidin-3-yl)-(2,3,5-trichloro-benzyl)-amine;
cis-[2-(3,4-Dichloro-phenoxy)-5-fluoro-benzyl]-(2-phenyl-pyrrolidin-3-yl)-amine;
cis-[2-Methoxy-5-(5-trifluoromethyl-tetrazol-1-yl)-benzyl]-(2-phenyl-pyrrolidin-3-yl)-amine;
cis-2-[(2-Phenyl-pyrrolidin-3-ylamino)-methyl]-4-(5-trifluoromethyl-tetrazol-1-yl)-phenol;
cis-(5-Chloro-2-methoxy-benzyl)-(2-phenyl-pyrrolidin-3-yl)-amine;
cis-(2,3-Difluoro-benzyl)-(2-phenyl-pyrrolidin-3-yl)-amine;
cis-(2,5-Difluoro-benzyl)-(2-phenyl-pyrrolidin-3-yl)-amine;
cis-(2-Ethoxy-naphthalen-1-ylmethyl)-(2-phenyl-pyrrolidin-3-yl)-amine;
cis-(2-Phenyl-pyrrolidin-3-yl)-(4-propoxy-benzyl)-amine;
cis-(4-Ethyl-benzyl)-(2-phenyl-pyrrolidin-3-yl)-amine;
cis-(3-Ethoxy-4-methoxy-benzyl)-(2-phenyl-pyrrolidin-3-yl)-amine;
cis-(2-Phenyl-pyrrolidin-3-yl)-(2,3,6-trifluoro-benzyl)-amine;
cis-(3-Fluoro-2-methyl-benzyl)-(2-phenyl-pyrrolidin-3-yl)-amine;
cis-(2-Chloro-3,4-dimethoxy-benzyl)-(2-phenyl-pyrrolidin-3-yl)-amine;
cis-(2-Phenyl-pyrrolidin-3-yl)-thiophen-2-ylmethyl-amine;
cis-(2-Bromo-benzyl)-(2-phenyl-pyrrolidin-3-yl)-amine;
cis-(5-Bromo-2-methoxy-benzyl)-(2-phenyl-pyrrolidin-3-yl)-amine;
cis-(5-Methyl-furan-2-ylmethyl)-(2-phenyl-pyrrolidin-3-yl)-amine;
cis-(3-Methyl-thiophen-2-ylmethyl)-(2-phenyl-pyrrolidin-3-yl)-amine;
cis-(4-Phenoxy-benzyl)-(2-phenyl-pyrrolidin-3-yl)-amine;
cis-(2-Bromo-4,5-dimethoxy-benzyl)-(2-phenyl-pyrrolidin-3-yl)-amine;
cis-(2,3-Dichloro-benzyl)-(2-phenyl-pyrrolidin-3-yl)-amine;
cis-[3-(4-Methoxy-phenoxy)-benzyl]-(2-phenyl-pyrrolidin-3-yl)-amine;
cis-(2-Chloro-4-fluoro-benzyl)-(2-phenyl-pyrrolidin-3-yl)-amine;
cis-(5-Ethyl-furan-2-ylmethyl)-(2-phenyl-pyrrolidin-3-yl)-amine;
cis-(2-Chloro-quinolin-3-ylmethyl)-(2-phenyl-pyrrolidin-3-yl)-amine;
cis-(3-Methyl-benzo[b]thiophen-2-ylmethyl)-(2-phenyl-pyrrolidin-3-yl)-amine;
cis-Benzofuran-2-ylmethyl-(2-phenyl-pyrrolidin-3-yl)-amine;
cis-(2-Chloro-benzyl)-(2-phenyl-pyrrolidin-3-yl)-amine;
cis-(6-Methoxy-1-methyl-1-trifluoromethyl-isochroman-7-ylmethyl)-(2-phenyl-pyrrolidin-3-yl)-amine;
cis-2-Chloro-6-{3-[(2-phenyl-pyrrolidin-3-ylamino)-methyl]-phenoxy}-benzonitrile;
cis-(6-Bromo-2,3-dimethoxy-benzyl)-(2-phenyl-pyrrolidin-3-yl)-amine;
cis-(2-Bromo-3,6-dimethoxy-benzyl)-(2-phenyl-pyrrolidin-3-yl)-amine;
cis-(2,2-Dimethyl-chroman-6-ylmethyl)-(2-phenyl-pyrrolidin-3-yl)-amine;
cis-[3-(4-Ethyl-phenoxy)-benzyl]-(2-phenyl-pyrrolidin-3-yl)-amine;
trans-(2-Methoxy-benzyl)-(2-phenyl-pyrrolidin-3-yl)-amine;
trans-Benzyl-(2-phenyl-pyrrolidin-3-yl)-amine;
trans-(3-Chloro-benzyl)-(2-phenyl-pyrrolidin-3-yl)-amine;
trans-(3,5-Bis-trifluoromethyl-benzyl)-(2-phenyl-pyrrolidin-3-yl)-amine;
trans-5-{[2-(3-Chloro-phenyl)-pyrrolidin-3-ylamino]-methyl}-6-methoxy-3-methyl-1,1a,3,7b-tetrahydro-3-aza-cyclopropa[a]naphthalen-2-one; and
trans-5-{[2-(4-Fluoro-2-methyl-phenyl)-pyrrolidin-3-ylamino]-methyl}-6-methoxy-3-methyl-1,1a,3,7b-tetrahydro-3-aza-cyclopropa[a]naphthalen-2-one;
or a pharmaceutically acceptable salt or solvate thereof.

6. The compound according to claim 5 selected from the group consisting of:
6-Methoxy-3-methyl-5-[(2-phenyl-pyrrolidin-3-ylamino)-methyl]-1,1a,3,7b-tetrahydro-3-aza-cyclopropa[a]naphthalen-2-one;

5-[2-(3-Chloro-phenyl)-pyrrolidin-3-ylamino]-methyl}-6-methoxy-3-methyl-1,1a,3,7b-tetrahydro-3-aza-cyclopropa[a]naphthalen-2-one;

[2-(3-Chloro-phenyl)-pyrrolidin-3-yl]-(6-methoxy-3-trifluoromethyl-indan-5-ylmethyl)-amine;

(6-Methoxy-3-trifluoromethyl-indan-5-ylmethyl)-(2-phenyl-pyrrolidin-3-yl)-amine;

6-Methoxy-3-methyl-3-trifluoromethyl-indan-5-ylmethyl)-(2-phenyl-pyrrolidin-3-yl)-amine;

2-[(2-Phenyl-pyrrolidin-3-ylamino)-methyl]-phenol;

Dibenzofuran-2-ylmethyl-(2-phenyl-pyrrolidin-3-yl)-amine;

(6-Methoxy-2-methyl-benzothiazol-5-ylmethyl)-(2-phenyl-pyrrolidin-3-yl)-amine;

(6-Methoxy-2-phenyl-benzothiazol-7-ylmethyl)-(2-phenyl-pyrrolidin-3-yl)-amine;

[2-(3,4-Dichloro-phenoxy)-5-fluoro-benzyl]-(2-phenyl-pyrrolidin-3-yl)-amine;

[2-Methoxy-5-(5-trifluoromethyl-tetrazol-1-yl)-benzyl]-(2-phenyl-pyrrolidin-3-yl)-amine;

2-[(2-Phenyl-pyrrolidin-3-ylamino)-methyl]-4-(5-trifluoromethyl-tetrazol-1-yl)-phenol;

(4-Phenoxy-benzyl)-(2-phenyl-pyrrolidin-3-yl)-amine;

[3-(4-Methoxy-phenoxy)-benzyl]-(2-phenyl-pyrrolidin-3-yl)-amine;

(6-Methoxy-1-methyl-1-trifluoromethyl-isochroman-7-ylmethyl)-(2-phenyl-pyrrolidin-3-yl)-amine;

2-Chloro-6-{3-[(2-phenyl-pyrrolidin-3-ylamino)-methyl]-phenoxy}-benzonitrile;

cis-5-{[2-(3-Chloro-phenyl)-pyrrolidin-3-ylamino]-methyl}-6-methoxy-3-methyl-1,1a,3,7b-tetrahydro-3-aza-cyclopropa[a]naphthalen-2-one;

cis-6-Methoxy-1-methyl-7-[(2-phenyl-pyrrolidin-3-ylamino)-methyl]-3,4-dihydro-1H-[1,5]naphthyridin-2-one;

trans-5-{[2-(4-Fluoro-2-methyl-phenyl)-pyrrolidin-3-ylamino]-methyl}-6-methoxy-3-methyl-1,1a,3,7b-tetrahydro-3-aza-cyclopropa[a]naphthalen-2-one;

(2,2-Dimethyl-chroman-6-ylmethyl)-(2-phenyl-pyrrolidin-3-yl)-amine;

[3-(4-Ethyl-phenoxy)-benzyl]-(2-phenyl-pyrrolidin-3-yl)-amine;

or a pharmaceutically acceptable salt or solvate thereof.

7. The compound according to claim 5 selected from the group consisting of:

cis-(2-Methoxy-benzyl)-(2-phenyl-pyrrolidin-3-yl)-amine;

cis-(3-Chloro-benzyl)-(2-phenyl-pyrrolidin-3-yl)-amine;

cis-(6'-Methoxy-3,4,5,6-tetrahydro-2H-[1,3']bipyridinyl-5'-ylmethyl)-(2-phenyl-pyrrolidin-3-yl)-amine dihydrochloride;

cis-(5-Chloro-2-ethoxy-pyridin-3-ylmethyl)-(2-phenyl-pyrrolidin-3-yl)-amine;

cis-(2-Phenyl-pyrrolidin-3-yl)-(4-propoxy-benzyl)-amine;

cis-(2-Bromo-benzyl)-(2-phenyl-pyrrolidin-3-yl)-amine;

cis-(5-Methyl-furan-2-ylmethyl)-(2-phenyl-pyrrolidin-3-yl)-amine;

cis-(3-Methyl-thiophen-2-ylmethyl)-(2-phenyl-pyrrolidin-3-yl)-amine;

cis-(5-Ethyl-furan-2-ylmethyl)-(2-phenyl-pyrrolidin-3-yl)-amine;

cis-(2-Chloro-quinolin-3-ylmethyl)-(2-phenyl-pyrrolidin-3-yl)-amine;

cis-(3-Methyl-benzo[b]thiophen-2-ylmethyl)-(2-phenyl-pyrrolidin-3-yl)-amine;

cis-Benzofuran-2-ylmethyl-(2-phenyl-pyrrolidin-3-yl)-amine;

trans-(2-methoxy-benzyl)-(2-phenyl-pyrrolidin-3-yl)-amine;

trans-(3-Chloro-benzyl)-(2-phenyl-pyrrolidin-3-yl)-amine;

trans-(3,5-Bis-trifluoromethyl-benzyl)-(2-phenyl-pyrrolidin-3-yl)-amine;

(3,5-Bis-trifluoromethyl-benzyl)-(2-phenyl-pyrrolidin-3-yl)-amine;

cis-Benzyl-(2-phenyl-pyrrolidin-3-yl)-amine;

tran-Benzyl-(2-phenyl-pyrrolidin-3-yl)-amine;

cis-Benzyl-[2-(3-chloro-phenyl)-pyrrolidin-3-yl]-amine;

cis-[2-(3-Chloro-phenyl)-pyrrolidin-3-yl]-(2-methoxy-benzyl)-amine;

cis-[2-(3-Chloro-phenyl)-pyrrolidin-3-yl]-(2-difluoromethoxy-benzyl)-amine;

cis-(5-tert-Butyl-2-methoxy-benzyl)-[2-(3-chloro-phenyl)-pyrrolidin-3-yl]-amine;

cis-[2-(3-Chloro-phenyl)-pyrrolidin-3-yl]-(2-methoxy-5-trifluoromethoxy-benzyl)-amine;

cis-[5-(2,2-Difluoro-propyl)-2-methoxy-benzyl]-(2-phenyl-pyrrolidin-3-yl)-amine;

cis-[2-Methoxy-5-(2,2,2-trifluoro-1,1-dimethyl-ethyl)-benzyl]-(2-phenyl-pyrrolidin-3-yl)-amine;

cis-(2-Difluoromethoxy-benzyl)-(2-phenyl-pyrrolidin-3-yl)-amine;

cis-(5-tert-Butyl-2-methoxy-benzyl)-(2-phenyl-pyrrolidin-3-yl)-amine;

cis-(5-tert-Butyl-2-methoxy-benzyl)-(2-phenyl-pyrrolidin-3-yl)-amine;

cis-(5-tert-Butyl-2-methoxy-benzyl)-(2-phenyl-pyrrolidin-3-yl)-amine;

cis-(2-Isopropoxy-5-trifluoromethoxy-benzyl)-(2-phenyl-pyrrolidin-3-yl)-amine;

cis-(2,6-Dichloro-4-methoxy-benzyl)-(2-phenyl-pyrrolidin-3-yl)-amine;

cis-(2-Methoxy-5-trifluoromethoxy-benzyl)-(2-phenyl-pyrrolidin-3-yl)-amine;

cis-(2-Phenyl-pyrrolidin-3-yl)-(2,3,5-trichloro-benzyl)-amine;

cis-(5-Chloro-2-methoxy-benzyl)-(2-phenyl-pyrrolidin-3-yl)-amine;

cis-(2,3-Difluoro-benzyl)-(2-phenyl-pyrrolidin-3-yl)-amine;

cis-(2,5-Difluoro-benzyl)-(2-phenyl-pyrrolidin-3-yl)-amine;

cis-(2-Ethoxy-naphthalen-1-ylmethyl)-(2-phenyl-pyrrolidin-3-yl)-amine;

cis-(2-Phenyl-pyrrolidin-3-yl)-(4-propoxy-benzyl)-amine;

cis-(4-Ethyl-benzyl)-(2-phenyl-pyrrolidin-3-yl)-amine;

cis-(3-Ethoxy-4-methoxy-benzyl)-(2-phenyl-pyrrolidin-3-yl)-amine;

cis-(2-Phenyl-pyrrolidin-3-yl)-(2,3,6-trifluoro-benzyl)-amine;

cis-(3-Fluoro-2-methyl-benzyl)-(2-phenyl-pyrrolidin-3-yl)-amine;

cis-(2-Chloro-3,4-dimethoxy-benzyl)-(2-phenyl-pyrrolidin-3-yl)-amine;

cis-(2-Phenyl-pyrrolidin-3-yl)-thiophen-2-ylmethyl-amine;

cis-5-Bromo-2-methoxy-benzyl)-(2-phenyl-pyrrolidin-3-yl)-amine;

cis-(2-Bromo-4,5-dimethoxy-benzyl)-(2-phenyl-pyrrolidin-3-yl)-amine;
cis-(2,3-Dichloro-benzyl)-(2-phenyl-pyrrolidin-3-yl)-amine;
cis-(2-Chloro-4-fluoro-benzyl)-(2-phenyl-pyrrolidin-3-yl)-amine;
cis-(2-Chloro-benzyl)-(2-phenyl-pyrrolidin-3-yl)-amine;
cis-(6-Bromo-2,3-dimethoxy-benzyl)-(2-phenyl-pyrrolidin-3-yl)-amine; and
cis-(2-Bromo-3,6-dimethoxy-benzyl)-(2-phenyl-pyrrolidin-3-yl)-amine;
and pharmaceutically acceptable salts and solvates thereof.

8. A pharmaceutical composition comprising a compound according to claim 1, or a pharmaceutically acceptable salt or solvate thereof, and a pharmaceutically acceptable carrier.

* * * * *